United States Patent
Yang et al.

(10) Patent No.: US 9,416,144 B2
(45) Date of Patent: Aug. 16, 2016

(54) BENZOXAZINE OXAZOLIDINONE COMPOUND, PREPARATION METHOD AND APPLICATION THEREOF

(71) Applicants: SHANGHAI INSTITUTE OF MATERIA MEDICA, CHINESE ACADEMY OF SCIENCES, Shanghai (CN); ZHE JIANG JUTAI PHARMACEUTICAL CO., LTD., Quzhou (CN)

(72) Inventors: Yushe Yang, Shanghai (CN); Bin Guo, Shanghai (CN)

(73) Assignees: SHANGHAI INSTITUTE OF MATERIA MEDICA, CHINESE ACADEMY OF SCIENCES, Shanghai (CN); ZHE JIANG JUTAI PHARMACEUTICAL CO., LTD., Quzhou (CN)

( * ) Notice: Subject to any disclaimer, the term of this patent is extended or adjusted under 35 U.S.C. 154(b) by 0 days.

(21) Appl. No.: 14/655,670

(22) PCT Filed: Dec. 25, 2013

(86) PCT No.: PCT/CN2013/090410
§ 371 (c)(1),
(2) Date: Jun. 25, 2015

(87) PCT Pub. No.: WO2014/101765
PCT Pub. Date: Jul. 3, 2014

(65) Prior Publication Data
US 2015/0336984 A1     Nov. 26, 2015

(30) Foreign Application Priority Data
Dec. 26, 2012 (CN) .......................... 2012 1 0576376

(51) Int. Cl.
C07D 498/04     (2006.01)
C07D 519/00     (2006.01)
C07F 7/18       (2006.01)
C07F 5/02       (2006.01)
C07F 9/6561     (2006.01)

(52) U.S. Cl.
CPC ............ *C07D 498/04* (2013.01); *C07D 519/00* (2013.01); *C07F 5/025* (2013.01); *C07F 7/1872* (2013.01); *C07F 9/6561* (2013.01)

(58) Field of Classification Search
CPC ........................... C07D 498/04; C07D 519/00
USPC ........................................ 544/101; 514/230.2
See application file for complete search history.

(56) References Cited

FOREIGN PATENT DOCUMENTS

CN         102260277 A     11/2011

OTHER PUBLICATIONS

Bin et al. J. Med. Chem., 2013, 56(6), 2642-2650.*
International Search Report (English Translation) corresponding to PCT/CN2013/090410 mailed Apr. 3, 2014 (3 pages).
Barbachyn, Michael R. et al., "Oxazolidinone Structure-Activity Relationships Leading to Linezolid," *Angew. Chem. Int. Ed.* (2003) 42:2010-2023.
Genin, Michael J., "Recent progress with oxazolidinone antibacterial agents," *Exp. Opin. Ther. Patents* (2009) 10(9):1405-1414.
Guo, Bin et al., "Synthesis and biological evaluation of novel benzoxazinyl-oxazolidinones as potential antibacterial agents," *Bioorg. Med. Chem. Lett. 23* (2013) 3697-3699.
Guo, Bin et al., "Solubility-Driven Optimization of (Pyridin-3-yl) Benzoxazinyl-oxazolidinones Leading to a Promising Antibacterial Agent," *J. Med. Chem.* (2013) 56:2642-2650.
Hutchinson, Douglas K., "Oxazolidinone Antibacterial Agents: A Critical Review," *Current Topics in Medicinal Chemistry* (2003) 3:1021-1042.
Hutchinson, Douglas K., "Recent advances in oxazolidinone antibacterial agent research," *Expert Opin. Ther. Patents* (2004) 14(9):1309-1328.
Jones, Ronald N. et al., "In Vitro Antimicrobial Activities and Spectra of U-100592 and U-100766, Two Novel Fluorinated Oxazolidinones," *Antimicrobial Agents and Chemotherapy* (Mar. 1996) 40(3):720-726.
Poce, Giovanna et al., "New oxazolidinone derivatives as antibacterial agents with improved activity," *Expert Opin. Ther. Patents* (2008) 18(2)97-121.
Srivastava, Brijesh Kumar et al., "Oxazolidinone Antibacterials and Our Experience," *Anti-Infective Agents in Medicinal Chemistry* (2008) 7(4):258-280.

(Continued)

*Primary Examiner* — Kahsay Habte
(74) *Attorney, Agent, or Firm* — Mintz, Levin, Cohn, Ferris, Glovsky and Popeo, PC

(57) ABSTRACT

Disclosed are a benzoxazine oxazolidinone compound shown by a general formula (I), an optical isomer thereof or a pharmaceutically acceptable salt thereof, a preparation method thereof, and an application thereof in preparing a drug for treating an infectious disease and in particular, an infectious disease caused by multidrug resistant bacteria.

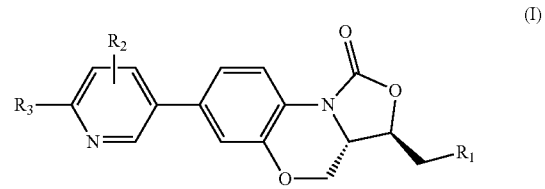

10 Claims, No Drawings

(56) References Cited

OTHER PUBLICATIONS

Wang, Guijun, "Synthesis and Antibacterial Properties of Oxazolidinones and Oxazinanones," *Anti-Infective Agents in Medicinal Chemistry* (2008) 7(1):32-49.

Xin, Qisheng et al., "Design, Synthesis, and Structure—Activity Relationship Studies of Highly Potent Novel Benzoxazinyl-Oxazolidinone Antibacterial Agents," *J. Med. Chem.* (2011) 54:7493-7502.

* cited by examiner

BENZOXAZINE OXAZOLIDINONE COMPOUND, PREPARATION METHOD AND APPLICATION THEREOF

TECHNICAL FIELD

The invention belongs to the field of medicine, relates to the fields of pharmaceutical chemistry and pharmacology, and more specifically it is directed to novel benzoxazine oxazolidinone compounds, processes for their preparation and use thereof in preparation of medicines for treating infectious diseases, in particular infectious diseases caused by multidrug resistant bacteria.

BACKGROUND ART

The worldwide appearance of methicillin-resistant *Staphylococcus aureus* (MRSA) and *Staphylococcus epidermidis* (MRSE), drug-resistant *Streptococcus pneumnoniae*, multi-drug-resistant *Mycobacterium tuberculosis* and vancomycin-resistant enterococci (VRE) is the toughest problem in the current clinical anti-infection treatment (Exp. Opin. Ther. Patents, 2000, 10 (9): 1405; Exp. Opin. Ther. Patents, 2004, 14 (9): 1309). Facing the challenges caused by multidrug-resistant bacteria, antibacterial drugs having new action mechanisms must be developed.

Oxazolidinones are a new class of antibiotics, which has potent antibacterial activity on both multidrug-resistant gram-positive bacteria, such as methicillin-resistant *Staphylococcus aureus*, vancomycin-resistant enterococci, penicillin-resistant *Streptococcus pneumoniae*, and sensitive gram-positive bacteria (Angew. Chem. Int. Ed., 2003, 42: 2010; Current Topics in Medicinal Chemistry, 2003, 3: 1021). Oxazolidinones inhibit the early stage of bacterial protein synthesis. Its completely novel structure distinct from the existing antibiotics and its unique antibacterial mechanism attracted attention of numerous pharmaceutical companies. Many oxazolidinone compounds having different types of structures have been reported (Expert Opin. Ther. Patents. 2008, 18, 97-121; Anti-Infective in Medicinal Chemistry, 2008, 7, 32-49; Anti-infective in Medicinal Chemistry, 2008, 7, 258-280). Among them, linezolid developed by an American company, Upjohn, was approved by the FDA in 2000 to be firstly sold in the United States under the brand name Zyvox, thereby becoming the first oxazolidinone drug allowed to enter clinical application. However, the existing drugs have narrow antimicrobial spectrum, unsatisfied antibacterial activity and side effects such as bone marrow suppression, and furthermore, linezolid-resistant staphylococci and enterococci have appeared in clinics. Therefore, there is a need for researching and developing new oxazolidinone drugs with stronger antibacterial activity, lower side effects, and particularly, with effectiveness on linezolid-resistant strains.

The present invention provides a class of novel oxazolidinone compounds with stronger antibacterial activities, particularly activities against multidrug-resistant bacteria.

SUMMARY OF INVENTION

An objective of the present invention is to provide a benzoxazine oxazolidinone compound of general formula (I), an optical isomer thereof or a pharmaceutically acceptable salt thereof.

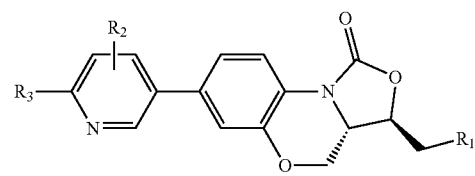

wherein,
$R_1$ is hydroxyl,

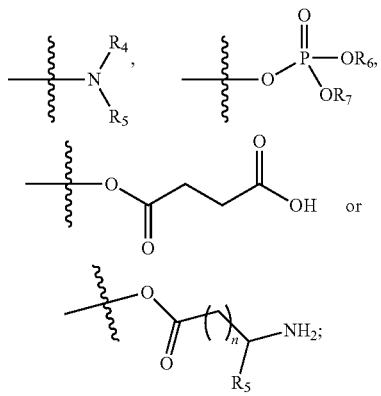

Wherein,
$R_4$ and $R_5$ are each independently H, hydroxyl, $C_1$-$C_4$ straight-chain or branched alkyl, and $R_4$ and $R_5$ are not hydroxyl at the same time;
$R_6$ and $R_7$ are each independently H, $C_1$-$C_4$ straight-chain or branched alkyl, $C_6$-$C_{10}$ aryl, $C_6$-$C_{10}$ aryl, $C_1$-$C_4$ alkyl, preferably benzyl or tert-butyl;
$R_8$ is H, $C_1$-$C_4$ straight-chain or branched alkyl, $C_6$-$C_{10}$ aryl, $C_6$-$C_{10}$ aryl, $C_1$-$C_4$ alkyl, preferably methyl, isopropyl, isobutyl, tert-butyl or benzyl;
N is 0 or 1;
$R_2$ represents 1-3 substituents, which are each the same or different, and which are each independently $C_1$-$C_4$ straight-chain or branched alkyl; preferably methyl, ethyl, propyl, isopropyl or butyl;
$R_3$ is halogen; —CN; $C_1$-$C_6$ straight-chain or branched alkyl substituted by one or more groups selected from the group consisting of hydroxyl, oxo, halogen, amino, $C_3$-$C_6$ cycloalkyl and substituted or unsubstituted 5- or 6-membered aromatic heterocyclic group containing at least one heteroatom selected from N, O or S, preferably said substituted $C_1$-$C_6$ straight-chain or branched alkyl is $C_1$-$C_4$ straight-chain or branched alkyl substituted by the above mentioned substituents, more preferably said substituted $C_1$-$C_6$ straight-chain or branched alkyl is methyl, ethyl, propyl, isopropyl or butyl substituted by the above mentioned substituents; 3- to 6-membered cycloalkyl, which is unsubstituted or substituted by amino, $C_1$-$C_4$ straight-chain or branched alkyl or hydroxyl;

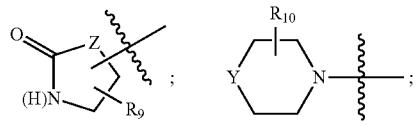

-continued

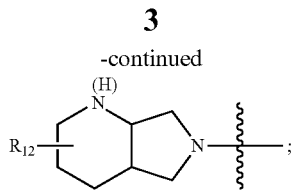

the substituent for said substituted 5- or 6-membered aromatic heterocyclic group containing at least one heteroatom selected from N, O or S is $C_1$-$C_4$ straight-chain or branched alkyl; Z is C, N or O;

$R_9$ represents 1 or 2 substituents, which are the same or different, and which are each independently selected from the group consisting of H; $C_1$-$C_4$ straight-chain or branched alkyl; benzyl; $C_1$-$C_4$ straight-chain-chain or branched alkyl substituted by one or more groups selected from the group consisting of hydroxyl, oxo and amino; and

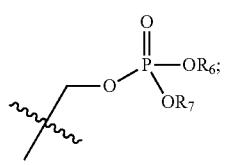

Y is C, N or O;

$R_{10}$ represents one or more substituents, which are each independently selected from the group consisting of H, hydroxyl, oxo and $C_1$-$C_4$ straight-chain or branched alkyl;

$R_{12}$ represents one or more substituents, which are each selected from the group consisting of H, hydroxyl, halogen or $C_1$-$C_4$ straight-chain or branched alkyl;

Preferably, $R_3$ is CN, hydroxylmethyl, methylcarbonyl, aminomethyl,

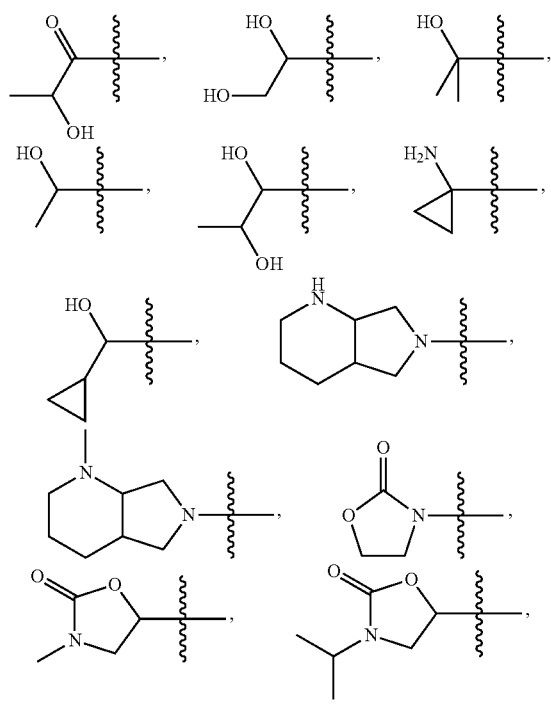

-continued

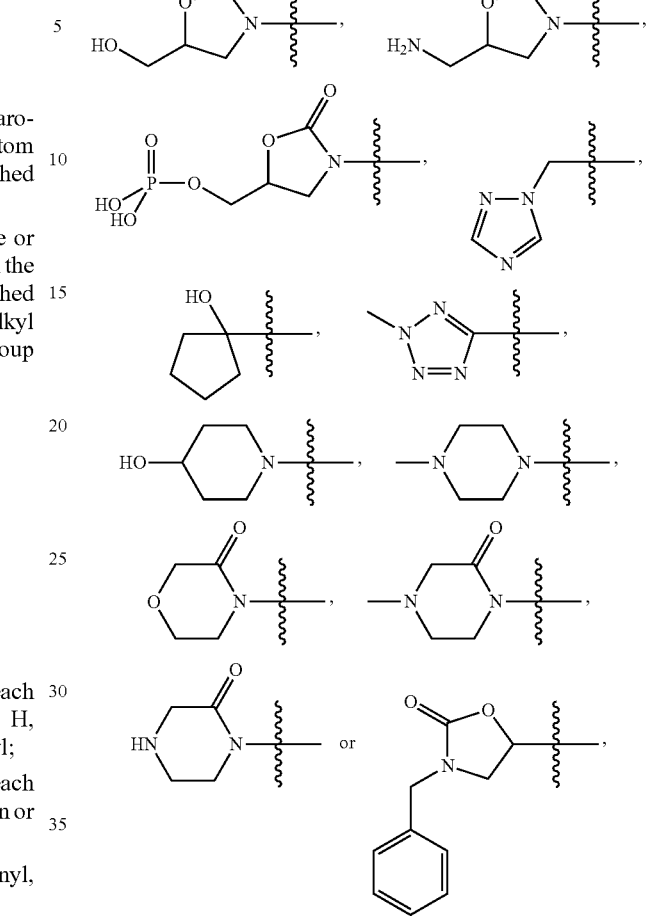

wherein

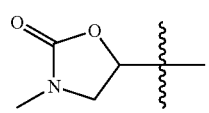 [SMILES: *C1CN(C)C(=O)O1]

can be

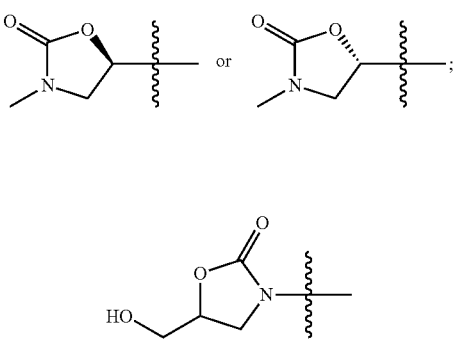

can be

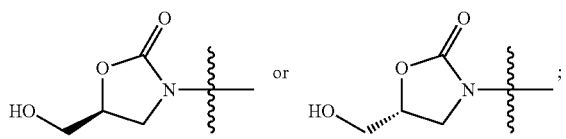 [SMILES: *N1C[C@@H](CO)OC1=O ; *N1C[C@H](CO)OC1=O]

can be

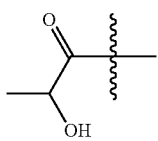 [SMILES: *C(=O)C(C)O]

can be

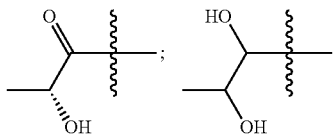

can be

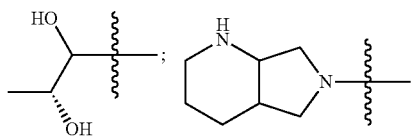

can be

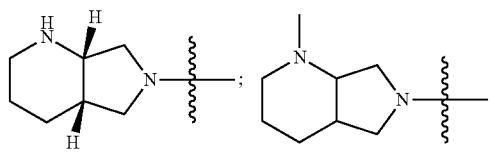 [SMILES: *N1C[C@@H]2CCCN[C@@H]2C1 ; *N1CC2CCCN(C)C2C1]

can be

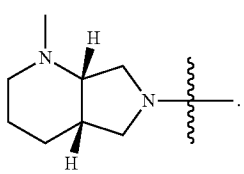 [SMILES: *N1C[C@@H]2CCCN(C)[C@@H]2C1]

The pharmaceutically acceptable salts of the benzoxazine oxazolidinone compounds represented by general formula (I) include: salts formed with inorganic acids such as hydrochloric acid, hydrobromic acid, hydrofluoric acid, sulfuric acid, nitric acid or phosphoric acid, and the like; addition salts formed with organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, ethyl sulfonic acid or benzenesulfonic acid, and the like, or with acidic amino acids such as aspartic acid, glutamic acid, and the like; metal salts formed with alkali such as sodium hydroxide, sodium carbonate, sodium bicarbonate, sodium isooctoate, calcium chloride, magnesium chloride, preferably sodium salt, magnesium salt or calcium salt; addition salts formed with basic amino acids such as arginine acid or lysine, and the like.

Another objective of the present invention is to provide a process for preparing the benzoxazine oxazolidinone compound of general formula (I) described above, an optical isomer thereof or a pharmaceutically acceptable salt thereof.

Still another objective of the present invention is to provide a pharmaceutical composition comprising a therapeutically effective amount of one or more of the benzoxazine oxazolidinone compounds of general formula (I) described above, an optical isomer thereof or a pharmaceutically acceptable salt (including inorganic salts or organic salts) thereof as active ingredient, and a pharmaceutically acceptable auxiliary material.

Yet another objective of the present invention is to provide use of the benzoxazine oxazolidinone compound of general formula (I) described above, an optical isomer thereof or a pharmaceutically acceptable salt thereof in the manufacture of a medicine for treating infectious diseases, in particular infectious diseases caused by multidrug-resistant bacteria including enterococci, *Staphylococcus aureus, Staphylococcus epidermidis* and *Streptococcus pneumoniae.*

SPECIFIC MODES FOR CARRYING OUT THE INVENTION

Upon extensive research, the inventors have synthesized a series of compounds, and by using antimicrobial activity screening, pharmacokinetic screening and physicochemical properties investigations, found for the first time that benzoxazine oxazolidinone compounds represented by the following general formula (I) have very strong antimicrobial activity, excellent pharmacokinetic properties and physicochemical properties, and are especially suitable for being used as a drug for anti-infection treatment. The inventor has completed the present invention based thereon.

The benzoxazine oxazolidinone compound of general formula (I) according to the present invention contains at least two chiral centers, and it has enantiomers and diastereoisomers. For enantiomers, two enantiomers can be obtained by regular chiral separation or asymmetric synthesis. For diastereoisomers, the separation can be achieved by approaches such as fractional recrystallization or chromatographic separation. The benzoxazine oxazolidinone compounds of general formula (I) according to the present invention include any one of such isomers or the mixtures thereof.

The pharmaceutically acceptable salts of the benzoxazine oxazolidinone compounds represented by general formula (I) can be specifically exemplified as salts formed by the benzoxazine oxazolidinone compounds of general formula (I) described above and inorganic acids such as hydrochloric acid, hydrobromic acid, hydrofluoric acid, sulfuric acid, nitric acid or phosphoric acid, and the like; addition salts formed with organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, ethyl sulfonic acid or benzenesulfonic acid, and the like, or with acidic amino acids such as aspartic acid, glutamic acid, and the like; salts formed with alkali such as sodium hydroxide, sodium carbonate, sodium bicarbonate, sodium isooctoate, calcium chloride, magnesium chloride; addition salts formed with basic amino acids such as arginine acid or lysine, and the like.

When the benzoxazine oxazolidinone compounds of general formula (I) according to the present invention or the pharmaceutically acceptable salts thereof are used for preparing antimicrobial agents, they can either be used alone, or can be mixed with pharmaceutically acceptable auxiliary materials (for example, excipients, diluents, etc.) to formulate tablet, capsule, granules, or syrup for oral administration, or to formulate liniment or injection for non-oral administration.

Preferably, the chemical structure of the representative compounds among the benzoxazine oxazolidinone compounds of general formula (I) according to the present invention is shown as follows (or Table 1):

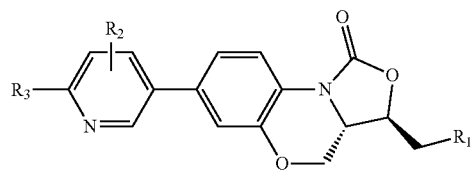

(I)

TABLE 1

Representative Compounds

| Compound | Structure |
| --- | --- |
| 1 | 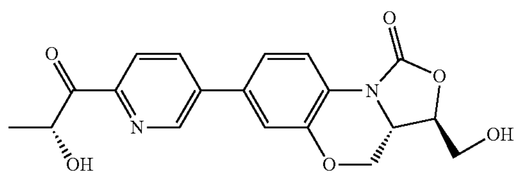 [SMILES: C[C@@H](O)C(=O)c1ccc(-c2ccc3c(c2)OC[C@H]2[C@H](CO)OC(=O)N32)cn1] |
| 2 | 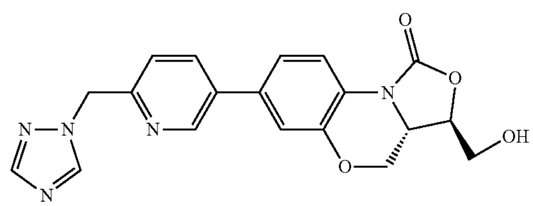 [SMILES: O=C1O[C@@H](CO)[C@@H]2COc3cc(-c4ccc(Cn5cncn5)nc4)ccc3N12] |
| 3 | 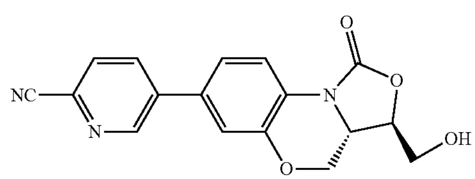 [SMILES: N#Cc1ccc(-c2ccc3c(c2)OC[C@H]2[C@H](CO)OC(=O)N32)cn1] |
| 4 | 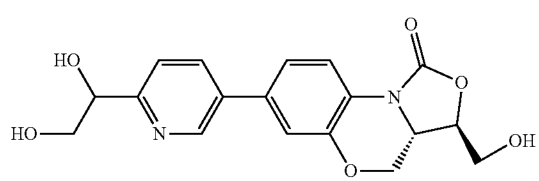 [SMILES: O=C1O[C@@H](CO)[C@@H]2COc3cc(-c4ccc(C(O)CO)nc4)ccc3N12] |
| 5 | 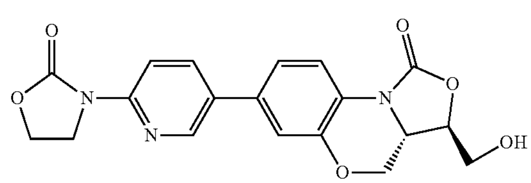 [SMILES: O=C1OCCN1c1ccc(-c2ccc3c(c2)OC[C@H]2[C@H](CO)OC(=O)N32)cn1] |
| 6 | 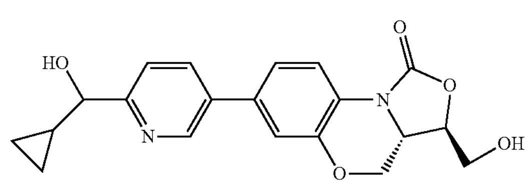 [SMILES: O=C1O[C@@H](CO)[C@@H]2COc3cc(-c4ccc(C(O)C5CC5)nc4)ccc3N12] |

TABLE 1-continued
Representative Compounds
| Compound | Structure |
|---|---|
| 7 | 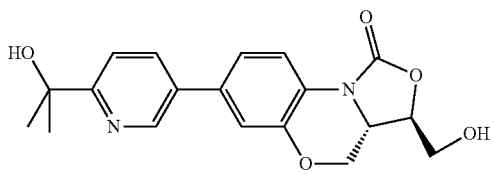 [SMILES: CC(C)(O)c1ccc(-c2ccc3c(c2)OC[C@H]2[C@H](CO)OC(=O)N32)cn1] |
| 8 | 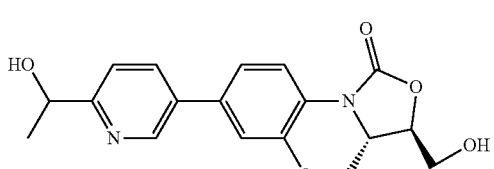 |
| 9 | 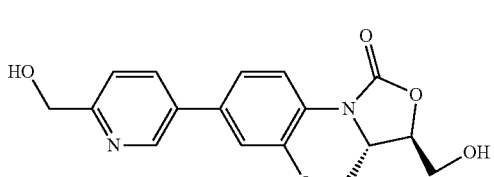 |
| 10 | 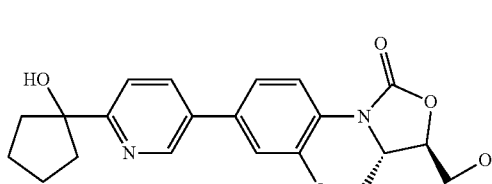 |
| 11 | 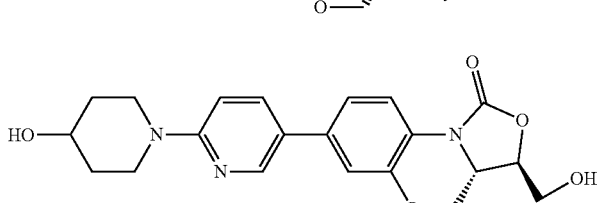 |
| 12 | 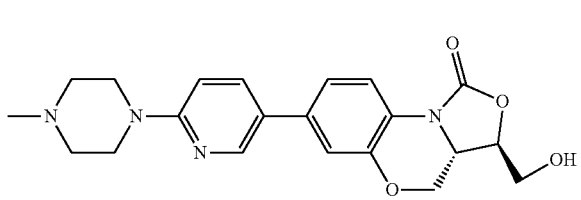 [SMILES: CN1CCN(c2ccc(-c3ccc4c(c3)OC[C@H]3[C@H](CO)OC(=O)N43)cn2)CC1] |
| 13 | 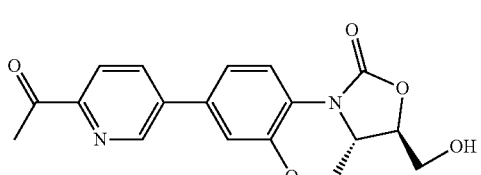 |
| 14 | 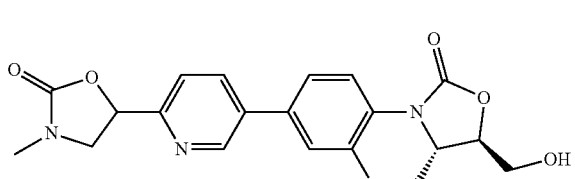 |

TABLE 1-continued

Representative Compounds

| Compound | Structure |
|---|---|
| 15 | 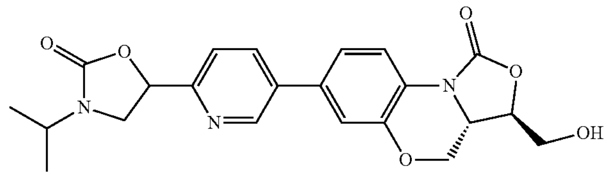 [SMILES: CC(C)N1CC(c2ccc(-c3ccc4c(c3)OC[C@H]3[C@H](CO)OC(=O)N43)cn2)OC1=O] |
| 16 | 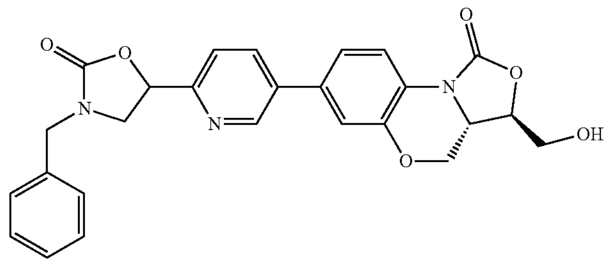 [SMILES: O=C1OC(c2ccc(-c3ccc4c(c3)OC[C@H]3[C@H](CO)OC(=O)N43)cn2)CN1Cc1ccccc1] |
| 17 | 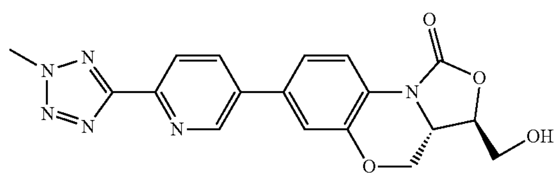 [SMILES: Cn1nnc(-c2ccc(-c3ccc4c(c3)OC[C@H]3[C@H](CO)OC(=O)N43)cn2)n1] |
| 18 | 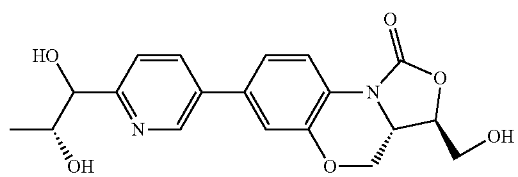 |
| 19 | 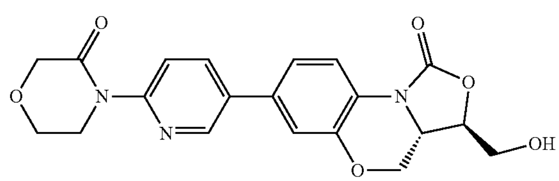 |
| 20 | 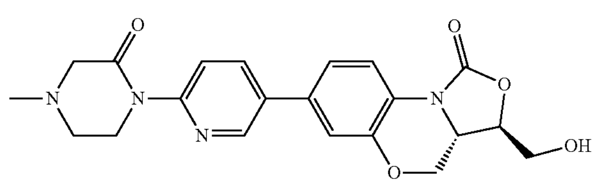 [SMILES: CN1CCN(c2ccc(-c3ccc4c(c3)OC[C@H]3[C@H](CO)OC(=O)N43)cn2)C(=O)C1] |
| 21 | 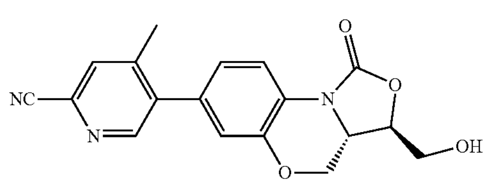 [SMILES: Cc1cc(C#N)ncc1-c1ccc2c(c1)OC[C@H]1[C@H](CO)OC(=O)N21] |
| 22 | 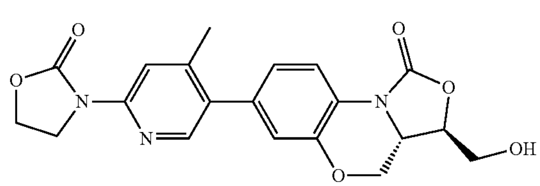 [SMILES: Cc1cc(N2CCOC2=O)ncc1-c1ccc2c(c1)OC[C@H]1[C@H](CO)OC(=O)N21] |

TABLE 1-continued

Representative Compounds

| Compound | Structure |
|---|---|
| 23 | 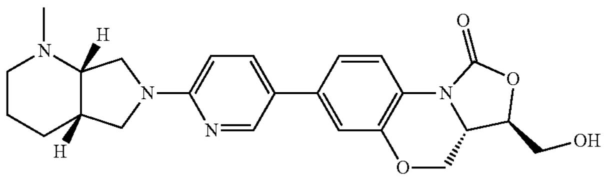 [SMILES: CN1CCC[C@H]2CN(c3ccc(-c4ccc5c(c4)OC[C@H]4[C@H](CO)OC(=O)N54)cn3)C[C@H]21] |
| 24 | 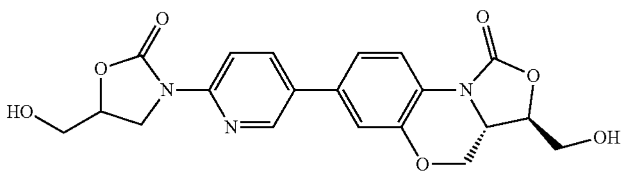 [SMILES: O=C1OC(CO)CN1c1ccc(-c2ccc3c(c2)OC[C@H]2[C@H](CO)OC(=O)N32)cn1] |
| 25 | 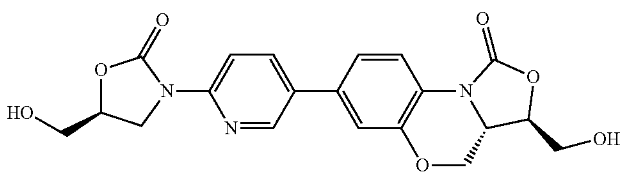 [SMILES: O=C1O[C@H](CO)CN1c1ccc(-c2ccc3c(c2)OC[C@H]2[C@H](CO)OC(=O)N32)cn1] |
| 26 | 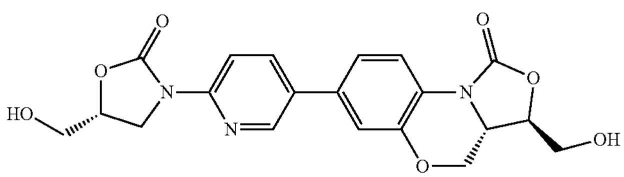 |
| 27 | 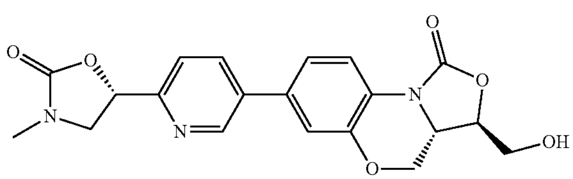 [SMILES: CN1C[C@@H](c2ccc(-c3ccc4c(c3)OC[C@H]3[C@H](CO)OC(=O)N43)cn2)OC1=O] |
| 28 | 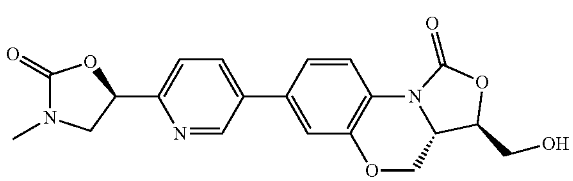 [SMILES: CN1C[C@H](c2ccc(-c3ccc4c(c3)OC[C@H]3[C@H](CO)OC(=O)N43)cn2)OC1=O] |
| 29 | 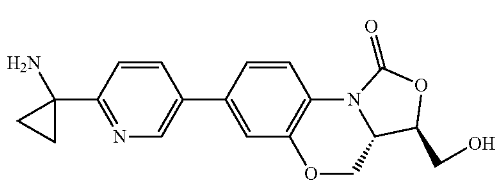 [SMILES: NC1(c2ccc(-c3ccc4c(c3)OC[C@H]3[C@H](CO)OC(=O)N43)cn2)CC1] |
| 30 | 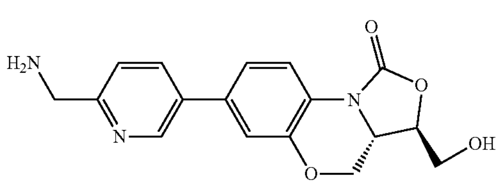 [SMILES: NCc1ccc(-c2ccc3c(c2)OC[C@H]2[C@H](CO)OC(=O)N32)cn1] |

TABLE 1-continued

Representative Compounds

| Compound | Structure |
| --- | --- |
| 31 | 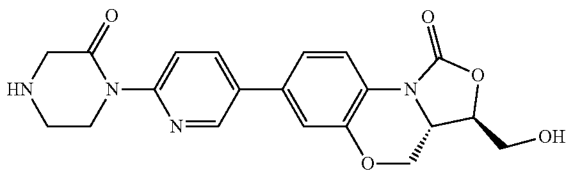 [SMILES: O=C1CNCCN1c1ccc(-c2ccc3c(c2)OC[C@H]2[C@H](CO)OC(=O)N32)cn1] |
| 32 | 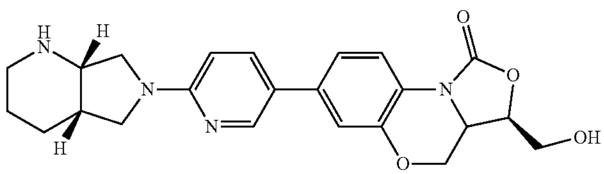 [SMILES: O=C1O[C@@H](CO)C2COc3cc(-c4ccc(N5C[C@@H]6CCCN[C@@H]6C5)nc4)ccc3N12] |
| 33 | 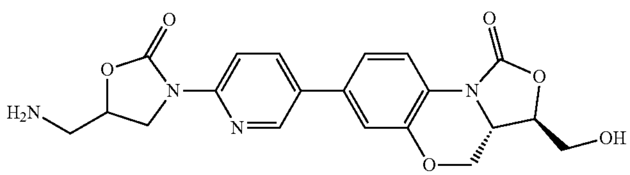 [SMILES: NCC1CN(c2ccc(-c3ccc4c(c3)OC[C@H]3[C@H](CO)OC(=O)N43)cn2)C(=O)O1] |
| 34 | 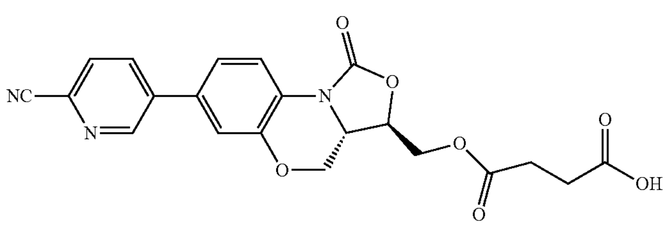 [SMILES: N#Cc1ccc(-c2ccc3c(c2)OC[C@H]2[C@H](COC(=O)CCC(=O)O)OC(=O)N32)cn1] |
| 35 | 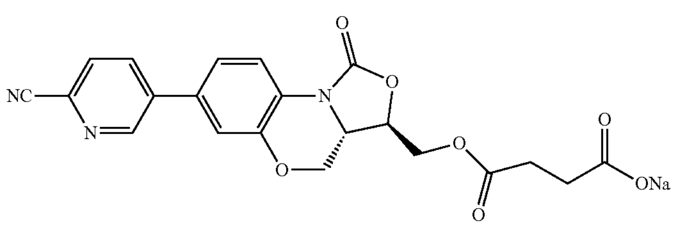 |
| 36 | 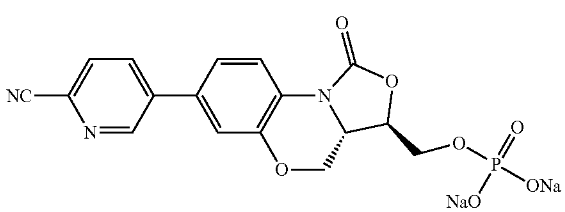 |
| 37 | 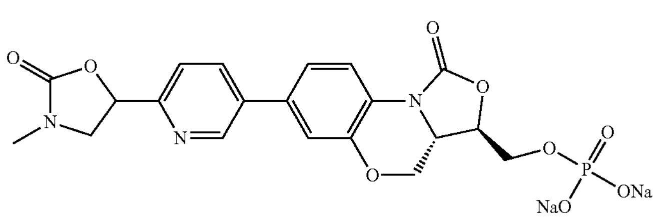 |

TABLE 1-continued

Representative Compounds

| Compound | Structure |
|---|---|
| 38 | 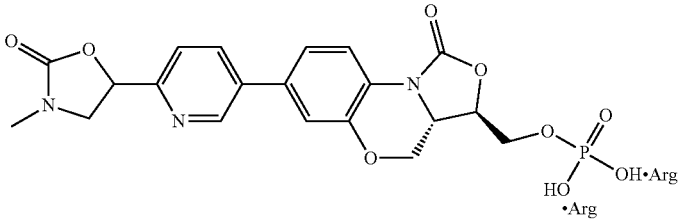 |
| 39 | 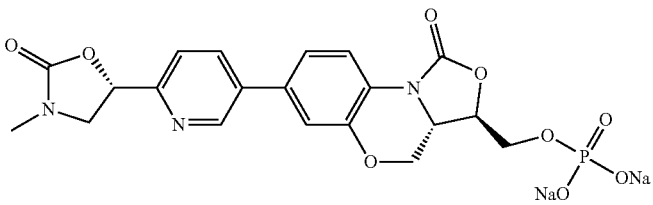 |
| 40 | 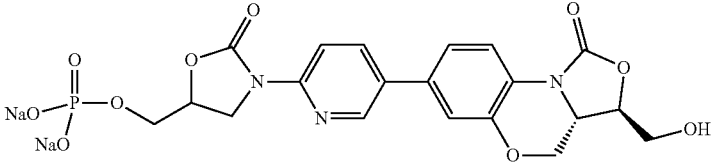 |
| 41 | 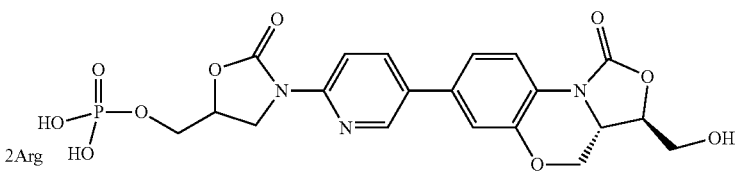 [SMILES: O=C1OC(COP(=O)(O)O)CN1c1ccc(-c2ccc3c(c2)OC[C@H]2[C@H](CO)OC(=O)N32)cn1] |

Methods for preparing the benzoxazine oxazolidinone compounds of general formula (I), an optical isomer thereof or a pharmaceutically acceptable salt thereof according to the present invention will now be specifically described below. These specific methods, however, do not constitute limitation to the present invention in any way. For example, reactants, solvents, bases, the amount of the compound used, the reaction temperature, the time needed for the reaction, etc. are not limited to the following illustrations. Optionally, the compounds of the invention can also be conveniently prepared by combining the various synthetic methods described in the present specification or known in the art. Such combinations can be readily carried out by those skilled in the art to which the present invention belongs.

In a preferred embodiment, the compounds I-2 and I-3 of the present invention can be prepared in accordance with the method shown in the equation Scheme I.

Scheme I

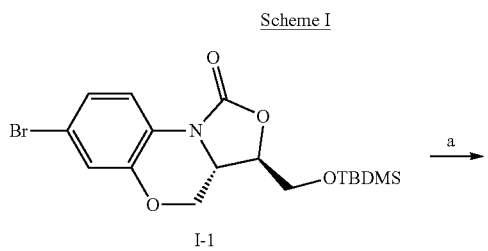

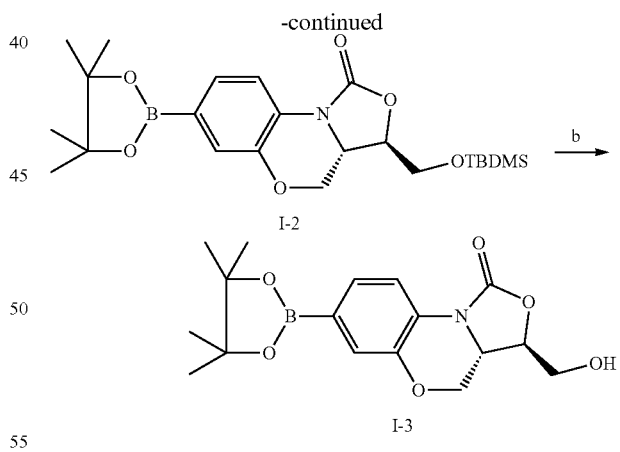

a) In a polar solvent under alkaline condition, compound I-1 (*J Med Chem* 2011, 54 (21), 7493-7502) and bis(pinacolato)diboron react with the catalysation by a palladium-containing catalyst in the presence of a phosphine-containing ligand under the protection of inert gas at a temperature from room temperature to 100° C. for 0.5-48 hrs, to give compound I-2:

said palladium-containing catalyst can be Pd(PPh$_3$)$_4$, Pd(dppf)Cl$_2$, Pd(dppf)Cl$_2$.CH$_2$Cl$_2$ or Pd(dba)$_2$; said phosphine-containing ligand can be 2-(Di-tert-butylphosphino) biphenyl; the alkali used for said alkaline condition can be potassium acetate (KOAc), sodium acetate (NaOAc), potassium tert-butoxide (ᵗBuOK) or sodium tert-butoxide (ᵗBuONa); said polar solvent can be dimethyl sulfoxide (DMSO), N,N-dimethyl formamide (DMF), 1,4-dioxane, tetrahydrofuran or toluene; said inner gas can be nitrogen or argon;

b) Compound I-2 reacts in a polar solvent in the presence of a fluorine-containing reagent at a temperature from 0° C. to room temperature for 1-6 hrs to remove the protecting group tert-butyldimethylsilyl (TBDMS), thereby producing compound I-3;

said fluorine-containing reagent can be tetra-n-butyl ammonium fluoride (ⁿBu₄NF); said polar solvent can be tetrahydrofuran or ethylene glycol dimethyl ether.

In a preferred embodiment, the benzoxazine oxazolidinone compound I-28 of general formula (I) according to the present invention can be prepared in accordance with the method shown in Scheme II.

room temperature to 120° C. for 2~48 hrs, to give the corresponding compound II-2;

said palladium-containing catalyst can be tetrakis(triphenylphosphine)palladium [Pd(PPh₃)₄], 1,1'-bis(diphenylphosphino)ferrocene palladium (II) dichloride [Pd(dppf)Cl₂], 1,1'-bis(diphenylphosphino)ferrocene-palladium (II) dichloride dichloromethane complex [Pd(dppf)Cl₂.CH₂Cl₂], tris(dibenzylideneacetone)dipalladium (0) [Pd₂(dba)₃] or bis(dibenzylideneacetone)palladium (0) [Pd(dba₂)], bis(triphenylphosphine)palladium(II) chloride [Pd(PPh₃)₂Cl₂] or palladium acetate [Pd(OAc)₂]; the alkali used for said alkaline condition can be cesium carbonate (Cs₂CO₃), potassium carbonate (K₂CO₃), sodium carbonate (Na₂CO₃), potassium phosphate (K₃PO₄) or potassium fluoride (KF); said polar solvent can be 1,4-dioxane (dioxane), tetrahydrofuran (THF), ethylene glycol dimethyl ether (DME), N,N-dimethyl forma- Scheme II

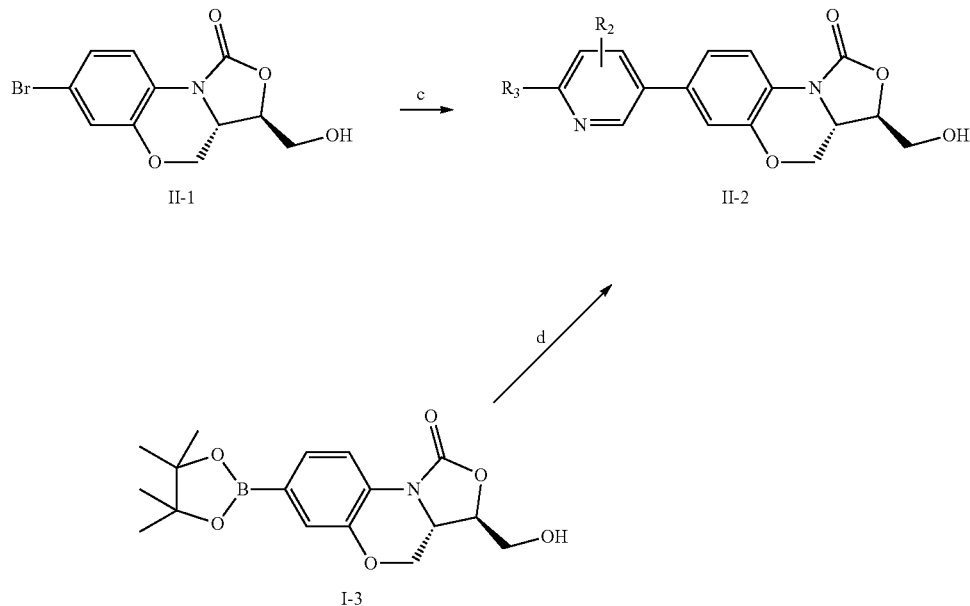

R₂ and R₃ are defined as above.

c) In a polar solvent under alkaline condition, compound II-1 (*J Med Chem* 2011, 54 (21), 7493-7502) and

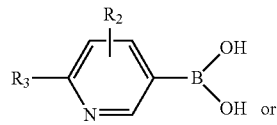

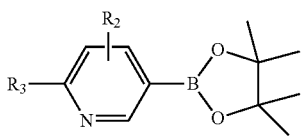

react, with the catalysation by a palladium-containing catalyst, under the protection of inert gas at a temperature from mide, ethanol or water or the mixtures thereof; said inner gas can be nitrogen or argon;

or d) In a polar solvent under alkaline condition, compound I-3 reacts with the halide

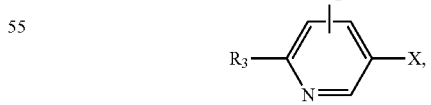

in the presence of a palladium-containing catalyst, under the protection of inert gas at a temperature from room temperature to 120° C. for 2~24 hrs, to give the corresponding compound II-2:

said palladium-containing catalyst can be Pd(PPh₃)₄, Pd(dppf)Cl₂.CH₂Cl₂, Pd(dppf)Cl₂, Pd(PPh₃)₂Cl₂ or Pd(OAc)₂; the alkali used for said alkaline condition can be Cs₂CO₃, K₂CO₃, K₃PO₄ or KF; said polar solvent can be- 1,4-dioxane, tetrahydrofuran, water, ethylene glycol dimethyl ether, ethanol, N,N-dimethyl formamide or toluene or the mixtures thereof; said inner gas can be nitrogen or argon.

In a preferred embodiment, the benzoxazine oxazolidinone compounds 29-33 of general formula (I) according to the present invention can be prepared in accordance with the method shown in Scheme III.

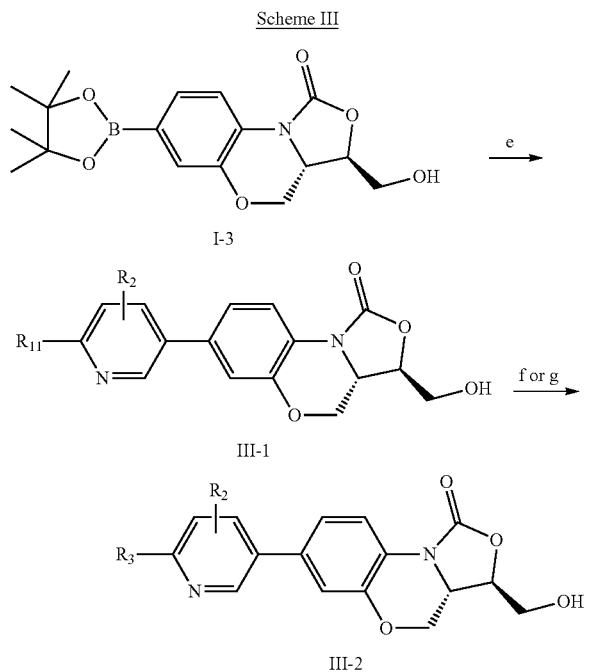

$R_{11}$ is

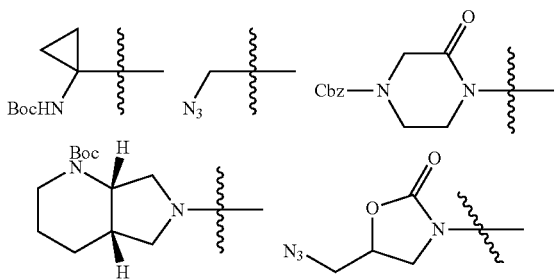

$R_3$ is

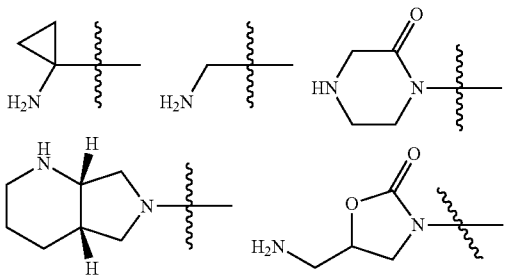

e) In a polar solvent under alkaline condition, compound I-3 reacts with the halide $R_{11}X$, in the presence of a palladium-containing catalyst, under the protection of inert gas at a temperature from room temperature to 120° C. for 2~24 hrs, to give the corresponding compound III-1:

wherein, X represents halogen; said palladium-containing catalyst can be $Pd(PPh_3)_4$, $Pd(dppf)Cl_2 \cdot CH_2Cl_2$, $Pd(dppf)Cl_2$, $Pd(PPh_3)_2Cl_2$ or $Pd(OAc)_2$; the alkali used for said alkaline condition can be $Cs_2CO_3$, $K_2CO_3$, $K_3PO_4$ or KF; said polar solvent can be 1,4-dioxane, tetrahydrofuran, water, ethylene glycol dimethyl ether, ethanol, N,N-dimethyl formamide or toluene or the mixtures thereof; said inner gas can be nitrogen or argon.

f) Under the circumstance that $R_{11}$ contains —$N_3$, compound III-1 is dissolved in a polar solvent, and subjected to catalytic hydrogenation in the presence of a metal catalyst to obtain compound III-2 with an $R_3$ containing —$NH_2$, or is reduced by a suitable reducing agent in a polar solvent to obtain compound III-2 containing —$NH_2$;

said polar solvent can be dichloromethane, methanol, ethanol, tetrahydrofuran, $H_2O$ or the mixtures thereof; the metal catalyst can be palladium/carbon or other metal catalysts containing palladium or nickel; the reducing agent can be sodium borohydride, lithium aluminium hydride, triphenyl phosphine or tributyl phosphine.

g) Under the circumstance that $R_{11}$ contains a Boc protecting group, the protecting group can be removed from compound III-1 in a polar solvent under acidic condition to obtain the corresponding compound III-2 without Boc protecting group;

said acid can be trifluoroacetic acid, hydrochloric acid (or its solution in 1,4-dioxane, ethyl acetate, methanol, etc.), and the like; said polar solvent can be dichloromethane, ethyl acetate, methanol, acetone, tetrahydrofuran, acetonitrile or the mixtures thereof.

In a preferred embodiment, the benzoxazine oxazolidinone compound of general formula (I) according to the present invention can be prepared in accordance with the method shown in Scheme IV.

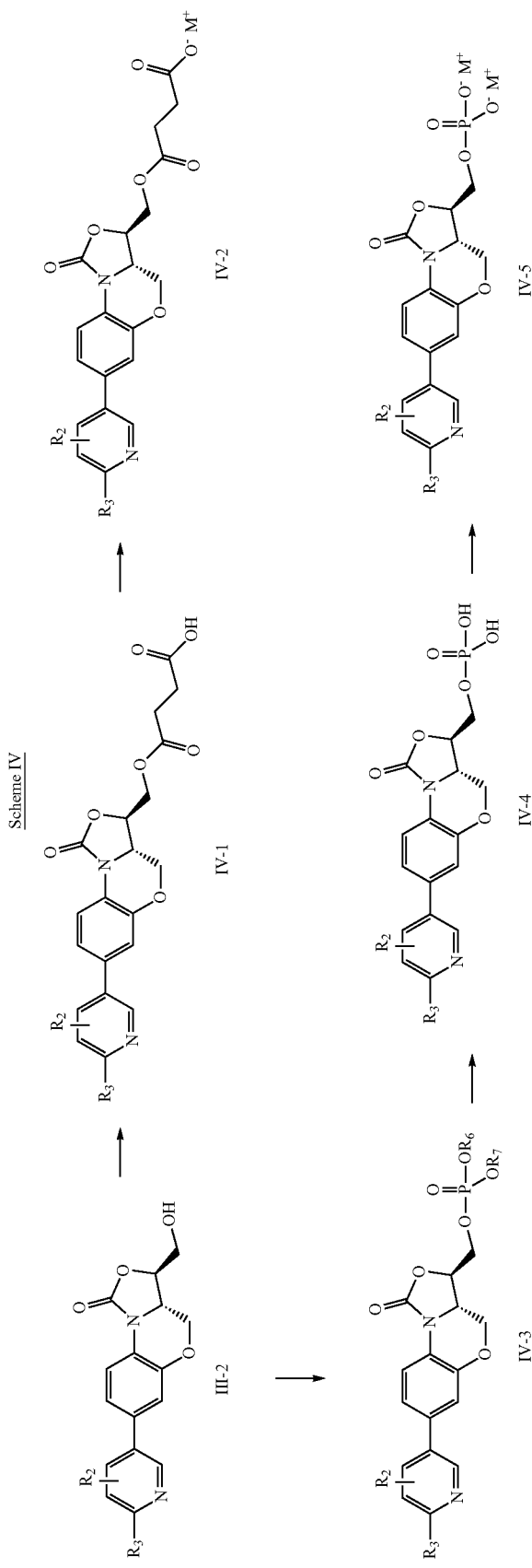

$R_2$, $R_3$, $R_6$, and $R_7$ are defined as above; M is metal or amino acid.

h) Compound III-2 reacts with succinic anhydride in a polar solvent in the presence of an alkali at a temperature of 0° C.~50° C. for 2~24 hrs to obtain the corresponding succinate monoester compound IV-1.

Said polar solvent can be dichloromethane, acetonitrile, tetrahydrofuran, N,N-dimethyl formamide or the mixtures thereof; said alkali can be triethylamine, DIPEA, pyridine or DMAP, and the like.

i) Compound IV-1 can react with an alkali in a polar solvent at a temperature from room temperature to 80° C. for 2~24 hrs to obtain the corresponding succinate monoester salt compound IV-2.

Said alkali can be sodium methoxide, sodium carbonate, sodium isooctoate, sodium hydroxide, calcium chloride, calcium acetate, magnesium chloride, magnesium hydroxide, magnesium acetate, arginine, lysine and the like; the polar solvent can be water, acetone, ethyl acetate, acetonitrile, N,N-dimethyl formamide, N,N-dimethyl acetamide, 1,4-dioxane, tetrahydrofuran and the like.

j) Compound III-2 reacts with a phosphite ester in the presence of an activating agent in a polar solvent under the protection of inner gas at a temperature of 0° C.~50° C. for 2~24 hrs to obtain the corresponding phosphite ester compound; the phosphite ester compound can react in the presence of an oxidizing agent in a polar solvent under the protection of inner gas at a temperature from −78° C. to room temperature for 1~24 hrs to obtain the corresponding phosphate ester compound IV-3.

Said phosphite ester can be tert-butyl phosphite, dibenzyl diisopropylamino phosphite and so on; the activating agent can be 4,5-dicyano imidazole, 1H-tetrazole and so on; the polar solvent can be dichloromethane, acetonitrile, tetrahydrofuran or the mixtures thereof; the inert gas can be nitrogen or argon. The oxidizing agent can be m-chloro-peroxybenzoic acid, tert-butyl hydroperoxide and so on.

k) The phosphate ester compound IV-3 can be subjected to catalytic hydrogenation in a polar solvent in the presence of a metal catalyst or react under acidic condition at a temperature from room temperature to 60° C. for 2~24 hrs to obtain the corresponding phosphate monoester compound IV-4.

Said polar solvent can be dichloromethane, methanol, ethanol, isopropanol, tetrahydrofuran, acetone, 1,4-dioxane, N,N-dimethyl formamide or the mixtures thereof; the metal catalyst can be palladium/carbon or other metal catalysts containing palladium or nickel; said acid can be trifluoroacetic acid, hydrochloric acid and so on.

o) The phosphate monoester compound IV-4 can react with an alkali in a polar solvent at a temperature from room temperature to 80° C. for 2~24 hrs to obtain the corresponding phosphate salt compound IV-5.

Said alkali can be sodium methoxide, sodium carbonate, sodium isooctoate, sodium hydroxide, calcium chloride, calcium acetate, magnesium chloride, magnesium hydroxide, magnesium acetate, arginine, lysine and so on; the polar solvent can be water, acetone, ethyl acetate, acetonitrile, N,N-dimethyl formamide, N,N-dimethyl acetamide, 1,4-dioxane, tetrahydrofuran and so on.

m) For compound II-2 with $R_3$ containing a hydroxyl, the phosphate monoester salt or amino acid ester salt thereof can be prepared following the above method.

EXAMPLES

The present invention is specifically illustrated in the following preparation examples and experimental examples. However, it should be understood that these preparation examples and experimental examples are to illustrate the present invention, but not to limit the scope of the present invention in any way.

In all the preparation examples and experimental examples, melting point was measured with an X-4 digital micro melting point determination instrument (Beijing Fukai Instrument Co., Ltd.), thermometer uncorrected; $^1$H-NMR was recorded by Varian Mercury 300 or Varian Mercury 400 NMR spectrometer, and chemical shift was shown in δ (ppm); silica gel was used for separation, and it was all 200-300 mesh unless stated otherwise. All the proportions of the elution fluid are volume ratio.

I. PREPARATION EXAMPLES

Example 1

(3R,3aS)-3-(((tert-butyldimethylsiloxy)oxy)methyl)-7-(4,4,5,5-tetramethyl-1,3,2-dioxaborolan-2-yl)-3a,4-dihydrobenzo[b]oxazolo[3,4-d][1,4]oxazin-1(3H)-one (I-2)

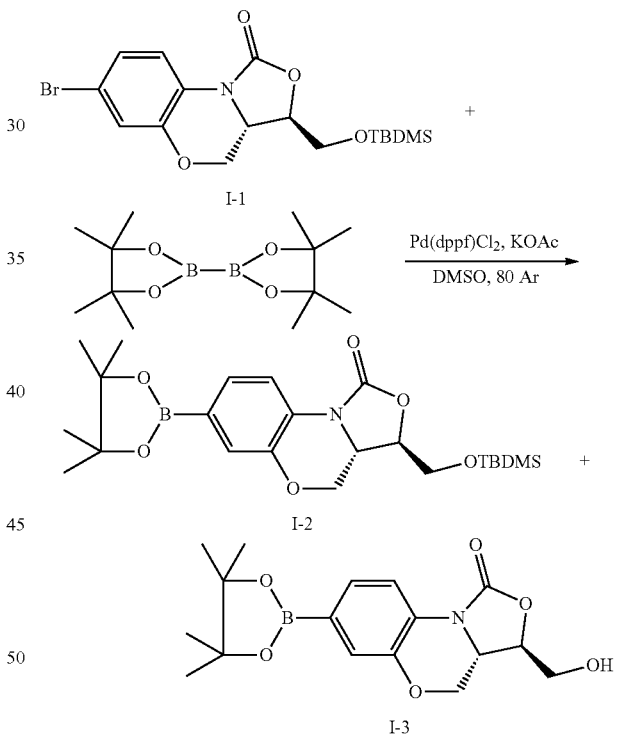

Compound I-1 (1 g, 2.4 mmol), bis(pinacolato)diboron (670 mg, 2.6 mmol) and potassium acetate (706 mg, 7.2 mmol) were added into DMSO (10 mL). The mixture was flushed with argon for 3 times, and PdCl$_2$(dppf)CH$_2$Cl$_2$ (97 mg, 0.12 mmol) was added. The mixture was flushed with argon again for 3 times, and then heated under protection of argon to 80° C. and reacted for 2 hrs. The reaction was monitored by TLC (petroleum ether/ethyl acetate=5/1). After the reaction completed, the mixture was cooled to room temperature, then diluted by adding ethyl acetate and water and filtered. The organic layer was separated and the aqueous phase was extracted with ethyl acetate (10 mL×2). The organic phase was combined, washed with saturated sodium chloride solution (20 mL), dried over anhydrous sodium sulfate, and then dried by rotary dryer. Column chromatography (petroleum ether/ethyl acetate=10/1) afforded 0.36 g of white solid (compound I-2), yield 32.4%; column chromatography (petroleum ether/ethyl acetate=2/1) afforded 0.33 g of white solid (compound I-3), yield 40%.

Compound I-2 m.p.: 85-87° C.

$^1$H NMR (300 MHz, CDCl$_3$): δ 7.86 (d, J=8.1 Hz, 1H), 7.28 (dd, J$_1$=8.1 Hz, J$_2$=1.3 Hz, 1H), 7.17 (d, J=1.2 Hz, 1H), 4.59-4.47 (m, 2H), 4.07-3.83 (m, 4H), 1.28 (s, 12H), 0.85 (s, 9H), 0.08 (s, 6H) 0.8 (d, J=9.15 Hz, 1H), 7.10-7.15 (m, 2H), 4.46 (dd, J$_1$=3.21 Hz, J$_2$=10.46 Hz, 1H), 4.24-4.30 (m, 1H), 4.05-4.18 (m, 1H), 3.84-3.96 (m, 3H), 0.90 (s, 9H), 0.07 (s, 6H).

MS (ESI) m/z: 462.3[M+1]$^+$.

Example 2

(3R,3aS)-3-(hydroxylmethyl)-7-(4,4,5,5-tetramethyl-1,3,2-dioxaborolan-2-yl)-3a,4-dihydrobenzo[b]oxazolo[3,4-d][1,4]oxazin-1(3H)-one (I-3)

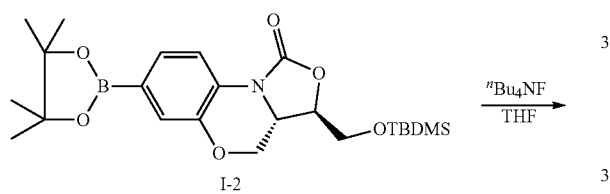

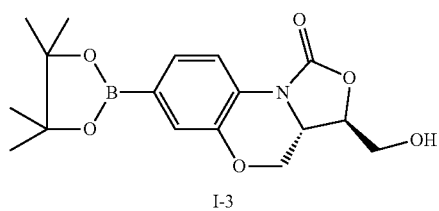

The starting material 1-2 (mmol) was dissolved in tetrahydrofuran (350 mL) and cooled on ice-salts cooling bath. Under protection by N$_2$, $^n$Bu$_4$NF solution was added dropwise (144.8 mL, 145 mmol, 1 M solution in tetrahydrofuran), and upon its completion, the mixture was maintained at low temperature (lower than 0° C.) and agitated for 3 hrs. The reaction was monitored by TLC (petroleum ether/ethyl acetate=5/1). After the reaction completed, the reaction was stopped, and tetrahydrofuran was evaporated. The reaction mixture was diluted with ethyl acetate (350 mL), washed with water and then saturated sodium chloride solution, dried over anhydrous sodium sulfate, and then dried by rotary dryer, to afford 18 g of white solid (I-3), yield 82%.

m.p.: 189-191° C.

$^1$H-NMR (300 MHz, DMSO) δ 7.91 (d, J=8.1 Hz, 1H), 7.28 (dd, J$_1$=8.1, J$_2$=1.3 Hz, 1H), 7.17 (d, J=1.3 Hz, 1H), 5.31 (t, J=5.7 Hz, 1H), 4.57-4.51 (m, 1H), 4.50-4.41 (m, 1H), 4.09-3.96 (m, 2H), 3.80-3.62 (m, 2H), 1.28 (s, 12H).

MS (ESI) m/z: 348.3 [M+1]$^+$.

Example 3

(3R,3aS)-3-(hydroxylmethyl)-7-(6-((R)-2-hydroxylpropionyl)pyridin-3-yl)-3a,4-dihydrobenzo[b]oxazolo[3,4-d][1,4]oxazin-1(3H)-one (I)

Step 1: Preparation of (2R)-1-(5-bromopyridin-2-yl)-2-((tetrahydro-2H-pyran-2-yl)oxy)propan-1-one (1a)

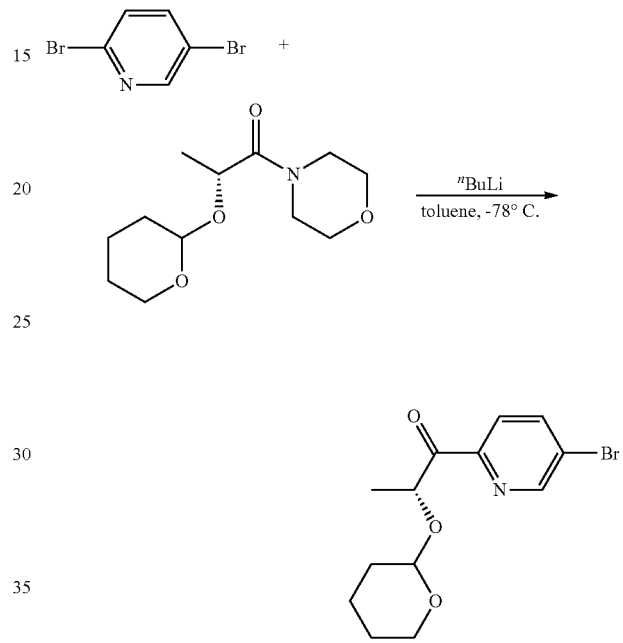

2,5-dibromopyridine (5 g, 21.1 mmol) was dissolved in dried toluene (100 mL), cooled to −78° C., to which n-butyl lithium (9 mL, 22.5 mmol, 2.5 M solution in n-hexane) was added dropwise. The mixture was allowed to react at −78° C. for 2 hrs, and then the solution of (2R)-1-morpholino-2-((tetrahydro-2H-pyran-2-yl)oxy)propan-1-one (7.7 g, 31.6 mmol) in toluene was added dropwise and allowed to react at −78° C. for 5 hrs. The reaction was monitored by TLC (petroleum ether). After the reaction completed, the reaction was quenched by adding saturated solution of ammonium chloride. The mixture was raised to room temperature and diluted with water. The toluene layer was separated and extracted with ethyl acetate. The organic phase was combined, washed with saturated sodium chloride solution, dried over anhydrous sodium sulfate, and then dried by rotary dryer. Column chromatography (petroleum ether) afforded 4.1 g of pale yellow solid (compound 1a), yield 62%.

$^1$H NMR (300 MHz, CDCl3) δ 8.99 (d, J=2.4 Hz, 1H), 8.11 (dd, J$_1$=−8.21 Hz, J$_2$=2.4 Hz, 1H), 7.56 (d, J=8.2 Hz, 1H), 4.94 (q, J=7.01 Hz, 1H), 4.53 (t, J=3.4 Hz, 1H), 3.90-3.75 (m, 1H), 3.53-3.38 (m, 1H), 1.71-1.35 (m, 9H).

MS (EI) m/z: 314 (M$^+$).

Step 2: Preparation of (R)-1-(5-bromopyridin-2-yl)-2-hydroxylpropan-1-one (1b)

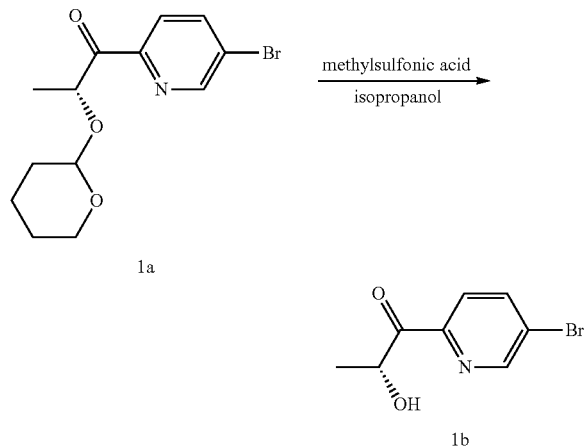

Compound 1a (4.0 g, 12.7 mmol) was dissolved in isopropanol (50 mL), and methylsulfonic acid (1.8 g, 18.5 mmol) was added. The reaction was agitated at room temperature for 5 hrs. The reaction was monitored by TLC (petroleum ether/ethyl acetate=5/1). After the reaction completed, the solvent and excess methylsulfonic acid was removed by evaporation. The mixture was then diluted with water. The pH value was adjusted to 7-8 with saturated $NaHCO_3$ solution. The mixture was extracted by ethyl acetate (30 mL×2). The organic phase was combined, washed with saturated sodium chloride solution, dried over anhydrous sodium sulfate, and then dried by rotary dryer. Column chromatography (petroleum ether/ethyl acetate=7/1) afforded 1.6 g of white solid (compound 1b), yield 55%.

m.p.: 242-244° C.

$^1$H NMR (300 MHz, CDCl3) δ 8.74 (d, J=1.8 Hz, 1H), 8.05-7.95 (m, 2H), 5.33 (q, J=6.9 Hz, 1H), 3.76 (bs, 1H), 1.51 (d, J=6.9 Hz, 3H).

MS (EI) m/z: 230 (M$^+$).

Step 3: Preparation of (3R,3aS)-3-(hydroxylmethyl)-7-(6-((R)-2-hydroxylpropionyl)pyridine-3-yl)-3a,4-dihydrobenzo[b]oxazolo[3,4-d][1,4]oxazin-1(3H)-one (I)

Compound I-3 (100 mg, 0.29 mmol) was dissolved in 1,4-dioxane/$H_2O$ (V/V=10/1) mixed solvent, to which 1b (102 mg, 0.44 mmol) and cesium carbonate (234 mg, 0.72 mmol) were added. The mixture was flushed with Ar for 2 times, then Pd(PPh$_3$)$_4$ (34 mg, 0.029 mmol) was added, followed by another flushing with Ar. Under the protection of Ar, the mixture was heated in oil bath to 80° C. and allowed to react overnight. The reaction was monitored by TLC. After compound I-3 completely reacted, the oil bath was removed and the reaction mixture was filtered. Column chromatography ($CH_2Cl_2$/MeOH=30:1) afforded 80 mg of white powdery solid (compound 1), yield 75%.

m.p.: 164-166° C.

$^1$H NMR (300 MHz, DMSO) δ 9.05 (d, J=1.9 Hz, 1H), 8.29 (dd, J$_1$=8.3 Hz, J$_2$=2.4 Hz, 1H), 8.05-7.99 (m, 2H), 5.42 (q, J=6.8 Hz, 1H), 4.65-4.56 (m, 1H), 4.54-4.45 (m, 1H), 4.15-4.04 (m, 2H), 3.80-3.65 (m, 2H), 1.36 (d, J=6.9 Hz, 3H).

MS (EI) m/z: 370 (M$^+$).

Example 4

(3R,3aS)-7-(6-((1H-1,2,4-triazol-1-yl)methyl)pyridin-3-yl)-3-(hydroxylmethyl)-3a,4-dihydrobenzo[b]oxazolo[3,4-d][1,4]oxazin-1(3H)-one (2)

Compound I-3 (100 mg, 0.29 mmol) was dissolved in the 1,4-dioxane/$H_2O$ (V/V=10/1) mixed solvent, to which were added 2-((1H-1,2,4-triazol-1-yl)methyl)-5-bromopyridine (105 mg, 0.44 mmol), cesium carbonate (234 mg, 0.72 mmol) and Pd(PPh$_3$)$_4$ (34 mg, 0.029 mmol). A procedure following the synthetic method of compound 1 afforded 74 mg of white solid (compound 2), yield 67%.

$^1$H NMR (300 MHz, DMSO) δ 8.82 (d, J=1.8 Hz, 1H), 8.71 (s, 1H), 8.08 (dd, J$_1$=8.2 Hz, J$_2$=2.4 Hz, 1H), 8.00-7.94 (m, 2H), 7.40-7.36 (m, 2H), 7.35 (d, J=8.2 Hz, 1H), 5.59 (s, 2H), 4.64-4.51 (m, 1H), 4.47-4.42 (m, 1H), 4.12-4.05 (m, 2H), 3.81-3.65 (m, 2H).

MS (EI) m/z: 379M$^+$).

Example 5

5-((3R,3aS)-3-(hydroxylmethyl)-1-oxo-1,3,3a,4-tetrahydrobenzo[b]oxazolo[3,4-d][1,4]oxazin-7-yl)picolinonitrile (3)

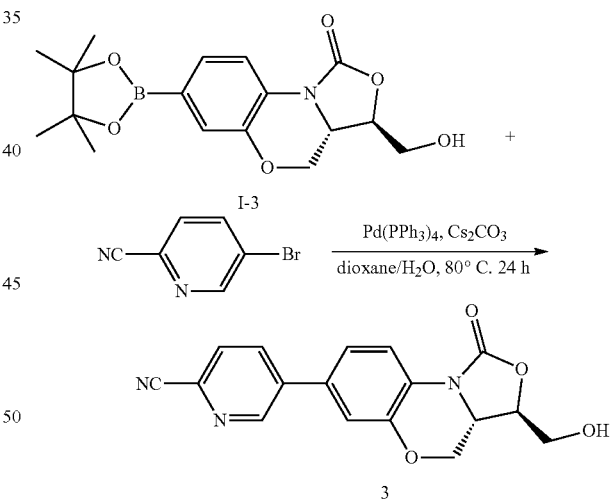

Compound I-3 (150 mg, 0.43 mmol) was dissolved in the 1,4-dioxane/$H_2O$ (v/v=10/1) mixed solvent, to which were added 2-cyano-5-bromopyridine (119 mg, 0.65 mmol) (Bioorg. Med. Chem., 12, 2004, 5909-5915), cesium carbonate (213 mg, 0.86 mmol) and Pd(PPh$_3$)$_4$ (41 mg, 0.043 mmol). A procedure following the synthetic method of compound 1 afforded 110 mg of white solid (compound 3), yield 79%.

$^1$H NMR (300 MHz, DMSO) δ 9.05 (d, J=2.0 Hz, 1H), 8.34 (dd, J$_1$=8.2 Hz, J$_2$=2.3 Hz, 1H), 8.10 (d, J=8.2 Hz, 1H), 8.02 (d, J=9.0 Hz, 1H), 7.55-7.47 (m, 2H), 4.65-4.56 (m, 1H), 4.50-4.45 (m, 1H), 4.15-4.05 (m, 2H), 3.81-3.65 (m, 2H).

MS (EI) m/z: 323 (M$^+$).

Example 6

(3R,3aS)-7-(6-(1,2-dihydroxylethyl)pyridin-3-yl)-3-(hydroxylmethyl)-3a,4-dihydrobenzo[b]oxazolo[3,4-d][1,4]oxazin-1(3H)-one (4)

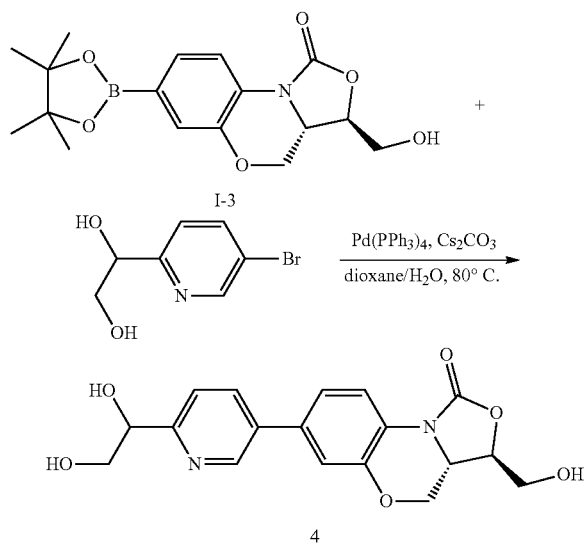

Compound I-3 (150 mg, 0.43 mmol) was dissolved in the 1,4-dioxane/H₂O (V/V=10/1) mixed solvent, to which were added 1-(5-bromopyridin-2-yl)ethane-1,2-diol (140 mg, 0.65 mmol), cesium carbonate (213 mg, 0.86 mmol) and Pd(PPh₃)₄ (41 mg, 0.043 mmol). A procedure following the synthetic method of compound 1 afforded 60 mg of white solid (compound 4), yield 39%.

m.p.: 150-152° C.

¹H NMR (300 MHz, DMSO) δ 8.79 (d, J=1.8 Hz, 1H), 8.04 (dd, J₁=8.1 Hz, J₂=2.2 Hz, 1H), 7.95 (d, J=9.1 Hz, 1H), 7.54 (d, J=8.4 Hz, 1H), 7.40-7.34 (m, 2H), 4.65-4.51 (m, 2H), 4.50-4.43 (m, 1H), 4.12-4.03 (m, 2H), 3.80-3.65 (m, 3H), 3.55-3.44 (dd, J₁=11.1 Hz, J₂=6.9 Hz, 1H).

MS (ESI) m/z: 359.0 [M+1]⁺.

Example 7

(3R,3aS)-3-(hydroxylmethyl)-7-(6-(2-oxazolidino-3-yl)pyridin-3-yl)-3a,4-dihydrobenzo[b]oxazolo[3,4-d][1,4]oxazin-1(3H)-one (5)

Compound I-3 (100 mg, 0.28 mmol), 3-(5-bromopyridin-2-yl)oxazolidin-2-one (102 mg, 0.42 mmol) (*J Med Chem*, 2011, 54 (21), 7493-7502), cesium carbonate (228 mg, 0.70 mmol) and Pd(PPh₃)₄ (32 mg, 0.028 mmol), under the protection of argon, reacted following the synthetic method of compound 1 to afford 58 mg of white solid (compound 5), yield 52%.

¹H NMR (400 MHz, DMSO) δ 8.69 (s, 1H), 8.14 (s, 2H), 8.03-7.92 (m, 2H), 7.76 (s, 1H), 7.47-7.28 (m, 2H), 4.84 (d, J=7.2 Hz, 1H), 4.58 (dd, J=10.3, 3.0 Hz, 1H), 4.48 (t, J=8.1 Hz, 2H), 4.28-4.12 (m, 4H).

MS (EI) m/z: 396 (M⁺).

Example 8

(3R,3aS)-7-(6-(cyclopropyl(hydroxyl)methyl)pyridin-3-yl)-3-(hydroxyl-methyl)-3a,4-dihydrobenzo[b]oxazolo[3,4-d][1,4]oxazin-1(3H)-one (6)

Compound I-3 (150 mg, 0.43 mmol) was dissolved in the 1,4-dioxane/H₂O (V/V=10/1) mixed solvent, to which were added (5-bromopyridin-2-yl)(cyclopropyl)methanol (148 mg, 0.65 mmol), cesium carbonate (213 mg, 0.86 mmol) and Pd(PPh₃)₄ (41 mg, 0.043 mmol). A procedure following the synthetic method of compound 1 afforded 78 mg of white solid (compound 6), yield 49%.

¹H NMR (300 MHz, DMSO) δ 9.05 (d, J=2.0 Hz, 1H), 8.34 (dd, J₁=8.2 Hz, J₂=2.3 Hz, 1H), 8.10 (d, J=8.2 Hz, 1H), 8.02 (d, J=9.0 Hz, 1H), 7.55-7.47 (m, 2H), 4.65-4.56 (m, 1H), 4.50-4.45 (m, 1H), 4.49 (m, 1S), 4.15-4.05 (m, 2H), 3.81-3.65 (m, 2H), 0.68 (m, 1H), 0.25 (m, 4H)

Example 9

(3R,3aS)-3-(hydroxylmethyl)-7-(6-(2-hydroxylpropyl-2-yl)pyridin-3-yl)-3a,4-dihydrobenzo[b]oxazolo[3,4-d][1,4]oxazin-1(3H)-one (7)

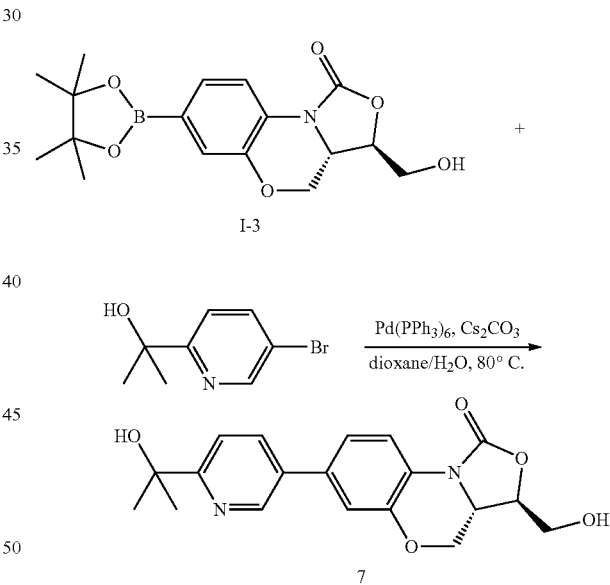

Compound I-3 (150 mg, 0.43 mmol) was dissolved in the 1,4-dioxane/H₂O (V/V=10/1) mixed solvent, to which were added 2-(2-hydroxylpropan-2-yl)-5-bromopyridine (140 mg, 0.65 mmol), cesium carbonate (213 mg, 0.86 mmol) and Pd(PPh₃)₄ (41 mg, 0.043 mmol). A procedure following the method of Example 1 afforded 116 mg of white solid (compound 7), yield 76%.

¹H NMR (400 MHz, DMSO) δ 8.77 (d, J=2.3 Hz, 1H), 8.03 (dd, J=8.3, 2.4 Hz, 1H), 7.98-7.93 (m, 1H), 7.70 (d, J=8.3 Hz, 1H), 7.40-7.33 (m, 2H), 5.33 (t, J=5.7 Hz, 1H), 5.25 (s, 1H), 4.64-4.52 (m, 1H), 4.47 (dd, J=6.6, 3.1 Hz, 1H), 4.13-4.02 (m, 2H), 3.83-3.74 (m, 1H), 3.74-3.66 (m, 1H), 1.46 (s, 6H).

MS (EI) m/z: 356 (M⁺).

Example 10

(3R,3aS)-7-(6-(1-hydroxylethyl)pyridin-3-yl)-3-(hydroxylmethyl)-3a,4-dihydrobenzo[b]oxazolo[3,4-d][1,4]oxazin-1(3H)-one (8)

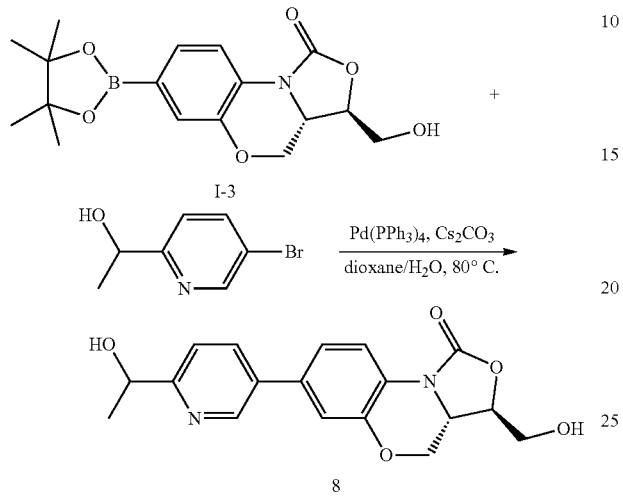

Compound I-3 (150 mg, 0.43 mmol) was dissolved in the 1,4-dioxane/H₂O (V/V=10/1) mixed solvent, to which were added 1-(5-bromopyridin-2-yl)ethano (131 mg, 0.65 mmol), cesium carbonate (213 mg, 0.86 mmol) and Pd(PPh₃)₄ (41 mg, 0.043 mmol). A procedure following the synthetic method of compound 1 afforded 106 mg of white solid (compound 8), yield 72%.

¹H NMR (300 MHz, DMSO) δ 8.76 (d, J=1.8 Hz, 1H), 8.04 (dd, J=8.2, 2.4 Hz, 1H), 7.99-7.93 (m, 1H), 7.55 (d, J=8.2 Hz, 1H), 7.39-7.33 (m, 2H), 5.39 (d, J=4.7 Hz, 1H), 5.33 (t, J=5.7 Hz, 1H), 4.81-4.71 (m, 1H), 4.63-4.53 (m, 1H), 4.51-4.44 (m, 1H), 4.13-4.02 (m, 2H), 3.82-3.65 (m, 2H), 1.39 (d, J=6.5 Hz, 3H).

MS (EI) m/z: 342 (M⁺).

Example 11

(3R,3aS)-3-(hydroxylmethyl)-7-(6-(hydroxylmethyl)pyridin-3-yl)-3a,4-dihydrobenzo[b]oxazolo[3,4-d][1,4]oxazin-1(3H)-one (9)

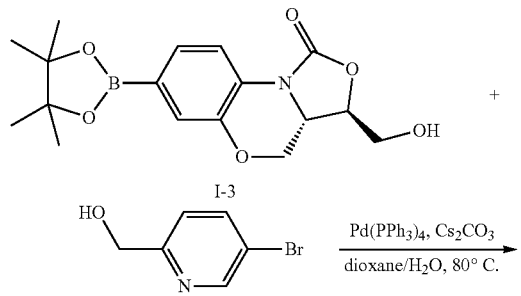

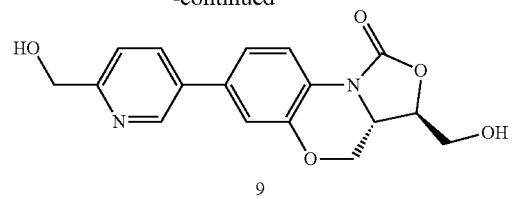

Compound I-3 (150 mg, 0.43 mmol) was dissolved in the 1,4-dioxane/H₂O (V/V=10/1) mixed solvent, to which were added (5-bromopyridin-2-yl)methanol (122 mg, 0.65 mmol), cesium carbonate (213 mg, 0.86 mmol) and Pd(PPh₃)₄ (41 mg, 0.043 mmol). A procedure following the synthetic method of compound 1 afforded 95 mg of white powdery solid (compound 9), yield 67%.

¹H NMR (300 MHz, DMSO) δ 8.79 (d, J=2.14 Hz, 1H), 8.07 (dd, J₁=8.25 Hz, J₂=2.44 Hz, 1H), 7.98 (d, J=8.86 Hz, 1H), 7.51 (d, J=8.86 Hz, 1H), 7.40-7.35 (m, 2H), 5.32 (s, 1H), 4.65-4.52 (m, 3H), 4.50-4.45 (m, 1H), 4.12-4.03 (m, 2H), 3.81-3.65 (m, 2H).

MS (EI) m/z: 328 (M⁺).

Example 12

(3R,3aS)-7-(6-(1-hydroxylcyclopentyl)pyridin-3-yl)-3-(hydroxylmethyl)-3a,4-dihydrobenzo[b]oxazolo[3,4-d][1,4]oxazin-1(3H)-one (10)

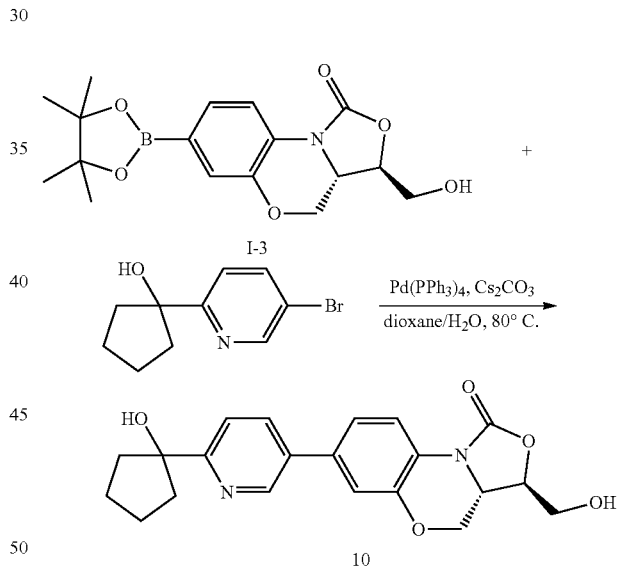

Compound I-3 (150 mg, 0.43 mmol) was dissolved in the 1,4-dioxane/H₂O (V/V=10/1) mixed solvent, to which were added 1-(5-bromopyridin-2-yl)cyclopentanol (157 mg, 0.65 mmol), cesium carbonate (213 mg, 0.86 mmol) and Pd(PPh₃)₄ (41 mg, 0.043 mmol). A procedure following the synthetic method of compound 1 afforded 128 mg of white powdery solid (compound 10), yield 78%.

¹H NMR (400 MHz, DMSO) δ 8.78 (d, J=1.8 Hz, 1H), 8.02 (dd, J=8.3, 2.4 Hz, 1H), 7.96 (d, J=8.9 Hz, 1H), 7.73 (d, J=8.2 Hz, 1H), 7.62 (dd, J=11.8, 7.0 Hz, 1H), 7.58-7.52 (m, 1H), 7.39-7.33 (m, 2H), 5.34 (t, J=5.6 Hz, 1H), 5.09 (s, 1H), 4.63-4.54 (m, 1H), 4.47 (dt, J=7.2, 3.8 Hz, 1H), 4.13-4.01 (m, 2H), 3.82-3.74 (m, 1H), 3.73-3.66 (m, 1H), 2.17-2.06 (m, 2H), 1.88 (d, J=4.6 Hz, 2H), 1.77 (dd, J=11.4, 6.7 Hz, 4H).

MS (EI) m/z: 382 (M⁺).

Example 13

(3R,3aS)-3-(hydroxylmethyl)-7-(6-(4-hydroxylpiperidin-1-yl)pyridin-3-yl)-3a,4-dihydrobenzo[b]oxazolo[3,4-d][1,4]oxazin-1(3H)-one (11)

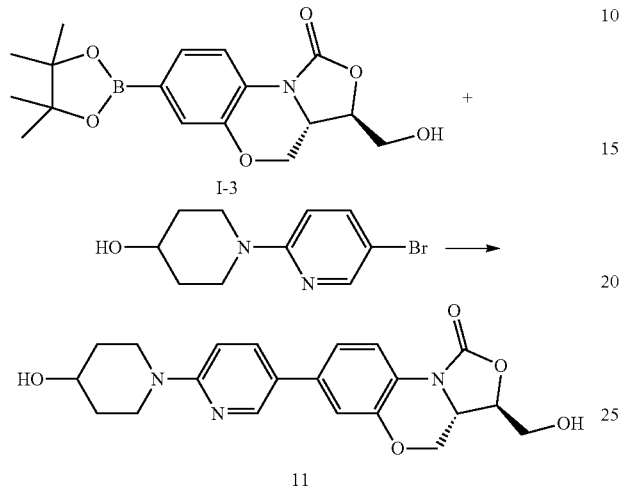

Compound I-3 (100 mg, 0.29 mmol), 1-(5-bromopyridin-2-yl)piperidin-4-ol (113 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 62 mg of white solid (compound 11), yield 54%.

m.p.: >198° C.

$^1$H NMR (400 MHz, DMSO) δ 8.41 (d, J=2.5 Hz, 1H), 7.88 (d, J=8.4 Hz, 1H), 7.79 (dd, J=8.9, 2.6 Hz, 1H), 7.32-7.17 (m, 2H), 6.89 (d, J=9.0 Hz, 1H), 5.32 (t, J=5.7 Hz, 1H), 4.70 (d, J=4.3 Hz, 1H), 4.59-4.51 (m, 1H), 4.49-4.42 (m, 1H), 4.09-3.99 (m, 4H), 4.05-4.00 (m, 3H), 3.79-3.65 (m, 3H), 3.16-3.07 (m, 2H), 1.82-1.73 (m, 2H), 1.40-1.30 (m, 2H).

MS (EI) m/z: 397 (M$^+$).

Example 14

(3R,3aS)-3-(hydroxylmethyl)7-(6-(4-methylpiperazin-1-yl)pyridin-3-yl)-3a,4-dihydrobenzo[b]oxazolo[3,4-d][1,4]oxazin-1(3H)-one (12)

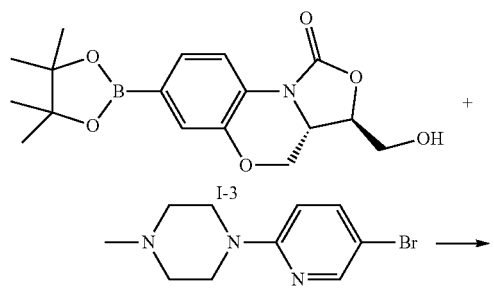

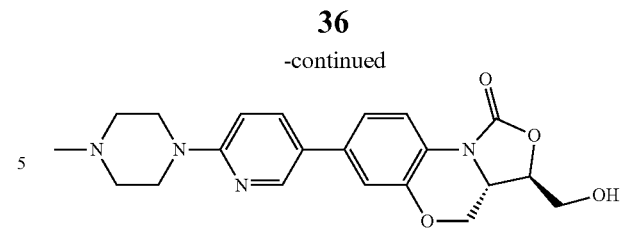

Compound I-3 (100 mg, 0.29 mmol), 2-(4-methylpiperazin-1-yl)-5-bromopyridine (112 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 75 mg of white solid (compound 12), yield 65%.

$^1$H NMR (400 MHz, CD$_3$OD) δ 8.42 (d, J=2.4 Hz, 1H), 7.89 (d, J=8.4 Hz, 1H), 7.82 (dd, J=8.9, 2.5 Hz, 1H), 7.31-7.20 (m, 2H), 6.89 (d, J=8.9 Hz, 1H), 5.32 (t, J=5.6 Hz, 1H), 4.62-4.51 (m, 1H), 4.49-4.42 (m, 1H), 4.10-3.99 (m, 2H), 3.82-3.65 (m, 2H), 3.52 (t, J=3.0 Hz, 4H), 2.40 (t, J=3.0 Hz, 4H), 2.22 (s, 3H).

MS (EI) m/z: 396 (M$^+$).

Example 15

(3R,3aS)-7-(6-acetylpyridin-3-yl)-3-(hydroxylmethyl)-3a,4-dihydrobenzo[b]oxazolo[3,4-d][1,4]oxazin-1(3H)-one (13)

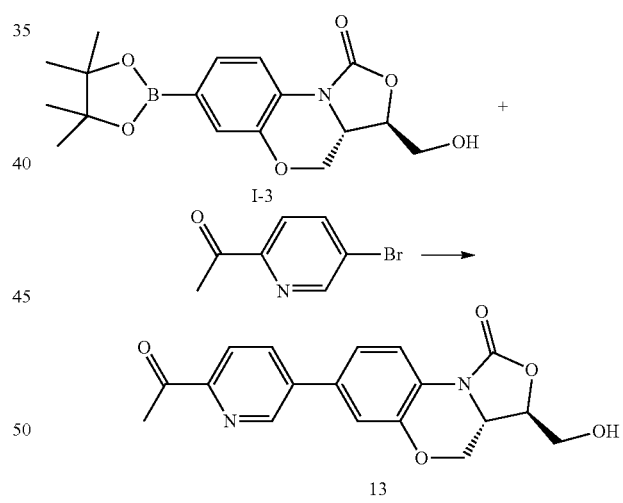

Compound I-3 (100 mg, 0.29 mmol), 2-acetyl-5-bromopyridine (88 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 72 mg of white solid (compound 13), yield 72%.

m.p.: 199-201° C.

$^1$H NMR (300 MHz, DMSO) δ 9.05 (d, J=2.2 Hz, 1H), 8.27 (dd, J=8.2, 2.3 Hz, 1H), 8.05-7.96 (m, 2H), 7.54-7.44 (m, 2H), 5.34 (t, J=5.7 Hz, 1H), 4.65-4.55 (m, 1H), 4.52-4.46 (m, 1H), 4.15-4.04 (m, 2H), 3.83-3.65 (m, 2H), 2.51 (s, 3H).

MS (ESI) m/z: 341.5[M+1]$^+$.

Example 16

(3R,3aS)-3-(hydroxymethyl)-7-(6-(3-methyl-2-oxazolidin-5-yl)pyridin-3-yl)-3a,4-dihydrobenzo[b]oxazolo[3,4-d][1,4]oxazin-1(3H)-one (14)

Step 1: Preparation of tert-butyl(2-(5-bromopyridin-2-yl)-2-hydroxylethyl)amide (14a)

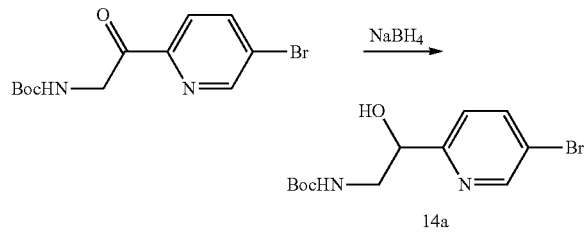

Tert-butyl(2-(5-bromopyridin-2-yl)-2-oxoethyl)amide (830 mg, 2.63 mmol) was dissolved in dried methanol (10 mL). NaBH₄ (150 mg, 3.95 mmol) was added. The resulting mixture was allowed to react overnight at room temperature. The reaction was monitored by TLC (petroleum ether/ethyl acetate=5/1). After the reaction completed, water was added, and the mixture was extracted with ethyl acetate. The organic phase was combined, washed with saturated sodium chloride solution, dried over anhydrous sodium sulfate. Column chromatography (petroleum ether/ethyl acetate=8/1) afforded 512 mg of white solid (compound 14a), yield 61%.

m.p.: 112-113° C.

$^1$H NMR (400 MHz, DMSO) δ 8.60 (d, J=2.2 Hz, 1H), 8.02 (dd, J=8.4, 2.3 Hz, 1H), 7.43 (d, J=8.4 Hz, 1H), 6.74 (t, J=5.8 Hz, 1H), 5.63 (d, J=5.1 Hz, 1H), 4.57 (dt, J=7.0, 5.0 Hz, 1H), 3.34-3.28 (m, 1H), 3.10-3.02 (m, 1H), 1.33 (s, 9H).

MS (ESI) m/z: 318.4 [M+1]⁺.

Step 2: Preparation of 5-(5-bromopyridin-2-yl)oxazolidin-2-one (14b)

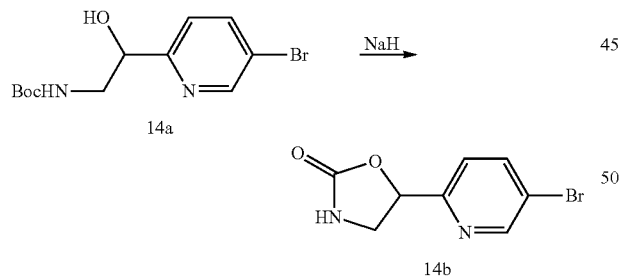

Compound 14a (70 mg, 0.85 mmol) was dissolved in dried tetrahydrofuran (5 mL), cooled to 0° C. NaH (51 mg, 1.28 mmol) was added, and after its completion, the reaction mixture was raised to room temperature, and then raised to 50° C. to react for 4 hrs. The reaction was monitored by TLC (petroleum ether/ethyl acetate=8/1). After the reaction completed, water was added, and the mixture was extracted with ethyl acetate. The organic phase was combined, washed with saturated sodium chloride solution, dried over anhydrous sodium sulfate. Column chromatography (petroleum ether/ethyl acetate=5/1) afforded 150 mg of white solid (compound 14b), yield 72%.

m.p.: 120-121° C.

$^1$H NMR (300 MHz, DMSO) δ 8.75 (d, J=1.6 Hz, 1H), 8.13 (dd, J=8.3, 2.4 Hz, 1H), 7.75 (s, 1H), 7.46 (d, J=8.4 Hz, 1H), 5.63 (dd, J=9.0, 6.1 Hz, 1H), 3.88 (dd, J=9.0, 8.8 Hz, 1H), 3.53 (dd, J=8.8, 6.2 Hz, 1H).

MS (EI) m/z: 243 (M⁺).

Step 3: Preparation of 5-(5-bromopyridin-2-yl)-3-methyloxazolidin-2-one (14c)

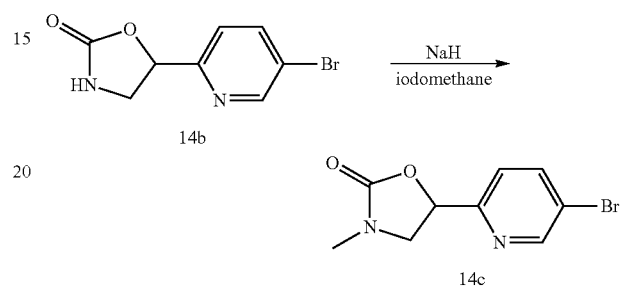

Compound 14b (350 mg, 1.44 mmol) was dissolved in dried tetrahydrofuran, cooled to 0° C. NaH (86.4 mg, 2.16 mmol) was added, and iodomethane (0.18 mL, 2.88 mmol) was added dropwise. After the addition was completed, the reaction mixture was raised to room temperature for reacting overnight. The reaction was monitored by TLC (petroleum ether/ethyl acetate=5/1). After the reaction completed, the mixture was diluted with water, and extracted with ethyl acetate. The organic phase was combined, washed with saturated sodium chloride solution, dried over anhydrous sodium sulfate. Column chromatography (petroleum ether/ethyl acetate=8/1) afforded 315 mg of white solid (compound 14c), yield 85%.

m.p.: 61-63° C.

$^1$H NMR (300 MHz, DMSO) δ 8.76 (d, J=2.1 Hz, 1H), 8.14 (dd, J=8.4, 2.4 Hz, 1H), 7.47 (d, J=8.4 Hz, 1H), 5.58 (dd, J=9.0, 6.1 Hz, 1H), 3.94 (t, J=8.9 Hz, 1H), 3.62 (dd, J=8.8, 6.2 Hz, 1H), 2.78 (s, 3H).

MS (EI) m/z: 256 (M⁺).

Step 4: Preparation of (3R,3aS)-3-(hydroxymethyl)-7-(6-(3-methyl-2-oxazolidin-5-yl)pyridin-3-yl)-3a,4-dihydrobenzo[b]oxazolo[3,4-d][1,4]oxazin-1(3H)-one (18)

Compound I-3 (100 mg, 0.29 mmol), 14c (113 mg, 0.44 mmol), cesium carbonate (234 mg, 0.72 mmol) and Pd(PPh₃)₄ (34 mg, 0.029 mmol), under the protection of argon, reacted following the synthetic method of compound 1 to afford 75 mg of white solid (compound 14), yield 65%.

$^1$H NMR (300 MHz, DMSO) δ 8.93 (d, J=2.1 Hz, 1H), 8.15 (dd, J=8.3, 2.3 Hz, 1H), 7.98 (d, J=9.0 Hz, 1H), 7.55 (d, J=8.3 Hz, 1H), 7.45-7.38 (m, 2H), 5.63 (dd, J=8.9, 6.1 Hz, 1H), 5.34 (t, J=6.0 Hz, 1H), 4.62-4.57 (m, 1H), 4.51-4.45 (m, 1H), 4.14-4.04 (m, 2H), 3.97 (t, J=8.9 Hz, 1H), 3.77-3.65 (m, 3H), 2.81 (s, 3H).

MS (EI) n/z: 397 (M⁺).

Example 17

(3R,3aS)-3-(hydroxylmethyl)-7-(6-(3-isopropyl-2-oxazolidin-5-yl)pyridin-3-yl)-3a,4-dihydrobenzo[b]oxazolo[3,4-d][1,4]oxazin-1(3H)-one (15)

Step 1: Preparation of 5-(5-bromopyridin-2-yl)-3-isopropyloxazolidin-2-one (15a)

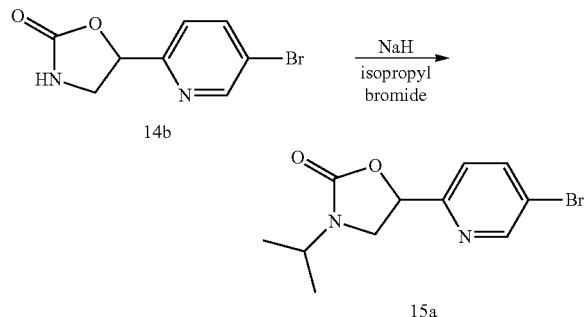

Compound 14b (125 mg, 0.51 mmol), NaH (51 mg, 1.28 mmol) and isopropyl bromide (125 mg, 1.02 mmol) reacted following the synthetic method of compound 14c to afford 67 mg colorless liquid, yield 46%.

$^1$H NMR (300 MHz, CDCl3) δ 8.61 (dd, J$_1$=2.4 Hz, J$_2$=0.7 Hz, 1H), 7.85 (dd, J$_1$=8.4 Hz, J$_2$=2.4 Hz, 1H), 7.41 (dd, J$_1$=8.4 Hz, J$_2$=0.7 Hz, 1H), 5.49 (dd, J$_1$=9.0 Hz, J$_2$=6.1 Hz, 1H), 4.15-4.05 (m, 1H), 391 (t, J=9.01 Hz, 1H), 3.80 (dd, J$_1$=8.8 Hz, J$_2$=6.1 Hz, 1H), 1.21 (d, J=6.8 Hz, 3H), 1.10 (d, J=6.81 Hz, 3H).

MS (EI) m/z: 285 (M$^+$).

Step 2: Preparation of (3R,3aS)-3-(hydroxylmethyl)-7-(6-(3-isopropyl-2-oxazolidin-5-yl)pyridin-3-yl)-3a,4-dihydrobenzo[b]oxazolo[3,4-d][1,4]oxazin-1(3H)-one (15)

Compound I-3 (100 mg, 0.29 mmol), 15a (125 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 afforded 67 mg of white solid (compound 15), yield 54%.

$^1$H NMR (400 MHz, DMSO) δ 8.93 (d, J=1.8 Hz, 1H), 8.15 (dd, J$_1$=8.2 Hz, J$_2$=2.4 Hz, 1H), 8.06-7.92 (m, 1H), 7.53 (d, J=8.1 Hz, 1H), 7.45-7.37 (m, 2H), 5.64 (dd, J=9.0 Hz, J$_2$=6.3 Hz, 1H), 5.34 (t, J=5.7 Hz, 1H), 4.64-4.53 (m, 1H), 4.53-4.41 (m, 1H), 4.17-4.02 (m, 2H), 4.00-3.86 (m, 2H), 3.82-3.61 (m, 3H), 1.16 (d, J=6.7 Hz, 3H), 1.10 (d, J=6.7 Hz, 3H).

MS (EI) m/z: 425 (M$^+$).

Example 18

(3R,3aS)-7-(6-(3-benzyl-2-oxazolidin-5-yl)pyridin-3-yl)-3-(hydroxylmethyl)-3a,4-dihydrobenzo[b]oxazolo[3,4-d][1,4]oxazin-1(3H)-one (16)

Compound I-3 (100 mg, 0.29 mmol), 5-(5-bromopyridin-2-yl)-3-benzyloxazolidin-2-one (146 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 92 mg of white solid (compound 16), yield 67%.

$^1$H NMR (300 MHz, DMSO) δ 8.91 (s, 1H), 8.14 (dd, J$_1$=8.1, J$_2$=2.1 Hz, 1H), 8.03-7.93 (m, 1H), 7.53 (d, J=8.2 Hz, 1H), 7.44-7.25 (m, 7H), 5.72-5.64 (m, 1H), 5.34 (t, J=5.7 Hz, 1H), 4.63-4.52 (m, 1H), 4.51-4.43 (m, 1H), 4.42 (s, 2H), 4.14-4.01 (m, 2H), 3.91-3.82 (m, 1H), 3.82-3.58 (m, 3H).

MS (EI) m/z: 473 (M$^+$).

Example 19

(3R,3aS)-3-(hydroxylmethyl)-7-(6-(2-methyl-2H-tetrazol-5-yl)pyridin-3-yl)-3a,4-dihydrobenzo[b]oxazolo[3,4-d][1,4]oxazin-1(3H)-one (21)

Compound I-3 (100 mg, 0.29 mmol), 5-bromo-2-(2-methyl-2H-tetrazol-S-yl)pyridine (106 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 87 mg of white solid (compound 17), yield 79%.

$^1$H NMR (300 MHz, DMSO) δ 9.14 (d, J=1.8 Hz, 1H), 8.38 (d, J=2.5 Hz, 1H), 8.26 (d, J=2.2 Hz, 1H), 8.02 (d, J=8.8 Hz, 1H), 7.58-7.49 (m, 2H), 4.65-4.57 (m, 1H), 4.52-4.42 (m, 1H), 4.42 (s, 3H), 4.15-4.05 (m, 2H), 3.81-3.65 (m, 2H).

MS (EI) ma/z: 380 (M$^+$).

Example 20

(3R,3aS)-7-(6-((2R)-1,2-dihydroxylpropyl)pyridin-3-yl)-3-(hydroxylmethyl)-3a,4-dihydrobenzo[b]oxazolo[3,4-d][1,4]oxazin-1(3H)-one (18)

Compound 1 (100 mg, 0.27 mmol) was dissolved in dichloromethane and methanol mixed solvent, to which was added NaBH$_4$ (15.3 mg, 0.40 mmol). The resulting mixture was allowed to react overnight at room temperature. TLC (dichloromethane/methanol=20/1) was employed to monitor the reaction. After the reaction completed, the mixture was diluted with water, extracted with dichloromethane. The organic phase was combined, washed with saturated sodium chloride solution, and dried over anhydrous sodium sulfate. Column chromatography (dichloromethane/methanol=40/1) afforded 75 mg of white solid (compound 18), yield 75%.

$^1$H NMR (400 MHz, DMSO) δ 8.78 (d, J=2.3 Hz, 1H), 8.05 (d, J=8.1 Hz, 1H), 7.98-7.94 (m, 1H), 7.52 (d, J=8.3 Hz, 1H), 7.41-7.34 (m, 2H), 5.33 (s, 2H), 4.62-4.55 (m, 1H), 4.51-4.45 (m, 1H), 4.40 (d, J=4.4 Hz, 1H), 4.12-4.06 (m, 2H), 3.91-3.83 (m, 1H), 3.80-3.74 (m, 1H), 3.73-3.66 (m, 1H), 1.02 (d, J=6.4 Hz, 3H).

MS (E) m/z: 372 (M$^+$).

Example 21

(3R,3aS)-3-(hydroxylmethyl)-7-(6-(3-oxomorpholin)pyridin-3-yl)-3a,4-dihydrobenzo[b]oxazolo[3,4-d][1,4]oxazin-1(3H)-one (19)

Step 1: Preparation of 4-(5-bromopyridin-2-yl)morpholin-3-one (19a)

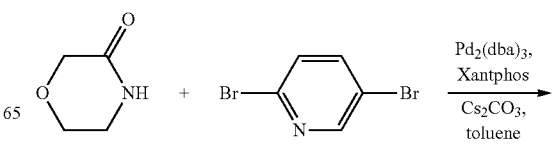

Morpholin-3-one (500 mg, 4.94 mmol) and 2,5-dibromopyridine (1.76 g, 7.42 mmol) were dissolved in toluene, to which was added cesium carbonate (2.42 g, 7.42 mmol). The resulting mixture was flushed with argon for 3 times. Then Pd$_2$(dba)$_3$ (226 mg, 0.247 mmol) and xantphos (171 mg, 0.296 mmol) were added, followed by flushing again with argon. The reaction mixture was heated to 100° C. and allowed to react overnight. After the reaction completed, the mixture was filtered. Column chromatography afforded 815 mg of white solid (compound 19a), yield 64%.

m.p.: 119-120° C.

$^1$H NMR (300 MHz, DMSO) δ 8.65-8.40 (m, 1H), 8.17-7.97 (m, 2H), 4.26 (s, 2H), 4.01-3.95 (m, 2H), 3.95-3.89 (m, 2H).

MS (EI) m/z: 256 (M$^+$).

Step 2: Preparation of (3R,3aS)-3-(hydroxylmethyl)-7-(6-(3-oxomorpholin)pyridin-3-yl)-3a,4-dihydrobenzo[b]oxazolo[3,4-d][1,4]oxazin-1(3H)-one (19)

Compound I-3 (100 mg, 0.29 mmol), 19a (113 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 78 mg of white solid (compound 19), yield 68%.

$^1$H NMR (400 MHz, DMSO) δ 8.78-8.75 (m, 1H), 8.13 (dd, J=8.7, 2.5 Hz, 1H), 8.10-8.05 (m, 1H), 7.99-7.94 (m, 1H), 7.40 (dd, J=6.9, 2.0 Hz, 2H), 5.33 (t, J=5.7 Hz, 1H), 4.63-4.54 (m, 1H), 4.50-4.44 (m, 1H), 4.28 (s, 2H), 4.13-4.03 (m, 2H), 4.00 (s, 4H), 3.82-3.74 (m, 1H), 3.74-3.66 (m, 1H).

MS (ESI) m/z: 398.3 [M+1]$^+$.

Example 22

(3R,3aS)-3-(hydroxylmethyl)-7-(6-(4-methyl-2-oxopiperazin-1-yl)pyridin-3-yl)-3a,4-dihydrobenzo[b]oxazolo[3,4-d][1,4]oxazin-1(3H)-one (20)

Compound I-3 (100 mg, 0.29 mmol), 1-(5-bromopyridin-2-yl)-4-methylpiperidin-2-one (119 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 60 mg of white solid (compound 20), yield 50%.

$^1$H NMR (400 MHz, DMSO) δ 8.75 (d, J=1.9 Hz, 1H), 8.10 (dd, J=8.7, 2.6 Hz, 1H), 7.95 (dd, J=12.0, 8.9 Hz, 2H), 7.39 (dd, J=7.0, 2.0 Hz, 2H), 5.33 (t, J=5.7 Hz, 1H), 4.64-4.53 (m, 1H), 4.50-4.44 (m, 1H), 4.12-4.03 (m, 2H), 3.95-3.88 (m, 2H), 3.81-3.74 (m, 1H), 3.73-3.66 (m, 1H), 3.20 (s, 2H), 2.78-2.72 (m, 2H), 2.29 (s, 3H).

MS (EI) m/z: 410 (M$^+$).

Example 23

5-((3R,3aS)-3-(hydroxylmethyl)-1-oxo-1,3,3a,4-tetrahydrobenzo[b]oxazolo[3,4-d][1,4]oxazin-7-yl)-4-methylpicolinonitrile (21)

Compound I-2 (100 mg, 0.29 mmol), 5-bromo-4-methylpyridine nitrile (87 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 69 mg of white solid (compound 21), yield 71%.

m.p.: 238-240° C.

$^1$H NMR (400 MHz, DMSO) δ 8.55 (s, 1H), 8.04 (s, 1H), 7.98 (d, J=8.3 Hz, 1H), 7.09 (dd, J=12.5, 4.2 Hz, 2H), 5.33 (t, J=5.7 Hz, 1H), 4.62-4.54 (m, 1H), 4.51-4.44 (m, 1H), 4.13-4.05 (m, 2H), 3.82-3.74 (m, 1H), 3.74-3.65 (m, 1H), 2.35 (s, 3H).

MS (EI) m/z: 337 (M$^+$).

Example 24

(3R,3aS)-3-(hydroxylmethyl)-7-(4-methyl-6-(2-oxooxazolidin-3-yl)pyridin-3-yl)-3a,4-dihydrobenzo[b]oxazolo[3,4-d][1,4]oxazin-1(3H)-one (22)

Step 1: Preparation of 3-(5-bromo-4-methylpyridin-2-yl)oxazolidin-2-one (22a)

2-amino-4-methyl-5-bromo-pyridine (3 g, 16 mmol) and K$_2$CO$_3$ (5.5 g, 40 mmol) were added into acetonitrile (35 mL), cooled to 0° C. on ice-salts cooling bath. 2-chloroethyl chloroformate (2.75 g, 19.2 mmol) was added dropwise, and after its completion, the mixture was raised to room temperature, agitated for 1 hr, and refluxed under heat for 3 hrs. TLC (petroleum ether/ethyl acetate=3:1) was employed to monitor the reaction. After the starting materials completely reacted, acetonitrile was removed by evaporation. The resulting mixture was diluted by adding dichloromethane (100 mL), washed sequentially with water and saturated saline solution, and dried over anhydrous sodium sulfate. Column chromatography afforded 2.6 g of white solid, yield 63%.

m.p.: 153-154° C.

$^1$H NMR (300 MHz, CDCl$_3$) δ 8.33 (s, 1H), 8.14 (s, 1H), 4.56-4.43 (m, 2H), 4.29-4.13 (m, 2H), 2.42 (s, 3H).

MS (EI) m/z: 256 (M$^+$).

Step 2: Preparation of (3R,3aS)-3-(hydroxylmethyl)-7-(4-methyl-6-(2-oxooxazolidin-3-yl)pyridin-3-yl)-3a,4-dihydrobenzo[b]oxazolo[3,4-d][1,4]oxazin-1(3H)-one (22)

Compound I-3 (100 mg, 0.29 mmol), 22a (113 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 78 mg of white solid (compound 22), yield 68%.

m.p.: 245-246° C.

$^1$H NMR (400 MHz, DMSO) δ 8.16 (s, 1H), 8.00 (s, 1H), 7.93 (d, J=8.8 Hz, 1H), 7.01 (dd, J=4.4, 2.5 Hz, 2H), 5.33 (t, J=5.7 Hz, 1H), 4.62-4.52 (m, 1H), 4.50-4.43 (m, 4H), 4.22-4.14 (m, 2H), 4.12-4.04 (m, 2H), 3.82-3.74 (m, 1H), 3.73-3.66 (m, 1H), 2.30 (s, 3H).

MS (EI) nm/z: 397 (M$^+$).

Example 25

(3R,3aS)-3-(hydroxylmethyl)-7-(6-((4aS,7aS)-1-methylhexaydro-1H-pyrrolo[3,4-b]pyridin-6(2H)-yl)pyridin-3-yl)-3a,4-dihydrobenzo[b]oxazolo[3,4-d][1,4]oxazin-1(3H)-one (23)

Step 1: Synthesis of (4aS,7aS)-6-(5-bromopyridin-2-yl)octahydro-1H-pyrrolo[3,4-b]pyridine (23a)

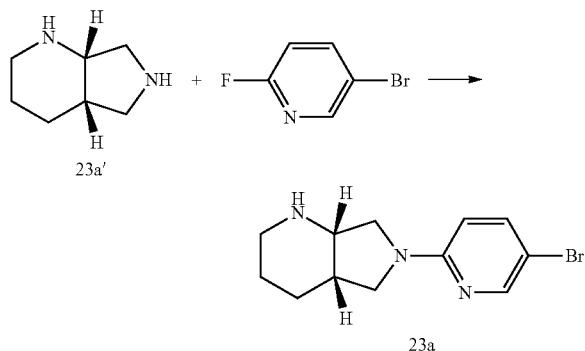

Compound 2-fluoro-5-bromopyridine (1 g, 5.7 mmol) was dissolved in NMP (10 mL), and 23a' (2.15 g, 17.1 mmol) was added. The mixture was heated to 150° C. for reacting overnight. TLC (petroleum ether/ethyl acetate=50/1) was employed to monitor the reaction. After the reaction completed, the mixture was diluted with water, and extracted with ethyl acetate. The organic phase was combined, washed with saturated sodium chloride solution, and dried over anhydrous sodium sulfate. Column chromatography (dichloromethane/methanol=50/1) afforded 1.34 g of white solid (compound 23a), yield 83%.

m.p.: 100-101° C.

$^1$H NMR (400 MHz, CDCl$_3$) δ 8.13 (s, 1H), 7.46 (d, J=9.0 Hz, 1H), 6.23 (d, J=9.0 Hz, 1H), 3.54-3.46 (m, 2H), 3.46-3.41 (m, 2H), 3.41-3.33 (m, 1H), 3.00 (dt, J=11.9, 3.2 Hz, 1H), 2.70-2.62 (m, 1H), 2.42-2.32 (m, 1H), 1.83-1.71 (m, 2H), 1.70-1.57 (m, 1H), 1.54-1.43 (m, 2H).

MS (EI) m/z: 281 (M$^+$).

Step 2: Synthesis of (4aS,7aS)-6-(5-bromopyridin-2-yl)-1-methyloctahydro-1H-pyrrolo[3,4-b]pyridine (23b)

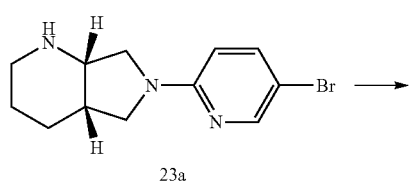

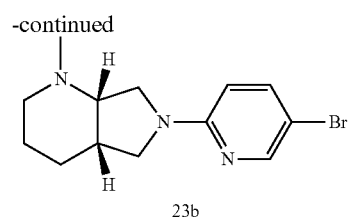

Compound 23a (600 mg, 2.13 mmol) was dissolved in acetonitrile. Potassium carbonate (590 mg, 4.26 mmol) and iodomethane (652 mg, 3.20 mmol) were added. The resulting mixture was allowed to react overnight at 80° C. and monitored by TLC. After the reaction completed, it was cooled to room temperature, diluted with water, and extracted with ethyl acetate. The organic phase was washed with saturated saline solution, and dried over anhydrous sodium sulfate. Column chromatography afforded 405 mg of white solid (compound 23b), yield 64%.

m.p.: 105-107° C.

$^1$H NMR (300 MHz, CDCl$_3$) δ 8.13 (d, J=2.3 Hz, 1H), 7.46 (dd, J=8.9, 2.5 Hz, 1.1), 6.24 (d, J=8.9 Hz, 1H), 3.72 (dd, J=11.0, 2.1 Hz, 1H), 3.50-3.28 (m, 4H), 2.84-2.71 (m, 2H), 2.53-2.42 (m, 1H), 2.31 (s, 3H), 2.25-2.12 (m, 1H), 1.88-1.72 (m, 1H), 1.71-1.51 (m, 2H).

MS (EI) m/z: 295 (M$^+$).

Step 3: Synthesis of (3R,3aS)-3-(hydroxylmethyl)-7-(6-((4aS,7aS)-1-methylhexahydro-1H-pyrrolo[3,4-b]pyridin-6(2H)-yl)pyridin-3-yl)-3a,4-dihydrobenzo[b]oxazolo[3,4-d][1,4]oxazin-1(3H)-one (23)

Compound I-3 (100 mg, 0.29 mmol), 23b (130 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 25 mg of white solid (compound 23), yield 10%.

m.p.: 169-171° C.

$^1$H NMR (400 MHz, DMSO) δ 8.37 (d, J=2.4 Hz, 1H), 7.87 (d, J=8.5 Hz, 1H), 7.77 (dd, J=8.8, 2.5 Hz, 1H), 7.23 (dd, J=8.5, 2.1 Hz, 1H), 7.20 (d, J=2.0 Hz, 1H), 6.47 (d, J=8.8 Hz, 1H), 5.32 (t, J=5.7 Hz, 1H), 4.61-4.51 (m, 1H), 4.45 (dd, J=6.8, 3.3 Hz, 1H), 4.09-3.99 (m, 2H), 3.80-3.73 (m, 2H), 3.72-3.65 (m, 2H), 3.46-3.28 (m, 4H), 2.75-2.61 (m, 2H), 2.42 (s, 1H), 2.19 (s, 3H), 2.06 (t, J=9.4 Hz, 1H), 1.74-1.63 (m, 1H), 1.63-1.57 (m, 2H), 1.51-1.43 (m, 1H).

MS (EI) m/z: 436 (M$^+$).

Example 26

(3R,3aS)-3-(hydroxylmethyl)-7-(6-(5-(hydroxylmethyl)-2-oxooxazolidin-3-yl)pyridin-3-yl)-3a,4-dihydrobenzo[b]oxazolo[3,4-d][1,4]oxazin-1(3H)-one (24)

Step 1: Preparation of 3-(5-bromopyridin-2-yl)-5-(chloromethyl)oxazolidin-2-one

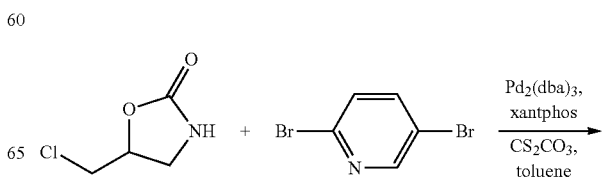

-continued

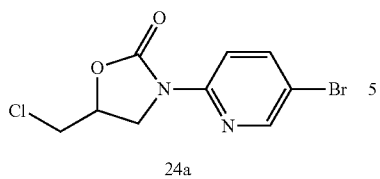

24a 5-(chloromethyl)oxazolidin-2-one (1 g, 7.4 mmol), 2,5-dibromopyridine (2.62 g, 11.1 mmol), cesium carbonate (3.6 g, 11.1 mmol), Pd$_2$(dba)$_3$ (342 mg 0.37 mmol) and xantphos (255 mg, 0.44 mmol) reacted following the synthetic method of compound 19a to afford 1.9 g of pale yellow solid (compound 24a), yield 88%.

$^1$H NMR (300 MHz, CDCl3) δ 8.39 (d, J=2.6 Hz, 1H), 8.15 (dd, J$_1$=8.9 Hz, J$_2$=0.8 Hz, 1H), 7.81 (dd, J$_1$=9.1 Hz, J$_2$=2.4 Hz, 1H), 4.95-4.86 (m, 1H), 4.35 (dd, J=11.1 Hz, J$_2$=8.8 Hz, 1H), 4.15 (dd, J$_1$=11.1 Hz, J$_2$=5.8 Hz, 1H), 3.78 (d, J=5.2 Hz, 2H).

MS (E) m/z: 290 (M$^+$).

Step 2: Preparation of (3-(5-bromopyridin-2-yl)-2-oxooxazolidin-5-yl)methyl acetate (24b)

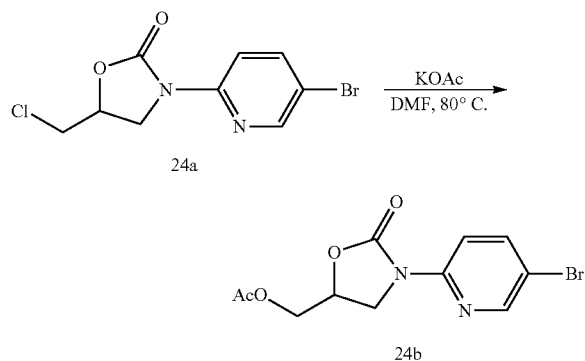

Compound 24a (200 mg, 0.69 mmol) was dissolved in dried N,N-dimethyl formamide (5 mL). Potassium acetate (102 mg, 1.04 mmol) was added. The mixture was heated to 80° C. for reacting overnight. The reaction was monitored by TLC (petroleum ether/ethyl acetate=5/1). After the reaction completed, the mixture was diluted with water, and extracted with ethyl acetate. The organic phase was combined, washed with saturated sodium chloride solution, dried over anhydrous sodium sulfate. Column chromatography (petroleum ether/ethyl acetate=5/1) afforded 200 mg of gel (compound 24b), yield 92%.

$^1$H NMR (300 MHz, CDCl$_3$) δ 8.36 (dd, J$_1$=2.3 Hz, J$_2$=1.7 Hz, 1H), 8.18 (dd, J$_1$=9.0 Hz, J$_2$=1.8 Hz, 1H), 7.80 (dd, J$_1$=9.0 Hz, J$_2$=2.6 Hz, 1H), 4.95-4.85 (m, 1H), 4.40-4.24 (m, 3H), 4.03 (dd, J$_1$=10.8 Hz, J$_2$=6.7 Hz, 1H), 2.08 (s, 3H).

MS (EI) m/z: 314 (M$^+$).

Step 3: Preparation of 3-(5-bromopyridin-2-yl)-5-(hydroxylmethyl)oxazolidin-2-one (24c)

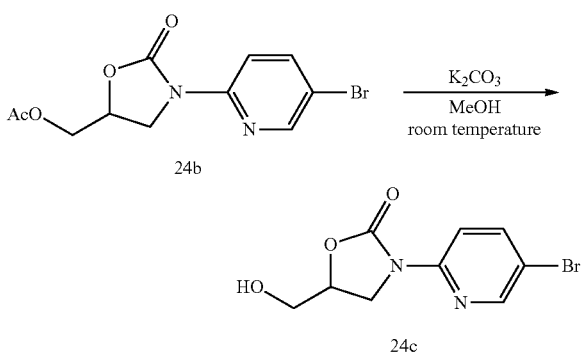

Compound 24b (200 mg, 0.63 mmol) was dissolved in methanol (8 mL). Potassium carbonate (175 mg, 1.27 mmol) was added. Under the protection of argon, the mixture was allowed to react at room temperature for 5 hrs. The reaction was monitored by TLC (petroleum ether/ethyl acetate=5/1). After the reaction completed, the mixture was diluted with water, and extracted with ethyl acetate. The organic phase was combined, washed with saturated sodium chloride solution, dried over anhydrous sodium sulfate. Column chromatography (petroleum ether/ethyl acetate=5/1) afforded 120 mg of white solid (compound 24c), yield 70%.

$^1$H NMR (300 MHz, CDCl3) δ 8.36 (dd, J$_1$=2.6 Hz, J$_2$=0.6 Hz, 1H), 8.15 (dd, J$_1$=9.1 Hz, J$_2$=0.6 Hz, 1H), 7.79 (dd, J$_1$=9.1 Hz, J$_2$=2.6 Hz, 1H), 4.80-4.71 (m, 1H), 4.25 (dd, J$_1$=10.3 Hz, J$_2$=9.1 Hz, 1H), 4.15-4.07 (m, 1H), 4.04-3.95 (m, 1H), 3.81-3.72 (m, 1H).

MS (E) m/z: 272 (M$^+$).

Step 4: Preparation of (3R,3aS)-3-(hydroxylmethyl)-7-(6-(5-(hydroxylmethyl)-2-oxooxazolidin-3-yl)pyridin-3-yl)-3a,4-dihydrobenzo[b]oxazolo[3,4-d][1,4]oxazin-1(3H)-one (24)

Compound I-3 (100 mg, 0.29 mmol), 24c (120 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 96 mg of white solid (compound 34), yield 80%.

$^1$H NMR (300 MHz, DMSO) δ 8.69 (s, 1H), 8.13 (s, 2H), 7.95 (d, J=8.77 Hz, 1H), 7.40-7.32 (m, 2H), 5.34 (t, J=5.6 Hz, 1H), 5.25 (t, J=5.6 Hz, 1H), 4.80-4.70 (m, 1H), 4.63-4.51 (m, 1H), 4.50-4.42 (m, 1H), 4.25-4.17 (m, 1H), 4.15-3.98 (m, 3H), 3.82-3.62 (m, 3H), 3.61-3.52 (m, 1H).

MS (EI) m/z: 413 (M$^+$).

Example 27

(3R,3S)-3-(hydroxylmethyl)-7-(6-((S)-5-(hydroxylmethyl)-2-oxooxazolidin-3-yl)pyridin-3-yl)-3a,4-dihydrobenzo[b]oxazolo[3,4-d][1,4]oxazin-1(3H)-one (25)

Step 1: (S)-5-(((tert-butyldiphenylsilyl)oxy)methyl)oxazolidin-2-one (25a)

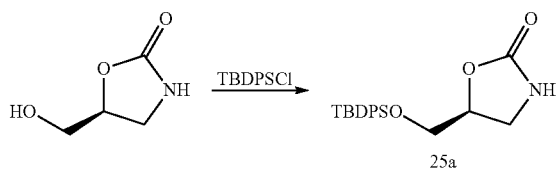

(S)-5-(hydroxylmethyl)oxazolidin-2-one (1.61 g, 13.7 mmol) was dissolved in dried N,N-dimethyl formamide. Imidazole (1.87 g, 27.4 mmol) and DMAP (168 mg, 1.37 mmol) were added. The resulting mixture was cooled to 0° C., and then tert-butyldiphenylchlorosilane (5.66 g, 20.6 mmol) was added. The mixture was raised to room temperature to react for 4 hrs. The reaction was measured by TLC. After the reaction completed, the mixture was diluted with water, and extracted with ethyl acetate. The organic phase was combined, washed sequentially with water and saturated saline solution, dried over anhydrous sodium sulfate, and filtered. Column chromatography afforded 3.85 g of white solid (compound 25a), yield 83%.

m.p.: 85-86° C.

$^1$H NMR (300 MHz, CDCl$_3$) δ 7.71-7.62 (m, 4H), 7.48-7.35 (m, 6H), 6.15 (s, 1H), 4.75-4.60 (m, 1H), 3.86 (dd, J=11.2, 4.5 Hz, 1H), 3.75 (dd, J=11.2, 4.0 Hz, 1H), 3.68-3.52 (m, 2H), 1.06 (s, 9H).

MS (ESI) m/z: 362.4 [M+Na]$^+$.

Step 2: Preparation of (S)-3-(5-bromopyridin-2-yl)-5-(((tert-butyldiphenylsilyl)oxy)methyl)oxazolidin-2-one (25b)

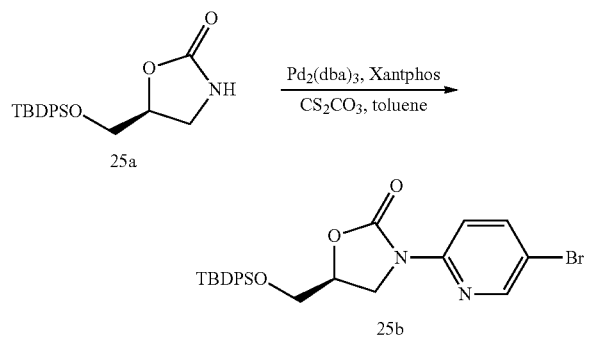

Compound 25a (927 mg, 2.73 mmol), 2,5-dibromopyridine (500 mg, 2.1 mmol, cesium carbonate (1.03 g, 3.15 mmol), Pd$_2$(dba)$_3$ (100 mg, 0.1 mmol) and xantphos (73 mg, 0.13 mmol), reacted following the synthetic method of compound 19a to afford 750 mg of viscous liquid, yield 70%.

$^1$H NMR (300 MHz, CDCl$_3$) δ 8.38 (dd, J=2.4, 0.6 Hz, 1H), 8.20 (dd, J=9.0, 0.6 Hz, 1H), 7.79 (dd, J=0.0, 2.5 Hz, 1H), 7.70-7.59 (m, 4H), 7.50-7.31 (m, 6H), 4.81-4.59 (m, 1H), 4.30-4.16 (m, 2H), 3.96 (dd, J=11.4, 3.4 Hz, 1H), 3.77 (dd, J=11.5, 3.2 Hz, 1H), 0.98 (s, 9H).

MS (EI) m/z: 511 (M$^+$).

Step 3: Preparation of (S)-3-(5-bromopyridin-2-yl)-5-(hydroxylmethyl)oxazolidin-2-one (25c)

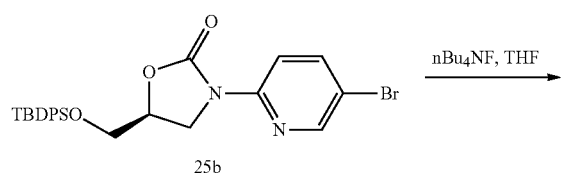

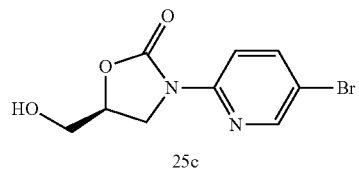

Compound 25b (1.4 g, 2.83 mmol) was dissolved in tetrahydrofuran, cooled to 0° C., and $^n$Bu$_4$NF (4.2 mL, 4.2 mmol, 4.2 M solution in tetrahydrofuran) was added. The mixture was allowed to react for 5 hrs and monitored by TLC. After the reaction completed, the mixture was diluted with water, and extracted with ethyl acetate. The organic phase was wash with saturated saline solution, dried over anhydrous sodium sulfate. Column chromatography afforded 645 mg of white solid, yield 83%.

m.p.: 128-130° C.

$^1$H NMR (400 MHz, CDCl$_3$) δ 8.36 (d, J=2.0 Hz, 1H), 8.14 (d, J=9.0 Hz, 1H), 7.78 (dd, J=9.0, 2.4 Hz, 1H), 4.82-4.69 (m, 1H), 4.26 (dd, J=10.4, 9.2 Hz, 1H), 4.11 (dd, J=10.5, 6.8 Hz, 1H), 4.05-3.95 (m, 1H), 3.83-3.74 (m, 1H), 2.28 (t, J=6.5 Hz, 1H).

MS (EI) m/z: 272 (M$^+$).

Step 4: Preparation of (3R,3aS)-3-(hydroxylmethyl)-7-(6-((S)-5-(hydroxylmethyl)-2-oxooxazolidin-3-yl)pyridin-3-yl)-3a,4-dihydrobenzo[b]oxazolo[3,4-d][1,4]oxazin-1(3H)-one (25)

Compound I-3 (100 mg, 0.29 mmol), 25c (120 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 91 mg of white solid (compound 25), yield 76%.

$^1$H NMR (300 MHz, DMSO) δ 8.69 (s, 1H), 8.13 (s, 2H), 7.95 (d, J=8.77 Hz, 1H), 7.40-7.32 (m, 2H), 5.34 (t, J=5.6 Hz, 1H), 5.25 (t, J=5.6 Hz, 1H), 4.80-4.70 (m, 1H), 4.63-4.51 (m, 1H), 4.50-4.42 (m, 1H), 4.25-4.17 (m, 1H), 4.15-3.98 (m, 3H), 3.82-3.62 (m, 3H), 3.61-3.52 (m, 1H).

MS (EI) m/z: 413 (M$^+$).

Example 28

(3R,3aS)-3-(hydroxylmethyl)-7-(6-((R)-5-(hydroxylmethyl)-2-oxo-oxazolidin-3-yl)pyridin-3-yl)-3a,4-dihydrobenzo[b]oxazolo[3,4-d][1,4]oxazin-1(3H)-one (26)

Compound 26 can be successfully prepared by following the synthetic method of compound 25 described above.

$^1$H NMR (300 MHz, DMSO) δ 8.69 (s, 1H), 8.13 (s, 2H), 7.95 (d, J=8.77 Hz, 1H), 7.40-7.32 (m, 2H), 5.34 (t, J=5.6 Hz, 1H), 5.25 (t, J=5.6 Hz, 1H), 4.80-4.70 (m, 1H), 4.63-4.51 (m H), 4.50-4.42 (m, 1H), 4.25-4.17 (m, 1H), 4.14-3.97 (m, 3H), 3.81-3.62 (m, 3H), 3.61-3.52 (m, 1H).

MS (EI) m/z: 413 (M$^+$).

Example 29

(3R,3aS)-3-(hydroxylmethyl)-7-(6-((R)-3-methyl-2-oxazolidin-5-yl)pyridin-3-yl)-3a,4-dihydrobenzo[b]oxazolo[3,4-d][1,4]oxazin-1(3H)-one (27)

Step 1: Preparation of 1-(5-bromopyridin-2-yl-2-chloroethanone (27a)

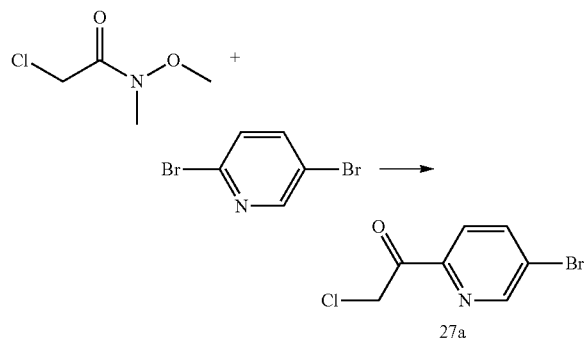

2,5-dibromopyridine (30 g, 0.126 mol), 2-chloro-N-methoxyl-N-methylacetylamine (22.5 g, 0.164 mol) and ⁿBuLi (60.4 mL, 0.15 mol, 2.5 M in toluene) reacted at −78° C. following the synthetic method of compound 1a to afford 21 g of white solid (compound 27a), yield 71%.

¹H NMR (400 MHz, CDCl₃) δ 8.72 (dd, J=2.2, 0.8 Hz, 1H), 8.02 (dd, J=8.4, 2.2 Hz, 1H), 7.98 (dd, J=8.4, 0.8 Hz, 1H), 5.05 (s, 2H).

Step 2: Preparation of (R)-1-(5-bromopyridin-2-yl)-2-chloromethanol (27b)

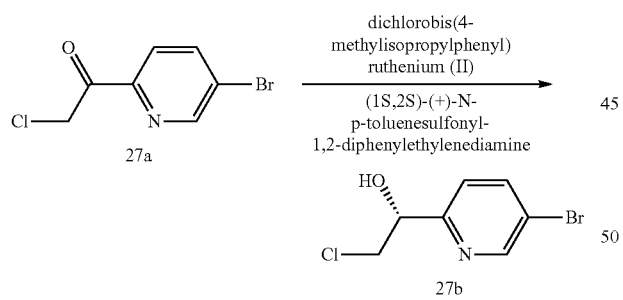

Under the protection of argon, dichloro bis(4-methylisopropylphenyl)ruthenium (II) (200 mg, 0.32 mmol) and (1S,2S)-(+)-N-(4-toluenesulfonyl)-1,2-diphenylethylenediamine (234 mg, 0.64 mmol) was dissolved in dried N,N-dimethyl formamide. Triethylamine (67 mg, 0.66 mmol) was added and the mixture was agitated at room temperature for 1 hr.

Formic acid (4.0 Ml, 106.5 mmol) and triethylamine (6 Ml, 42.6 mmol) were mixed evenly, to which was added the solution of compound 27a (5 g, 21.3 mmol) in methyl tert-butyl ether, and then was added the catalyst and ligand solution described above. The resulting mixture was allowed to react overnight at room temperature. TLC (petroleum ether/ethyl acetate=3/1) was employed to monitor the reaction. After compound 27a reacted completely, water (40 ml) was added to the reaction mixture, and the mixture was agitated for 30 mins, and extracted with ethyl acetate. The organic phase was combined, washed sequentially with water and saturated saline solution, and dried over anhydrous sodium sulfate. Column chromatography afforded 4.5 g of white powder (compound 27b), yield 89%.

¹H NMR (400 MHz, DMSO) δ 8.66 (d, J=1.9 Hz, 1H), 8.08 (dd, J=8.4, 2.4 Hz, 1H), 7.51 (d, J=8.4 Hz, 1H), 6.08 (d, J=5.2 Hz, 1H), 4.85 (dd, J=9.6, 5.3 Hz, 1H), 3.94 (dd, J=11.0, 4.0 Hz, 1H), 3.83 (dd, J=11.1, 5.7 Hz, 1H).

MS (EI) m/z: 236 (M⁺).

Step 3: Preparation of (S)-2-azido-1-(5-bromopyridin-2-yl) ethanol (27c)

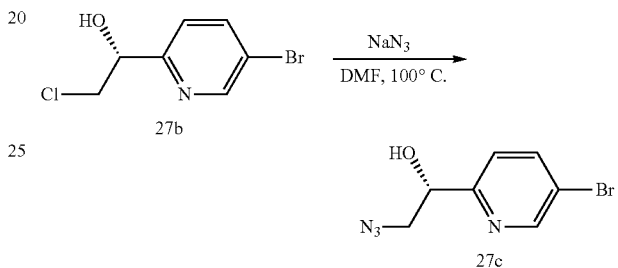

Compound 27b (4 g, 16.9 mmol) was dissolved in dried N,N-dimethyl formamide. NaN₃ (4.39 g, 67.6 mmol) was added and the mixture was heated to 100° C. and allowed to react for 6 hrs. TLC (petroleum ether/ethyl acetate=5/1) was employed to monitor the reaction. After compound 27b reacted completely, the reaction mixture was cooled to room temperature, diluted with water, and extracted with ethyl acetate. The organic phase was combined, washed sequentially with water and saturated saline solution, and dried over anhydrous sodium sulfate. Column chromatography afforded 3.42 g of white powder (compound 27c), yield 83.2%.

¹H NMR (300 MHz, DMSO) δ 8.64 (d, J=2.4 Hz, 1H), 8.08 (dd, J=8.4, 2.4 Hz, 1H), 7.54 (d, J=8.4 Hz, 1H), 6.13 (d, J=5.1 Hz, 1H), 4.80 (dd, J=9.5, 5.9 Hz, 1H), 3.56 (dd, J=12.7, 3.7 Hz, 1H), 3.47 (dd, J=12.6, 6.5 Hz, 1H).

MS (ESI) m/z: 243.3[M+H]⁺.

Step 4: Preparation of (S)-2-amino-1-(5-bromopyridin-2-yl)ethanol (27d)

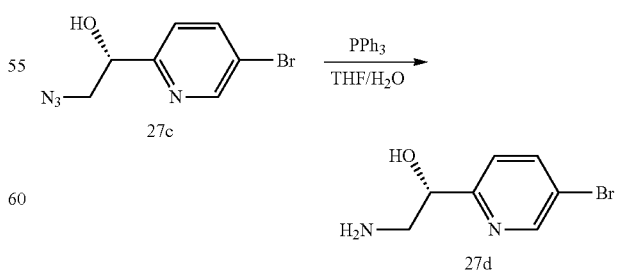

Compound 27c (4.8 g, 20 mmol) was dissolved in tetrahydrofuran (10 mL). Under the protection of argon, PPh₃ (5.8 g, 22 mmol) was added, and the reaction mixture was heated to 45° C. to react for 2 hrs. Then water (7.86 mL) was added and the mixture was cooled to room temperature to react for 13 hrs. TLC (dichloromethane/methanol=20/1) was employed to monitor the reaction. After the reaction completed, the mixture was diluted with water, and extracted with ethyl acetate. The organic phase was combined, washed with saturated sodium chloride solution, dried over anhydrous sodium sulfate, and then dried by rotary evaporation. Column chromatography afforded 4.0 g of white solid (compound 27d), yield 93.2%.

$^1$H NMR (400 MHz, DMSO) δ 8.60 (d, J=2.3 Hz, 1H), 8.01 (dd, J=8.4, 2.4 Hz, 1H), 7.45 (d, J=8.4 Hz, 1H), 5.53 (s, 1H), 4.47 (dd, J=7.0, 3.9 Hz, 1H), 2.85 (dd, J=12.9, 4.0 Hz, 1H), 2.62 (dd, J=12.9, 7.2 Hz, 1H), 1.52 (s, 2H).

MS (EI) m/z: 217 (M$^+$).

Step 5: Preparation of (S)-5-(5-bromopyridin-2-yl)oxazolidin-2-one (27e)

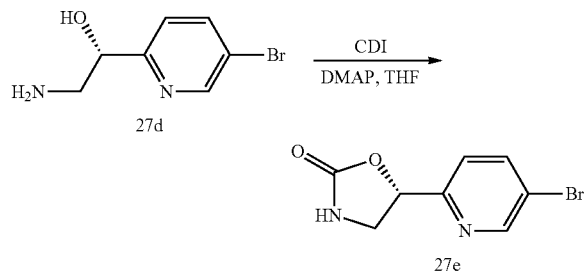

Compound 27d (4.0 g, 18.4 mmol) was dissolved in dried tetrahydrofuran. Carbonyldiimidazole (4.48 g, 27.6 mmol) and DMAP (450 mg, 3.68 mmol) were added and the resulting mixture was allowed to react overnight at room temperature. TLC was employed to monitor the reaction. After compound 27d reacted completely, silica gel was added to the reaction mixture. Column chromatography afforded 3.9 g of white powder (compound 27e), yield 87.2%.

$^1$H NMR (400 MHz, DMSO) δ 8.75 (dd, J=2.3, 0.5 Hz, 1H), 8.14 (dd, J=8.4, 2.4 Hz, 1H), 7.75 (s, 1H), 7.46 (d, J=8.3 Hz, 1H), 5.63 (dd, J=9.0, 6.1 Hz, 1H), 3.92-3.85 (m, 1H), 3.56-3.50 (m, 1H).

Step 6: Preparation of (S)-5-(5-bromopyridin-2-yl)-3-methyloxazolidin-2-one (27f)

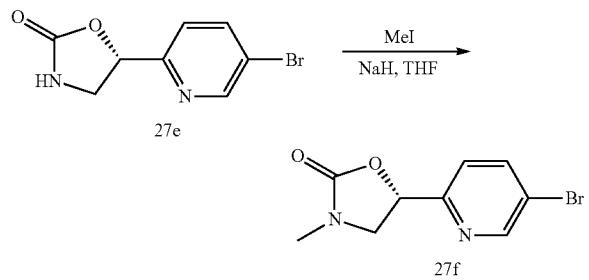

Compound 27e (931 mg, 3.83 mmol), 60% NaH (184 mg, 4.60 mmol) and MeI (0.477 Ml, 7.66 mmol) reacted following the synthetic method of compound 14c to afford 897 mg of colorless transparent liquid (compound 27f), yield 91%.

$^1$H NMR (400 MHz, DMSO) δ 8.75 (dd, J=2.4, 0.6 Hz, 1H), 8.13 (dd, J=8.4, 2.4 Hz, 1H), 7.47 (dd, J=4.7, 4.2 Hz, 1H), 5.58 (dd, J=9.1, 6.2 Hz, 1H), 3.95 (dd, J=11.3, 6.6 Hz, 1H), 3.62 (dd, J=8.8, 6.2 Hz, 1H), 2.78 (s, 3H).

Step 7: Preparation of (3R,3aS)-3-(hydroxylmethyl)-7-(6-((R)-3-methyl-2-oxazolidin-5-yl)pyridin-3-yl)-3a,4-dihydrobenzo[b]oxazolo[3,4-d][1,4]oxazin-1(3H)-one (27)

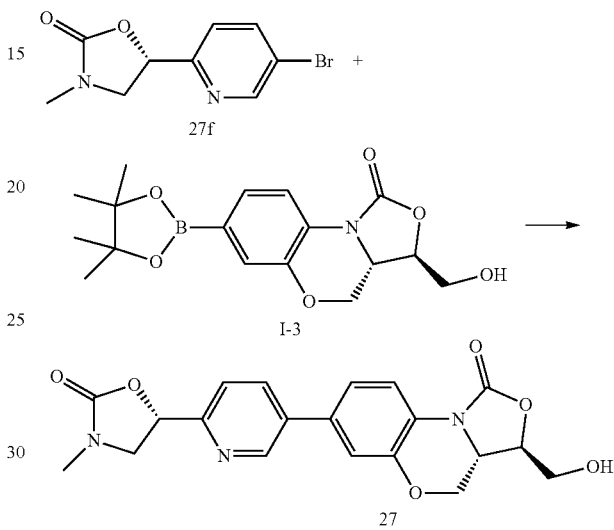

Compound 27f (308 mg, 1.20 mmol), I-3 (347 mg, 1.00 mmol), cesium carbonate (814 mg, 2.50 mmol) and Pd(PPh$_3$)$_4$ (116 mg, 0.10 mmol) reacted following the synthetic method of compound 1 to afford 294 mg of white solid (compound 27), yield 74%.

$^1$H NMR (400 MHz, DMSO) δ 8.93 (d, J=1.9 Hz, 1H), 8.15 (dd, J=8.1, 2.3 Hz, 1H), 8.00-7.96 (m, 1H), 7.55 (d, J=8.1 Hz, 1H), 7.43-7.38 (m, 2H), 5.63 (dd, J=9.0, 6.2 Hz, 1H), 5.33 (t, J=5.7 Hz, 1H), 4.63-4.55 (m, 1H), 4.51-4.45 (m, 1H), 4.13-4.04 (m, 2H), 3.97 (t, J=8.9 Hz, 1H), 3.81-3.74 (m, 1H), 3.74-3.66 (m, 2H), 2.81 (s, 3H).

MS (ESI) m/z: 398.2 [M+1]$^+$.

Example 30

Preparation of (3R,3aS)-3-(hydroxylmethyl)-7-(6-((S)-3-methyl-2-oxazolidin-5-yl)pyridin-3-yl)-3a,4-dihydrobenzo[b]oxazolo[3,4-d][1,4]oxazin-1(3H)-one (28)

Compound 28 was successfully prepared by following the synthetic route of compound 27.

$^1$H NMR (400 MHz, DMSO) δ 8.92 (dd, J=2.3, 0.6 Hz, 1H), 8.15 (dd, J=8.2, 2.4 Hz, 1H), 8.01-7.96 (m, 1H), 7.55 (d, J=8.1 Hz, 1H), 7.43-7.38 (m, 2H), 5.63 (dd, J=9.0, 6.2 Hz, 1H), 5.33 (t, J=5.7 Hz, 1H), 4.63-4.55 (m, 1H), 4.48 (dt, J=7.6, 3.9 Hz, 1H), 4.13-4.03 (m, 2H), 3.96 (dd, J=15.7, 6.8 Hz, 1H), 3.81-3.74 (m, 1H), 3.73-3.66 (m, 2H), 2.81 (s, 3H).

MS (ESI) m/z: 398.2 [M+1]$^+$.

Example 31

(3R,3aS)-7-(6-(1-aminocyclopropyl)pyridin-3-yl)-3-(hydroxylmethyl)-3a,4-dihydrobenzo[b]oxazolo[3,4-d][1,4]oxazin-1(3H)-one (29)

Step 1: Preparation of tert-butyl(1-(5-((3R,3aS)-3-(hydroxylmethyl)-1-oxo-1,3,3a,4-tetrahydrobenzo[b]oxazolo[3,4-d][1,4]oxazin-7-yl)pyridin-2-yl)cyclopropyl)amide (29a)

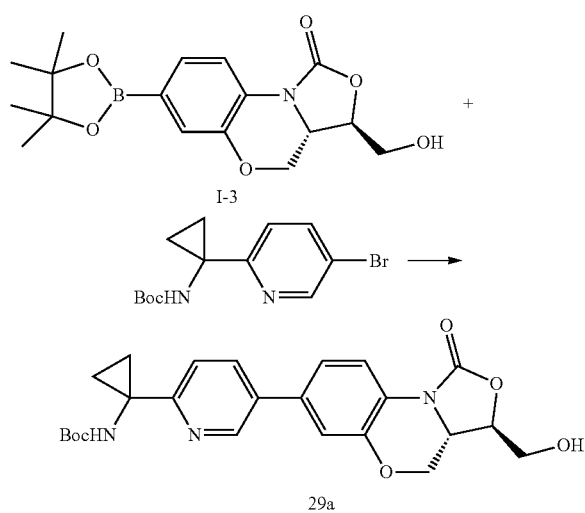

Compound I-3 (100 mg, 0.29 mmol), 2-(1-(Boc-amino)cyclopropan-1-yl)-5-bromopyridine (137 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 88 mg of white solid (compound 29a), yield 67%.

$^1$H NMR (300 MHz, DMSO) δ 8.71 (d, J=1.9 Hz, 1H), 8.01 (d, J=8.2 Hz, 1H), 7.94 (d, J=8.2 Hz, 1H), 7.81 (s, 1H), 7.39-7.31 (m, 3H), 5.31 (t, J=5.6 Hz, 1H), 4.61-4.55 (m, 1H), 4.50-4.41 (m, 1H), 4.12-4.02 (m, 2H), 3.81-3.65 (m, 1H), 1.42 (s, 9H), 1.27 (dd, J$_1$=7.0, J$_2$=3.1, 2H), 1.14 (dd, J$_1$ 7.0 Hz, J$_2$=3.1 Hz, 2H).

MS (EI) m/z: 453 (M$^+$).

Step 2: Preparation of (3R,3aS)-7-(6-(1-aminocyclopropyl)pyridin-3-yl)-3-(hydroxylmethyl)-3a,4-dihydrobenzo[b]oxazolo[3,4-d][1,4]oxazin-1(3H)-one (29)

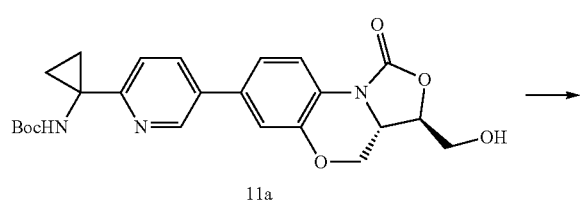

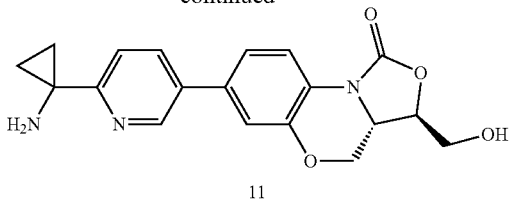

Compound 11a (100 mg, 0.22 mmol) was dissolved in dichloromethane and methanol mixed solvent, to which was added trifluoroacetic acid (2.5 mL), and the mixture was allowed to react at room temperature. After the reaction completed, excess trifluoroacetic acid was removed by evaporation. Then ethyl acetate was added, pH value was adjusted with sodium bicarbonate solution to 8, and the mixture was extracted with ethyl acetate. Column chromatography afforded 57 mg of white solid (compound 29), yield 73%.

$^1$H NMR (400 MHz, DMSO) δ 8.70 (d, J=1.8 Hz, 1H), 7.99 (dd, J=8.4, 2.4 Hz, 1H), 7.94 (d, J=8.2 Hz, 1H), 7.79 (d, J=8.3 Hz, 1H), 7.38-7.31 (m, 2H), 5.33 (t, J=5.6 Hz, 1H), 4.63-4.53 (m, 1H), 4.51-4.43 (m, 1H), 4.13-4.00 (m, 2H), 3.81-3.75 (m, 1H), 3.74-3.66 (m, 1H), 1.28-1.19 (m, 2H), 1.01-0.96 (m, 2H).

MS (ET) m/z: 353 (M$^+$).

Example 32

(3R,3aS)-7-(6-(aminomethyl)pyridin-3-yl)-3-(hydroxylmethyl)-3a,4-dihydrobenzo[b]oxazolo[3,4-d][1,4]oxazin-1(3H)-one (30)

Step 1: Preparation of (3R,3aS)-7-(6-(azidomethyl)pyridin-3-yl)-3-(hydroxylmethyl)-3a,4-dihydrobenzo[b]oxazolo[3,4-d][1,4]oxazin-1(3H)one (30a)

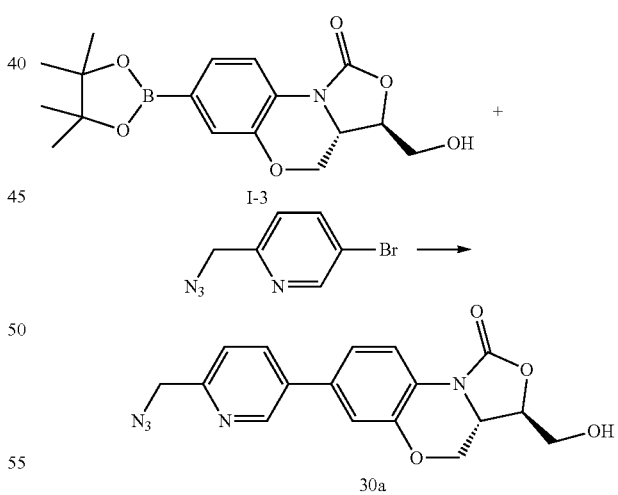

Compound I-3 (200 mg, 0.58 mmol), 2-(azidomethyl)-5-bromopyridine (184 mg, 0.86 mmol), cesium carbonate (286 mg, 1.16 mmol) and Pd(PPh$_3$)$_4$ (55 mg, 0.058 mmol), under the protection of argon, reacted following the synthetic method of compound 1 to afford 130 mg of white solid (compound 30a), yield 64%.

$^1$H NMR (300 MHz, DMSO) δ 8.89 (d, J=2.1 Hz, 1H), 8.10 (dd, J$_1$=8.0 Hz, J$_2$=2.1 Hz, 1H), 4.51 (s, 2H), 4.50-4.42 (m, 1H), 4.11-4.01 (m, 2H), 3.80-3.65 (m, 2H).

MS (EI) m/z: 353 (M$^+$).

Step 2: Preparation of (3R,3aS)-7-(6-(aminomethyl)pyridin-3-yl)-3-(hydroxylmethyl)-3a,4-dihydrobenzo[b]oxazolo[3,4-d][1,4]oxazin-1(3H)-one (30)

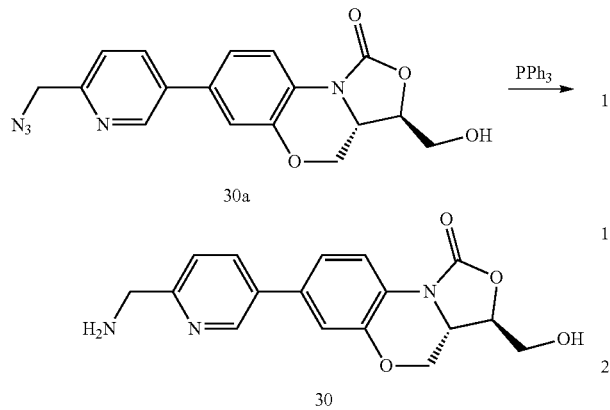

Compound 30a (100 mg, 0.28 mmol) and PPh₃ (80 mg, 0.31 mmol) reacted following the synthetic method of 27d to afford 57 mg of white solid (compound 30), yield 62%.

¹H NMR (300 MHz, DMSO) δ 8.77 (s, 1H), 8.02 (dd, J₁=8.2 Hz, J₂=2.3 Hz, 1H), 7.95 (d, 4.50-4.42 (m, 1H), 4.10-4.05 (m, 2H), 3.85 (s, 2H), 3.80-3.65 (m, 2H).

MS (EI) m/z: 327 (M⁺).

Example 33

(3R,3aS)-3-(hydroxylmethyl)-7-(6-(2-oxopiperazin-1-yl)pyridin-3-yl)-3a,4-dihydrobenzo[b]oxazolo[3,4-d][1,4]oxazin-1(3H)-one (31)

Step 1: Preparation of benzyl 4-(5-bromopyridin-2-yl)-3-oxopiperidin-1-carboxylate (31a)

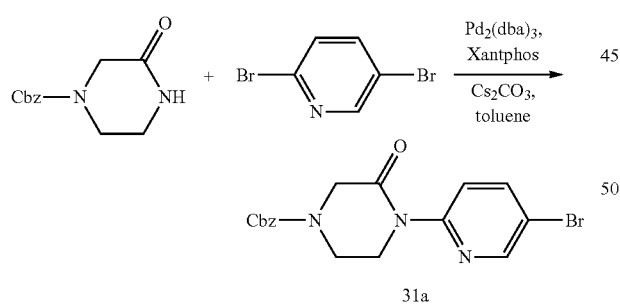

3-oxopiperidin-1-benzyl formate (860 mg, 2.67 mmol), 2,5-dibromopyridine (949 mg, 4.01 mmol), cesium carbonate (1.74 g, 5.34 mmol), Pd₂(dba)₃ (127 mg, 0.13 mmol) and xantphos (92.3 mg, 0.16 mmol) reacted following the synthetic method of compound 19a to afford 1 g of white solid, yield 97%.

¹H NMR (400 MHz, DMSO) δ 8.58 (d, J=2.4 Hz, 1H), 8.07 (dd, J=8.9, 2.6 Hz, 1H), 7.90 (dd, J=8.9, 0.7 Hz, 1H), 7.42-7.30 (m, 5H), 5.13 (s, 2H), 4.23 (d, J=16.3 Hz, 2H), 4.04 (s, 2H), 3.72 (s, 2H).

MS (EI) m/z: 388 (M⁺).

Step 2: 4-(5-((3R,3aS)-3-(hydroxylmethyl)-1-oxo-1,3,3a,4-tetrahydrobenzo[b]oxazolo[3,4-d][1,4]oxazin-7-yl)pyridin-2-yl)-3-oxopiperidin-1-benzyl formate (31b)

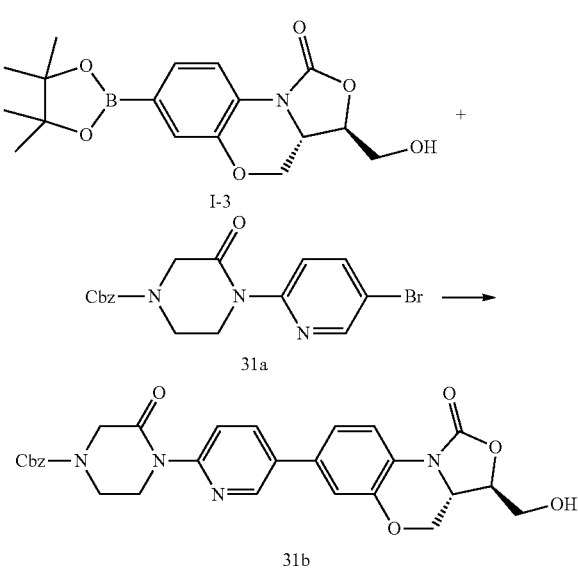

Compound I-3 (100 mg, 0.29 mmol), 31a (171 mg, 0.44 mmol), cesium carbonate (234 mg, 0.72 mmol) and Pd(PPh₃)₄ (34 mg, 0.029 mmol), under the protection of argon, reacted following the synthetic method of compound 1 to afford 102 mg of white solid (compound 31b), yield 66%.

¹H NMR (300 MHz, DMSO) δ 8.76 (d, J=1.7 Hz, 1H), 8.13 (dd, J=8.7, 2.4 Hz, 1H), 7.99-7.92 (m, 2H), 7.48-7.26 (m, 7H), 5.33 (t, J=5.1 Hz, 1H), 5.14 (s, 2H), 4.63-4.54 (m, 1H), 4.50-4.43 (m, 1H), 4.24 (s, 2H), 4.15-4.02 (m, 4H), 3.82-3.65 (m, 4H).

MS (ESI) m/z: 553.2 [M+Na]⁺.

Step 3: Preparation of (3R,3aS)-3-(hydroxylmethyl)-7-(6-(2-oxopiperazin-1-yl)pyridin-3-yl)-3a,4-dihydrobenzo[b]oxazolo[3,4-d][1,4]oxazin-1(3H)-one (31)

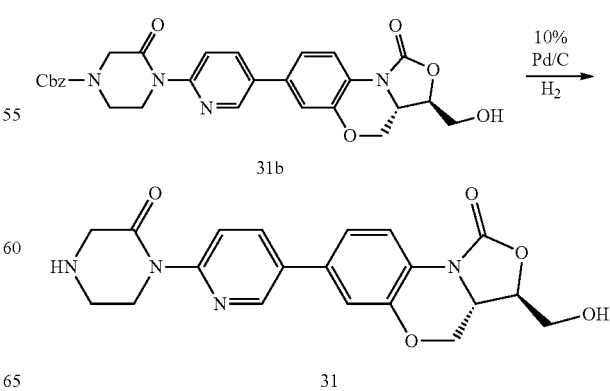

Compound 31b (100 mg, 0.19 mmol) was dissolved in methanol and tetrahydrofuran mixed solvent, and subjected to hydrogenation at normal pressure and temperature with the catalysation by 10% Pd/C (20 mg), which afforded 54 mg of white solid (compound 31), yield 72%.

$^1$H NMR (400 MHz, DMSO) δ 8.75 (d, J=2.6 Hz, 1H), 8.10 (dd, J=8.7, 2.6 Hz, 1H), 7.95 (dd, J=8.7, 6.5 Hz, 2H), 7.39 (dd, J=7.1, 2.0 Hz, 2H), 5.33 (t, J=5.7 Hz, 1H), 4.63-4.53 (m, 1H), 4.50-4.45 (m, 1H), 4.42 (t, J=5.2 Hz, 1H), 4.13-4.03 (m, 2H), 3.93-3.87 (m, 2H), 3.81-3.74 (m, 1H), 3.74-3.66 (m, 1H), 3.45-3.39 (m, 2H), 3.24 (s, 2H), 2.82-2.75 (m, 2H), 2.44-2.37 (m, 2H).

MS (E) m/z: 396 (M$^+$).

Example 34

(3R,3aS)-7-(6-((4aS,7aS)-hexahydro-1H-pyrrolo[3,4-b]pyridin-6(2H)-yl)pyridin-3-yl)-3-(hydroxylmethyl)-3a,4-dihydrobenzo[b]oxazolo[3,4-d][1,4]oxazin-1(3H)-one (32)

Step 1: Synthesis of (4aS,7aS)-tert-butyl-6-(5-bromopyridin-2-yl)octahydro-1H-pyrrolo[3,4-b]pyridin-1-carboxylate (32a)

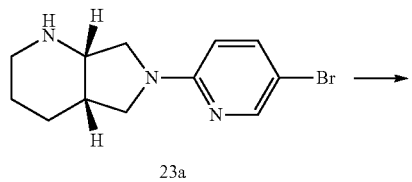

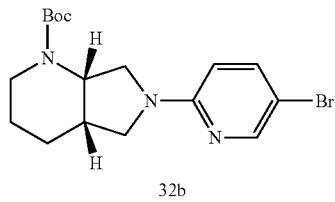

Compound 23a (1.25 g, 4.4 mmol) was dissolved in tetrahydrofuran (10 mL) and water (5 mL) mixed solvent, to which were added sodium bicarbonate (0.74 g, 8.8 mmol) and Di-tert-butyl dicarbonate (1.15 g, 6.6 mmol). The resulting mixture was allowed to react at room temperature for 6 hrs. TLC (petroleum ether, ethyl acetate=1/1) was employed to monitor the reaction. After the reaction completed, the mixture was diluted with water, and extracted with ethyl acetate. The organic phase was combined, washed with saturated saline solution, and dried over anhydrous sodium sulfate. Column chromatography (petroleum ether/ethyl acetate=10/1) afforded 1.46 g of white solid (compound 32b), yield 87%.

$^1$H NMR (300 MHz, CDCl$_3$) δ 8.15 (d, J=2.2 Hz, 1H), 7.48 (dd, J=8.9, 2.5 Hz, 1H), 6.23 (d, J=9.0 Hz, 1H), 4.79 (s, 1H), 4.01 (s, 1H), 3.62-3.44 (m, 2H), 3.40-3.22 (m, 2H), 2.84-2.70 (m, 1H), 2.31-2.20 (m, 1H), 1.89-1.61 (m, 2H), 1.47 (s, 9H), 1.43-1.24 (m, 2H).

MS (ESI) m/z: 382.3 [M+Na]$^+$.

Step 2: Synthesis of (4aS,7aS)-tert-butyl-6-(5-((3R,3aS)-3-(hydroxylmethyl)-1-oxo-1,3,3a,4-tetrahydrobenzo[b]oxazolo[3,4-d][1,4]oxazin-7-yl)pyridin-2-yl)octahydro-1H-pyrrolo[3,4-b]pyridin-1-carboxylate (32b)

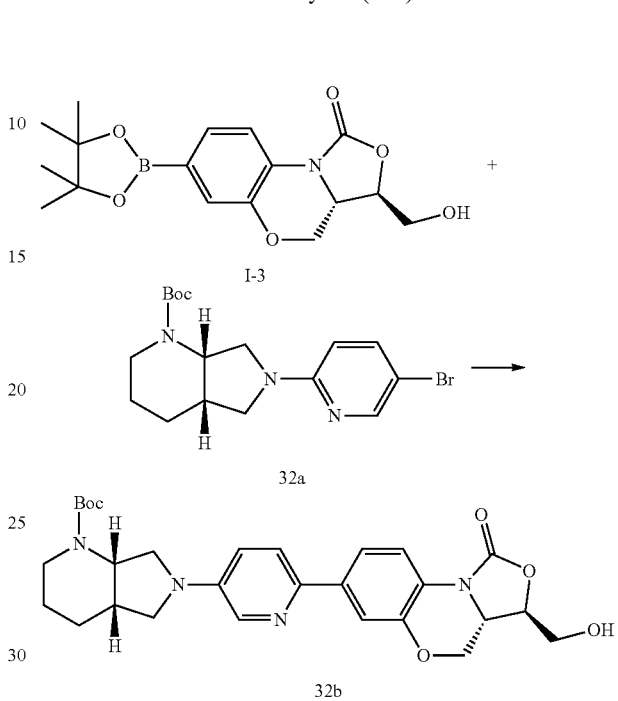

Compound I-3 (100 mg, 0.29 mmol), 32a (168 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 80 mg of white solid (compound 32b), yield 53%.

m.p.: 257-259° C.

$^1$H NMR (400 MHz, DMSO) δ 8.37 (d, J=2.5 Hz, 1H), 7.86 (d, J=8.4 Hz, 1H), 7.78 (dd, J=8.8, 2.5 Hz, 1H), 7.22 (dd, J=8.5, 2.1 Hz, 1H), 7.19 (d, J=2.0 Hz, 1H), 6.50 (d, J=8.8 Hz, 1H), 5.30 (t, J=5.7 Hz, 1H), 4.66 (s, 1H), 4.57-4.49 (m, 1H), 4.48-4.40 (m, 1H), 4.07-3.97 (m, 2H), 3.86 (d, J=13.1 Hz, 1H), 3.79-3.71 (m, 1H), 3.71-3.63 (m, 1H), 3.52 (t, J=9.3 Hz, 1H), 3.49-3.42 (m, 1H), 3.38-3.32 (m, 2H), 2.85-2.71 (m, 1H), 2.28-2.14 (m, 1H), 1.77-1.68 (m, 1H), 1.67-1.59 (m, 1H), 1.30-1.19 (m, 2H).

MS (EI) m/z: 522 (M$^+$).

Step 3: (3R,3aS)-7-(6-((4aS,7aS)-hexahydro-1H-pyrrolo[3,4-b]pyridin-6(2H)-yl)pyridin-3-yl)-3-(hydroxylmethyl)-3a,4-dihydrobenzo[b]oxazolo[3,4-d][1,4]oxazin-1(3H)-one (32)

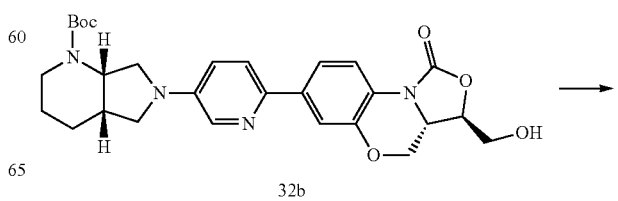

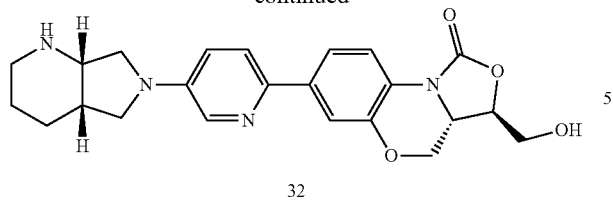

Compound 32b (100 mg, 0.19 mmol) reacted following the synthetic method of compound 29 to afford 54 mg of white solid (compound 32), yield 67%.

m.p.: 210-212.

$^1$H NMR (400 MHz, DMSO) δ 8.37 (d, J=2.3 Hz, 1H), 7.87 (d, J=8.4 Hz, 1H), 7.77 (dd, J=8.8, 2.5 Hz, 1H), 7.23 (dd, J=8.5, 2.0 Hz, 1H), 7.19 (d, J=2.0 Hz, 1H), 6.45 (d, J=8.8 Hz, 1H), 5.33 (s, 1H), 4.60-4.50 (m, 1H), 4.50-4.40 (m, 1H), 4.11-3.99 (m, 2H), 3.81-3.65 (m, 3H), 3.49-3.37 (m, 4H), 2.89-2.78 (m, 2H), 2.31 (s, 1H), 1.75-1.49 (m, 4H), 1.46-1.33 (m, 1H), 1.13 (t, J=7.2 Hz, 1H).

MS (EI) m/z: 422 (M$^+$).

Example 35

(3R,3aS)-7-(6-(5-(aminomethyl)-2-oxooxazolidin-3-yl)pyridin-3-yl)-3-(hydroxylmethyl)-3a,4-dihydrobenzo[b]oxazolo[3,4-d][1,4]oxazin-1(3H)-one (33)

Step 1: Preparation of 5-(azidomethyl)-3-(5-bromopyridin-2-yl)-oxazolidin-2-one (33a)

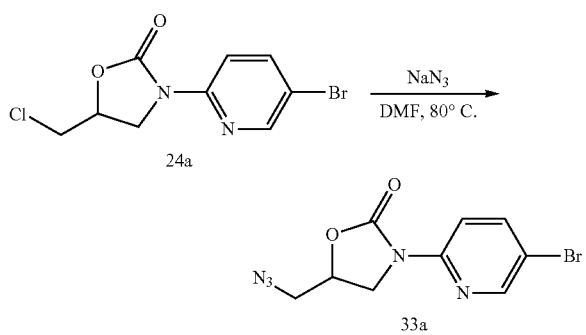

Compound 24a (300 mg, 1.03 mmol) was dissolved in N,N-dimethyl formamide. Sodium azide (100 mg, 1.54 mmol) was added, and the mixture was heated to 80° C. to react for 5 hrs. The reaction was measured by TLC. After the starting materials reacted completely, the reaction mixture was cooled to room temperature, diluted with water, and extracted with ethyl acetate. The organic phase was combined, washed sequentially with water and saturated saline solution, dried over anhydrous sodium sulfate, and filtered. Column chromatography afforded 300 ing of white solid (compound 33a), yield 98%.

$^1$H NMR (300 MHz, CDCl$_3$) δ 8.37 (d, J=2.41 Hz, 1H), 8.18 (d, J=9.0 Hz, 1H), 7.81 (dd, J$_1$=9.0 Hz, J$_2$=2.4 Hz, 1H), 4.85-4.78 (m, 1H), 4.29 (dd, J=10.8 Hz, J$_2$=9.0 Hz, 1H), 4.05 (dd, J$_1$=10.8 Hz, J$_2$=6.2 Hz, 1H), 3.71 (dd, J$_1$=13.3 Hz, J$_2$=4.1 Hz, 1H), 3.60 (dd, J$_1$=13.1 Hz, J$_2$=4.5 Hz, 1H).

MS (EI) m/z: 298 (M$^+$).

Step 2: Synthesis of (3R,3aS)-7-(6-(5-(azidomethyl)-2-oxooxazolidin-3-yl)pyridin-3-(hydroxylmethyl)-3-yl)-3a,4-dihydrobenzo[b]oxazolo[3,4-d][1,4]oxazin-1(3H)-one (33b)

Compound I-3 (100 mg, 0.29 mmol), 33a (131 mg, 0.44 mmol), cesium carbonate (234 mg, 0.72 mmol) and Pd(PPh$_3$)$_4$ (34 mg, 0.029 mmol), under the protection of argon, reacted following the synthetic method of compound 1 to afford 56 mg of white solid (compound 33b), yield 44%.

$^1$H NMR (300 MHz, DMSO) δ 8.69 (d, J=1.9 Hz, 1H), 8.20-8.09 (m, 2H), 7.95 (dd, J$_1$=6.8 Hz, J$_2$=2.4 Hz, 1H), 7.40-7.32 (m, 2H), 5.31 (t, J=5.8 Hz, 1H), 4.98-4.88 (m, 1H), 4.62-4.51 (m, 1H), 4.50-4.40 (m, 1H), 4.31-4.25 (m, 1H), 4.11-4.01 (m, 2H), 3.94 (dd, J$_1$=11.1 Hz, J$_2$=5.8 Hz, 1H), 3.82-3.65 (m, 4H).

MS (EI) m/z: 438 (M$^+$).

Step 3: Preparation of (3R,3aS)-7-(6-(5-(aminomethyl)-2-oxooxazolidin-3-yl)pyridin-3-yl)-3-(hydroxylmethyl)-3a,4-dihydrobenzo[b]oxazolo[3,4-d][1,4]oxazin-1(3H)-one (33)

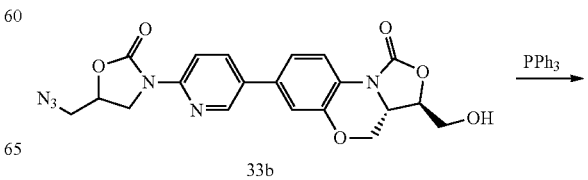

-continued

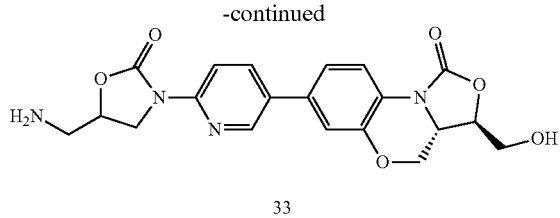

33

Compound 33b (200 mg, 0.46 mmol) and triphenylphosphine (234 mg) reacted following the synthetic method of compound 27d to afford 82 mg of white solid, yield 43%.

$^1$H NMR (300 MHz, DMSO) δ 8.69 (s, 1H), 8.15 (s, 2H), 7.95 (d, J=9.26 Hz, 1H), 7.40-7.29 (m, 2H), 5.33 (s, 1H), 4.70-4.40 (m, 31H), 4.25-4.16 (m, 1H) 4.15-3.92 (m, 3H), 3.85-3.62 (m, 2H), 2.92-2.78 (m, 2H).

MS (EI) m/z: 412 (M$^+$).

Example 36

4-(((3R,3aS)-7-(6-cyanopyridin-3-yl)-1-oxo-1,3,3a,4-tetrahydrobenzo[b]oxazolo[3,4-d][1,4]oxazin-3-yl)methoxyl)-4-oxobutyric acid (34)

Compound 3 (1.0 g, 3.1 mmol) was dissolved in dried N,N-dimethyl formamide (20 mL) and cooled to 0° C. Under the protection of argon, triethylamine (0.86 mL, 6.2 mmol) was added, then succine anhydride (465 mg, 4.7 mmol) was added portionwise. Upon completion of the addition, the reaction mixture was raised to room temperature and allowed to react overnight. TLC (dichloromethane/methanol=20/1) was employed to monitor the reaction. After the reaction completed, the reaction mixture was diluted by adding water (15 mL) and the pH value was adjusted with 1N HCl to 3-4. There was solid precipitated. The solid was dissolved by ethyl acetate. The organic layer was separated, and the aqueous layer was extracted with ethyl acetate (10 mL×2). The organic phase was combined, washed with saturated sodium chloride solution dried over anhydrous sodium sulfate, filtered, and then dried by rotary evaporation. Column chromatography (dichloromethane/methanol=50/1) afforded 1.1 g of white solid (compound 34), yield 82%.

m.p.: 313-315° C.

$^1$H NMR (400 MHz, DMSO) δ 12.27 (s, 1H), 9.10 (s, 1H), 8.34 (d, J=8.2 Hz, 1H), 8.10 (d, J=8.2 Hz, 1H), 8.04 (d, J=8.5 Hz, 1H), 7.55-7.48 (m, 2H), 4.78-4.70 (m, 1), 4.68-4.63 (m, 1H), 4.49-4.39 (m, 2H), 4.18-4.06 (m, 2H), 2.62-2.55 (m, 2H), 2.50-2.46 (m, 2H).

MS (ESI) m/z: 424.3 [M+1]$^+$.

Example 37

Sodium 4-(((3R,3aS)-7-(6-cyanopyridin-3-yl)-1-oxo-1,3,3a,4-tetrahydro-benzo[b]oxazolo[3,4-d][1,4]oxazin-3-yl)methoxyl)-4-oxobutyrate (35)

Sodium bicarbonate (30 mg, 0.36 mmol) was dissolved in water (4 mL). Compound 44 (100 mg, 0.24 mmol) was added portionwise, and the resulting mixture was agitated at 30° C. until it became clear, and then cooled to room temperature. A small amount of floc was filtered out by a microporous membrane filter. The filtrate was added dropwise into acetone (50 ml), at which time some white floc appeared. After the addition was completed, the resulting mixture was agitated for 30 mins, cooled to 0° C., stand still, filtered, and oven dried to afford 48 mg of white powder (compound 45), yield 45%.

$^1$H NMR (400 MHz, D$_2$O) δ9.10 (s, 1H), 8.34 (d, J=8.2 Hz, 1H), 8.10 (d, J=8.2 Hz, 1H), 8.04 (d, J=8.5 Hz, 1H), 7.55-7.48 (m, 2H), 4.78-4.70 (m, 1H), 4.68-4.63 (m, 1H), 4.49-4.39 (m, 2H), 4.18-4.06 (m, 2H), 2.62-2.55 (m, 2H), 2.50-2.46 (m, 2H).

Example 38

Disodium(((3R,3aS)-7-(6-cyanopyridin-3-yl)-1-oxo-1,3,3a,4-tetrahydro benzo[b]oxazolo[3,4-d][1,4]oxazin-3-yl)methyl)phosphate (36)

Step 1: Preparation of dibenzyl(((3R,3aS)-7-(6-cyanopyridin-3-yl)-1-oxo-1,3,3a,4-tetrahydrobenzo[b]oxazolo[3,4-d][1,4]oxazin-3-yl)methyl)phosphate (3-PBn)

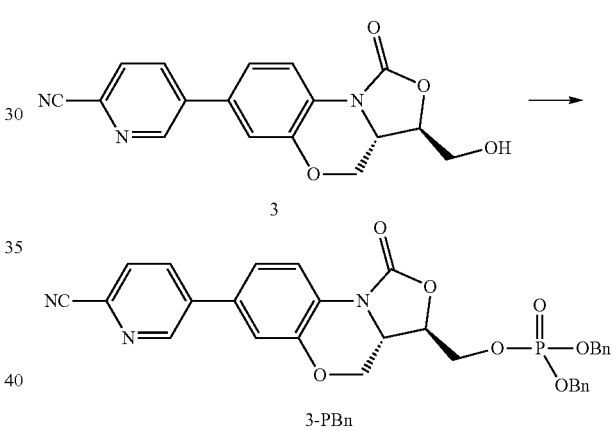

Compound 3 (500 mg, 1.55 mmol) and 4,5-dicyanoimidazole (400 mg, 3.39 mmol) was suspended in dried dichloromethane, cooled to 0° C., and dibenzyl N,N'-diisopropylphosphoramidite (1.09 mL, 3.26 mmol) was added. The resulting mixture was raised to room temperature and allowed to react for 4 hrs. The reaction was measured by TLC. After the reaction completed, the reaction mixture was cooled to 0° C. Then the solution of m-chloro-peroxybenzoic acid (401 mg, 2.32 mmol) in dichloromethanen was added dropwise. After the reaction completed, saturated solution of sodium sulfite was added. The organic phase was washed sequentially with saturated solution of sodium bicarbonate, water and saturated saline solution, dried over anhydrous sodium sulfate, and filtered. Column chromatography afforded 678 mg of white solid (compound 3-PBn), yield 75%.

$^1$H NMR (400 MHz, DMSO) δ 9.11 (d, J=2.3 Hz, 1H), 8.35 (dd, J=8.2, 2.3 Hz, 1H), 8.11 (d, J=8.2 Hz, 1H), 7.98 (d, J=8.1 Hz, 1H), 7.57-7.50 (m, 2H), 7.42-7.30 (m, 10H), 5.09 (s, 2H), 5.07 (s, 2H), 4.74-4.69 (m, 1H), 4.64-4.58 (m, 1H), 4.47-4.40 (m, 1H), 4.39-4.32 (m, 1H), 4.13-4.01 (m, 2H).

MS (EI) m/z: 583 (M)$^+$.

Step 2: Preparation of (((3R,3aS)-7-(6-cyanopyridin-3-yl)-1-oxo-1,3,3a,4-tetrahydrobenzo[b]oxazolo[3,4-d][1,4]oxazin-3-yl)methyl)phosphate (3-P)

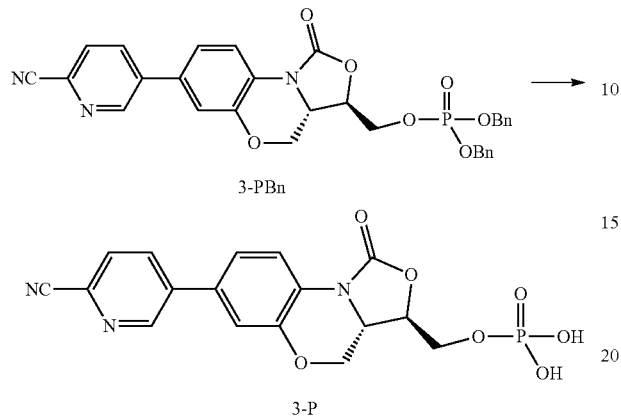

Compound 3-PBn (100 mg, 0.17 mmol) was dissolved in MeOH/tetrahydrofuran mixed solvent. The mixture was flushed with argon, followed by addition of 10% Pd/C (30 mg). The mixture was then flushed with hydrogen and subjected to hydrogenation overnight at normal pressure and temperature. TLC (dichloromethane/methanol=20/1) was employed to monitor the reaction. After the reaction completed, the reacture mixture was filtered. The filter cake was washed with N,N-dimethyl formamide and the filtrate was dried by rotary evaporation to afford 44 mg of pale yellow solid (compound 3-P), yield 65%.

$^1$H NMR (300 MHz, DMSO) δ 8.92 (s, 1H), 8.25 (dd, J=8.2, 1.8 Hz, 1H), 8.12 (s, 1H), 8.10-7.97 (m, 2H), 7.66 (s, 1H), 7.54-7.43 (m, 2H), 4.65 (M, 2H), 4.23-4.02 (m, 4H).

Step 3: Preparation of disodium(((3R,3aS)-7-(6-cyanopyridin-3-yl)-1-oxo-1,3,3a,4-tetrahydrobenzo[b]oxazolo[3,4-d][1,4]oxazin-3-yl)methyl)phosphate (36)

Sodium isooctoate (101 mg, 0.6 mmol) was dissolved in water (2 mL) and compound 3-P (80 mg, 0.2 mmol) was added portionwise. The mixture was agitated at room temperature for 2 hrs until the mixture became substantially clear, then raised to 40° C. to react for 30 mins, and cooled. A small amount of floc was filtered out by a microporous membrane tilter. The filtrate was added dropwise into acetone (100 ml) and there was solid precipitated out continuously. After the addition was completed, the resulting mixture was agitated for 1 hr. filtered after standing still for 2 hrs. The filter cake was washed with acetone and dried to afford 56 mg of white solid (compound 43), yield 63%.

$^1$H NMR (300 MHz, DMSO) δ 8.91 (s, 1H), 8.23 (dd, J=8.2, 1.8 Hz, 1H), 8.11 (s, 1H), 8.11-7.98 (m, 2H), 7.64 (s, 1H), 7.54-7.43 (m, 2H), 4.63 (M, 2H), 4.23-4.02 (m, 4H).

Example 39

Disodium ((3R,3aS)-7-(6-(3-methyl-2-oxazolidino-5-yl)pyridin-3-yl)-1-oxo-1,3,3a,4-tetrahydrobenzo[b]oxazolo[3,4-d][1,4]oxazin-3-yl)methyl)phosphate (37)

Step 1: Preparation of dibenzyl(((3R,3aS)-7-(6-(3-methyl-2-oxazolidino-5-yl)pyridin-3-yl)-1-oxo-1,3,3a,4-tetrahydrobenzo[b]oxazolo[3,4-d][1,4]oxazin-3-yl)methyl)phosphate (14-PBn)

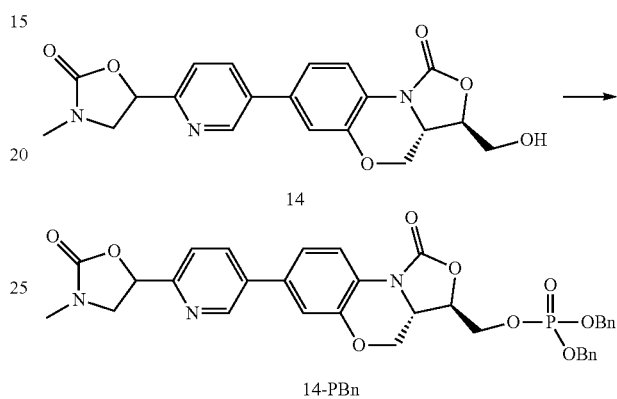

Compound 14 (500 mg, 1.26 mmol), 4,5-dicyanoimidazole (325 mg, 2.75 mmol), dibenzyl N,N'-diisopropylphosphoramidite (0.89 mL, 2.65 mmol) and m-chloro-peroxybenzoic acid (326 mg, 1.89 mmol) reacted following the synthetic method of compound 3-PBn to afford 593 mg of white solid (compound 14-PBn), yield 71.5%.

$^1$H NMR (400 MHz, CD$_3$OD) δ 8.93 (d, J=1.9 Hz, 1H), 8.15 (dd, J=8.3, 2.2 Hz, 1H), 7.94 (d, J=9.0 Hz, 1H), 7.55 (d, J=8.2 Hz, 1H), 7.44-7.29 (m 12H), 5.63 (dd, J=8.9, 6.4 Hz, 1H), 5.08 (s, 2H), 5.06 (s, 2H), 4.70 (s, 1H), 4.60 (d, J=8.1 Hz, 1H), 4.47-4.40 (m, 1H), 4.39-4.31 (m, 1H), 4.12-4.01 (m, 2H), 4.00-3.93 (m, 1H), 3.74-3.66 (m, 1H), 2.81 (s, 3H).

MS (ESI) m/z: 680.3 [M+Na]$^+$.

Step 2: Preparation of ((3R,3aS)-7-(6-(3-methyl-2-oxazolidino-5-yl)pyridin-3-yl)-1-oxo-1,3,3a,4-tetrahydrobenzo[b]oxazolo[3,4-d][1,4]oxazin-3-yl)methyl)phosphate (14-P)

Compound 14-PBn (500 mg, 0.76 mmol) was dissolved in MeOH/tetrahydrofuran mixed solvent. The mixture was flushed with argon, and then 10% Pd/C (100 mg) was added. The mixture was then flushed with hydrogen and subjected to hydrogenation overnight at normal pressure and temperature. TLC (dichloromethane/methanol=20/1) was employed to monitor the reaction. After the reaction completed, the reacture mixture was filtered. The filter cake was washed with N,N-dimethyl formamide and the filtrate was dried by spinning to afford 290 mg of pale yellow solid (compound 14-P), yield 80%.

$^1$H NMR (300 MHz, DMSO) δ 8.93 (d, J=5.7 Hz, 1H), 8.15 (dd, J=8.1, 2.2 Hz, 1H), 8.02-7.92 (m, 1H), 7.55 (d, J=8.2 Hz, 1H), 7.49-7.34 (m, 2H), 5.63 (dd, J=8.8, 6.3 Hz, 1H), 4.72-4.57 (m, 2H), 4.26-4.15 (m, 2H), 4.14-4.05 (m, 2H), 3.97 (t, J=8.9 Hz, 1H), 3.74-3.65 (m, 1H), 2.81 (s, 3H).

MS (ESI) m/z: 478.3 [M+1]$^+$.

Step 3: Preparation of disodium((3R,3aS)-7-(6-(3-methyl-2-oxazolidino-5-yl)pyridin-3-yl)-1-oxo-1,3,3a,4-tetrahydrobenzo[b]oxazolo[3,4-d][1,4]oxazin-3-yl)methyl)phosphate (37)

Sodium isooctoate (172 mg, 1.03 mmol) and compound 14-P (165 mg, 0.34 mmol) reacted following the synthetic method of compound 43 to afford 120 mg of white solid (compound 37), yield 68%.

$^1$H NMR (300 MHz, DMSO) δ 8.93 (d, J=5.7 Hz, 1H), 8.15 (dd, J=8.1, 2.2 Hz, 1H), 8.02-7.92 (m, 1H), 7.55 (d, J=8.2 Hz, 1H), 7.49-7.34 (m, 2H), 5.63 (dd, J=8.8, 6.3 Hz, 1H), 4.72-4.57 (m, 2H), 4.26-4.15 (m, 2H), 4.14-4.05 (m, 2H), 3.97 (t, J=8.9 Hz, 1H), 3.74-3.65 (m, 1H), 2.81 (s, 3H).

Example 40

((3R,3aS)-7-(6-(3-methyl-2-oxazolidino-5-yl)pyridin-3-yl)-1-oxo-1,3,3a,4-tetrahydrobenzo[b]oxazolo[3,4-d][1,4]oxazin-3-yl)methyl)phosphate-diarginine salt (38)

Compound 14-P (110 mg, 0.23 mmol) and arginine (120 mg, 0.69 mmol) reacted following the synthetic method of compound 37 to afford 120 mg of white solid (compound 38), yield 63%.

$^1$H NMR (300 MHz, DMSO) δ 8.93 (d, J=5.7 Hz, 1H), 8.15 (dd, J=8.1, 2.2 Hz, 1H), 8.02-7.92 (m, 1H), 7.55 (d, J=8.2 Hz, 1H), 7.49-7.34 (m, 2H), 5.63 (dd, J=8.8, 6.3 Hz, 1H), 4.72-4.57 (m, 2H), 4.26-4.15 (m, 2H), 4.14-4.05 (m, 2H), 3.97 (t, J=8.9 Hz, 1H), 3.74-3.65 (m, 1H), 2.81 (s, 3H).

Example 41

Disodium ((3R,3aS)-7-(6-((R)3-methyl-2-oxazolidino-5-yl)pyridin-3-yl)-1-oxo-1,3,3a,4-tetrahydrobenzo[b]oxazolo[3,4-d][1,4]oxazin-3-yl)methyl)phosphate (39)

Following the preparation method of compound 36, compound 27 was used as starting material to afford compound 39.

$^1$H NMR (300 MHz, DMSO) δ 8.93 (d, J=5.7 Hz, 1H), 8.15 (dd, J=8.1, 2.2 Hz, 1H), 8.02-7.92 (m, 1H), 7.55 (d, J=8.2 Hz, 1H), 7.49-7.34 (m, 2H), 5.63 (dd, J=8.8, 6.3 Hz, 1H), 4.72-4.57 (m, 2H), 4.26-4.15 (m, 2H), 4.14-4.05 (m, 2H), 3.97 (t, J=8.9 Hz, 1H), 3.74-3.65 (m, 1H), 2.81 (s, 3H).

Example 42

Disodium(3-(5-((3R,3aS)-3-(hydroxylmethyl)-1-oxo-1,3,3a,4-tetrahydrobenzo[b]oxazolo[3,4-d][1,4]oxazin-7-yl)pyridin-2-yl)-2-oxazolidino-5-yl)methyl)phosphate (40)

Step 1: Dibenzyl((3-(5-bromopyridin-2-yl)-2-oxazolidino-5-yl)methyl)phosphate (40a)

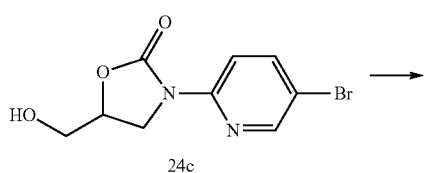

24c

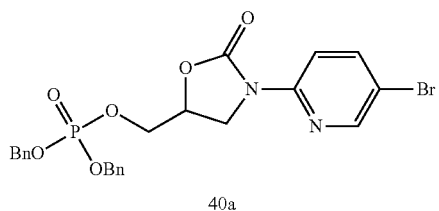

40a

Compound 24c (1.0 g, 3.66 mmol), 4,5-dicyanoimidazole (944 mg, 7.99 mmol), dibenzyl N,N'-diisopropylphosphoramidite (2.58 mL, 7.7 mmol), and m-chloro-peroxybenzoic acid (947 mg, 5.5 mmol) reacted following the synthetic method of compound 3-PBn to afford 1.8 g of colorless viscous liquid (compound 40a), yield 92%.

$^1$H NMR (300 MHz, CDCl$_3$) δ 8.33 (d, J=2.3 Hz, 1H), 8.08 (d, J=9.0 Hz, 1H), 7.75 (dd, J1=9.0, J2=2.4 Hz, 1H), 7.40-7.23 (m, 10H), 5.10-4.96 (m, 5H), 4.72 (di, J1=14.3, J2=4.9 Hz, 1H), 4.23-4.06 (m, 3H).

MS (ESI) m/z: 555.3 [M+Na]$^+$.

Step 2: Dibenzyl((3-(5-((3R,3aS)-3-(hydroxylmethyl)-1-oxo-1,3,3a,4-tetrahydrobenzo[b]oxazolo[3,4-d][1,4]oxazin-7-yl)pyridin-2-yl)-2-oxazolidino-5-yl)methyl)phosphate (40b)

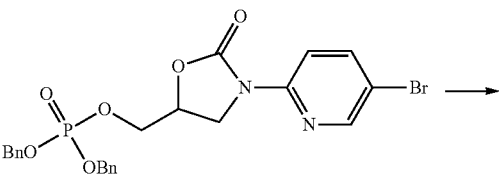

40a

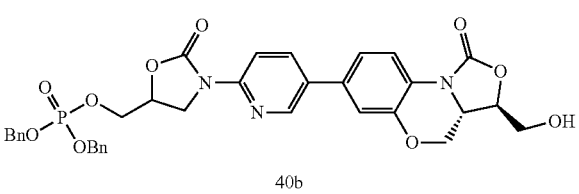

40b

Compound I-3 (124 mg, 0.23 mmol), compound 40a (97.2 mg, 0.28 mmol), cesium carbonate (190 mg, 0.58 mmol) and Pd(PPh$_3$)$_4$ (27 mg, 0.023 mmol) reacted following the synthetic method of compound 1 to afford 53 mg of white solid (compound 40b), yield 34%.

$^1$H NMR (300 MHz, DMSO) δ 8.68 (s, 1H), 8.18-8.10 (m, 2H), 7.96 (d, J=9.1 Hz, 1H), 7.45-7.18 (m, 12H), 5.33 (t, J=5.7 Hz, 1H), 5.04-4.95 (m, 5H), 4.64-4.53 (m, 1H), 4.52-4.44 (m, 1H), 4.39-4.20 (m, 3H), 4.13-3.97 (nm, 3H), 3.82-3.64 (m, 2H).

MS (ESI) m/z: 696.2 [M+Na]$^+$.

Step 3: (3-(5-((3R,3aS)-3-(hydroxylmethyl)-1-oxo-1,3,3a,4-tetrahydrobenzo[b]oxazolo[3,4-d][1,4]oxazin-7-yl)pyridin-2-yl)-2-oxazolidino-5-yl)methyl)phosphate (40c)

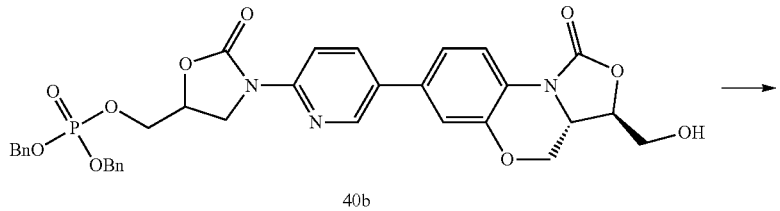

40b

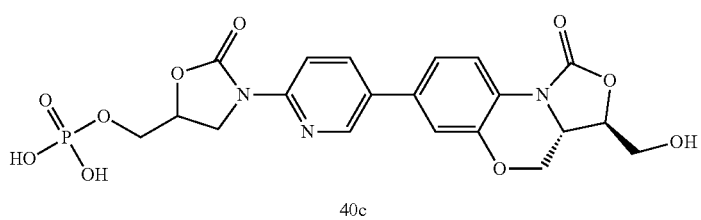

40c

Compound 40b (500 mg, 0.74 mmol) and 10% Pd/C (100 mg) reacted following the synthetic method of compound 3-P to afford 314 mg of pale yellow solid (compound 40c), yield 86%.

$^1$H NMR (300 MHz, DMSO) δ 8.68 (s, 1H), 8.16-8.12 (m, 2H), 7.95 (d, J=9.1 Hz, 1H), 7.39-7.33 (m, 2H), 4.97-4.87 (m, 1H), 4.64-4.53 (m, 1H), 4.50-4.42 (m, 1H), 4.34-4.21 (m, 1H), 4.15-3.96 (m, 5H), 3.80-3.66 (m, 2H).

MS (ESI) m/z: 492.0 [M−1]$^+$.

Step 4: Disodium(3-(5-((3R,3aS)-3-(hydroxylmethyl)-1-oxo-1,3,3a,4-tetrahydrobenzo[b]oxazolo[3,4-d][1,4]oxazin-7-yl)pyridin-2-yl)-2-oxazolidino-5-yl)methyl)phosphate (40)

Sodium isooctoate (152 mg, 0.91 mmol) and compound 40c (150 mg, 0.30)) reacted following the synthetic method of compound 36 to afford 75 mg of white solid (compound 40), yield 47%.

$^1$H NMR (300 MHz, D$_2$O) δ 8.12 (s, 1H), 7.95 (d, J=9.1 Hz, 1H), 7.39-7.33 (m, 2H), 4.97-4.87 (m, 1H), 4.64-4.53 (m, 1H), 4.50-4.42 (m, 1H), 4.34-4.21 (m, 1H), 4.15-3.96 (m, 5H), 3.80-3.66 (m, 2H).

Example 41

(3-(5-((3R,3aS)-3-(hydroxylmethyl)-1-oxo-1,3,3a,4-tetrahydrobenzo[b]oxazolo[3,4-d][1,4]oxazin-7-yl)pyridin-2-yl)-2-oxazolidino-5-yl)methyl)phosphat-diarginine salt (41)

Compound 40c (50 mg, 0.1 mmol) and L-arginine (52 mg, 0.3 mmol) reacted following the synthetic method of compound 43 to afford 52 mg of white solid (compound 41), yield 62%.

$^1$H-NMR (300 MHz, D$_2$O) δ 8.12 (s, 1H), 7.95 (d, J=9.1 Hz, 1H), 7.39-7.33 (m, 2H), 4.97-4.87 (m, 1H), 4.64-4.53 (m, 1H), 4.50-4.42 (m, 1H), 4.34-4.21 (m, 1H), 4.15-3.96 (m, 5H), 3.80-3.66 (m, 2H).

II. EXPERIMENTAL EXAMPLES

1. In Vitro Antibacterial Activity Assay of the Compounds of the Present Invention Experimental method: The agar double dilution method (Antimicrob. Agents and Chemother, 40, 1996, 720-726) was used to determine the minimum inhibitory concentration (MIC) of the series of compounds of the invention and the positive control drug linezolid for the test strains. The multi-point inoculation system (Denley A400) was employed to inoculate the bacteria on the agar plate surface with different concentrations of drugs; inoculation amount on each point was about 10$^6$ CFU/mL. The plates were incubated at 35° C. for 16 hrs before the results were observed. The lowest drug concentration contained in the Petri dish without bacterial growth was used as the minimum inhibitory concentration (MIC value) of the drug fir that strain.

Test strains: All the test strains were clinically isolated pathogens which were collected from the Nanjing region, and they were re-identified by routine methods before use. 31 strains of the clinically isolated pathogens were chosen, including 6 strains of *Enterococcus*, 5 *Staphylococcus aureus* sensitive strains; 5 *Staphylococcus epidermidis* sensitive strains; 6 *Staphylococcus aureus* resistant strains; 5 *Staphylococcus epidermidis* resistant strains; and 4 *Streptococcus pneumoniae* resistant strains.

Compounds to be tested were first added 2 ml of DMSO to help them fully dissolved, then added sterile double distilled water to the desired concentration; to all the Petri dish with added drug liquid were added 20 mL MIT medium which was heat-melted to be liquid-like, to make the final drug concentration in the Petri dish to be 64, 32, 16, 8, 4, 2, 1, 0.5, 0.25, 0.125, 0.0625, and 0.031 μg/mL.

The positive control group was LZ (linezolid, brand name Zyvox, approved by the FDA in 2000 to be firstly sold in the United States, which is the first and also the only one of oxazolidinone antibacterial drugs allowed to enter clinical application).

TABLE 2

MIC value (μg/mL) of the compounds of the present invention for the test strains

| Compound | Enterococcus (6 strains) | Staphylococcus aureus sensitive strains (5 strains) | Staphylococcus epidermidis sensitive strains (5 strains) | Staphylococcus aureus resistant strains (6 strains) | Staphylococcus epidermidis resistant strains (5 strains) | Streptococcus pneumoniae resistant strains (4 strains) |
|---|---|---|---|---|---|---|
| 1 | 1 | 0.25 | 0.125-0.5 | 0.125-0.5 | 0.125-0.5 | 0.25-0.5 |
| 2 | 1-2 | 0.5-1 | 0.5-1 | 0.5-1 | 0.5-1 | 0.5-2 |
| 3 | 1 | 0.25-0.5 | 0.25 | 0.125-0.25 | 0.125-0.25 | 0.25-0.5 |
| 4 | 1-2 | 0.5-1 | 0.5 | 0.5-1 | 0.5 | 1-2 |
| 5 | 1 | 0.5-1 | 0.5-1 | 0.5-1 | 0.5-1 | 0.5-1 |
| 6 | 2 | 1 | 0.5-1 | 1-2 | 1 | 1-2 |
| 7 | 4 | 1-4 | 1-4 | 1-4 | 2 | 2-4 |
| 8 | 2-4 | 1-2 | 1 | 1-2 | 1-2 | 2-4 |
| 9 | 4 | 1-2 | 0.5 | 1-2 | 0.5-1 | 2-4 |
| 10 | 2-4 | 2 | 1-2 | 1-2 | 1-2 | 2 |
| 11 | 16 | 2-4 | 2-4 | 4 | 8 | 2-8 |
| 12 | 2-4 | 2-4 | 2-4 | 4-8 | 4 | 4 |
| 13 | 2 | 2-4 | 4 | 2-4 | 4-8 | 8-16 |
| 14 | 1-2 | 0.5-1 | 0.25-0.5 | 0.5-1 | 0.25-1 | 1 |
| 15 | 1-2 | 1-2 | 1-2 | 1-2 | 2-4 | 2 |
| 16 | 1-2 | 1-2 | 1-2 | 1-2 | 2-4 | 2 |
| 17 | 4 | 1-4 | 1-2 | 1-2 | 1-2 | 1-2 |
| 18 | 4-8 | 2-4 | 1-2 | 2 | 1-2 | 2-4 |
| 19 | 2-4 | 2-4 | 1-2 | 2-4 | 2-4 | 2-4 |
| 20 | 16-32 | 2-4 | 2-4 | 2-4 | 2-4 | 4-8 |
| 21 | 4-8 | 0.25-0.5 | 0.25-0.5 | 0.5-1 | 0.25-1 | 1-2 |
| 22 | 4-16 | 0.5-1 | 0.5-1 | 0.5-1 | 1 | 2 |
| 23 | 16 | 8 | 4-8 | 8 | 8-16 | 16 |
| 24 | 0.5-1 | 0.5-1 | 0.25-0.5 | 0.5-1 | 0.5-1 | 1 |
| 25 | 0.5-1 | 0.5-1 | 0.5-1 | 0.5-1 | 0.5-1 | 1 |
| 26 | 0.5-1 | 0.5-1 | 0.5-1 | 0.5-1 | 0.5-1 | 1 |
| 27 | 1 | 1 | 1 | 1 | 0.5-1 | 0.25-0.5 |
| 28 | 2 | 2 | 2 | 2 | 1-2 | 2 |
| 29 | 2 | 2-4 | 1 | 1 | 1-2 | 1-2 |
| 30 | 4-8 | 2-4 | 1-2 | 2-4 | 0.5-4 | 4-16 |
| 31 | 16 | 2-4 | 2-4 | 2-4 | 2-4 | 4 |
| 32 | 16 | 4-8 | 4-8 | 8 | 4-8 | 8-16 |
| 33 | 1-2 | 1-2 | 0.5-1 | 1-2 | 2 | 2 |
| LZ | 1-2 | 1-2 | 1 | 1-2 | 1-2 | 2 |

The experimental data in Table 2 show that the compounds of the present invention have very strong antimicrobial activity in vitro, which is significantly superior to the positive control drug linezolid (LZ). Stronger antibacterial activity indicates that a lower dosage can be used, thereby reducing the toxic side effects accompanying the higher dosage of linezolid. Therefore, the compounds or the present invention have higher therapeutic effectiveness and safety.

2. In Vitro Antibacterial Activity Assay of the Compounds of the Present Invention on Linezolid-Resistant Strains Experimental Methods 1) Preparation of the Subject Drugs and Medium The stock solution of the subject drugs in DMSO was 10 mg/mL. MHA (agar) and MHB (broth) were both prepared according to the manufacturer's requirements.

2) Preparation of the Gradient Solution of the Subject Drugs

Double dilution of drugs: under aseptic operation, 12.8 μL of liquid drug was added into the first well of a 96-well plate, and then added 27.2 μL DMSO and mixed. The $2^{nd}$ to $12^{nd}$ wells were all added 20 μL DMSO. 20 μL was taken from the first well to the second well and mixed up. 20 μL was taken from the second well to the third well, which was repeated till the $11^{st}$ well, from which was taken 20 μL and discarded. The $12^{nd}$ well only had 20 μL of DMSO as the growth control. Then 180 μL of sterile water was added to each well and mixed up. The drug used as control was prepared by the same method.

The solutions with different concentrations of antibacterial drugs after the double dilution and DMSO were added into a sterile 96-well plate separately, 10 μL per well, ready for use.

3) Preparation of the Test Strains and the MIC Assay

Single colonies were picked from the MHA plates into 5 ml of sterile saline and mixed up.

Light transmittance was adjusted to 80% with a spectrophotometer. After being diluted by 1:200 with MHB, 90 μL of such bacteria liquid was added into each of the wells which already had 10 μL of the drug liquid, mixed up, and incubated in a regular biochemical incubator at 35° C. for 20 hrs before the results were read out. At this time, the drug concentration in the $1^{st}$ to $12^{nd}$ wells was 32, 16, 8, 4, 2, 1, 0.5, 0.25, 0.125, 0.0625, 0.03125, 0 μg/mL, respectively.

Two parallel groups were set up for the same diluted concentration of a drug.

4) Results Reading and Judgment: Refer to the Standard Recommended by the CLSI, 2010 Edition.

The positive control group was LZ (linezolid, brand name Zyvox, approved by the FDA in 2000 to be firstly sold in the United States, which is the first and also the only one of oxazolidinone antibacterial drugs allowed to enter clinical application).

TABLE 3

In vitro activity MIC (μg/mL) of the compounds of the present invention on linezolid-resistant strains

| Compound | S.a. ATCC 29213 | LRSA (3 strains) | LRSE (1 strain) | LREFL (3 strains) | LREFA (3 strains) |
|---|---|---|---|---|---|
| 1 | 0.5 | 8 | 4 | 8 | 4-8 |
| 2 | 0.5 | 8 | 4 | 4-8 | 4-8 |
| 3 | 0.25 | 4-8 | 4 | 4 | 2-4 |
| 5 | 0.5 | 4 | 2 | 4-8 | 4-8 |
| 18 | 0.5 | 4 | 4 | 2-4 | 2-4 |
| 34 | 0.5 | 8 | 4 | 4 | 4 |
| LZ | 1 | >32 | 16 | 8-16 | 8-16 |

Note:
SAU 1011 is the standard strain of *Staphylococcus aureus*, ATCC 29213;
MASU 0071~0073 is a linezolid-resistant strain of *Staphylococcus aureus*;
MSEP 0006 is a linezolid-resistant strain of *Staphylococcus epidermidis*;
MEFL 0039~0041 is a linezolid-resistant strain of *Enterococcus faecalis*;
MEFA 0038~0040 is a linezolid-resistant strain of *Enterococcus faecium*.

The data in Table 3 show that the compounds of the present invention also have excellent in vitro antibacterial activity on linezolid-resistant strains compared with the positive control drug linezolid, thereby providing a good solution for the clinically increasing resistance problems of bacteria to linezolid.

3. In Vivo Pharmacokinetic Assays of the Compounds of the Present Invention in Rats 3.1 The In Vivo Pharmacokinetic Properties of Compound 14 in Rats Two routes of administration (intragastric administration and intravenous injection) were employed.

Intragastric administration: Four healthy SD rats, male, weight 200-250 g, were dosed 15 mg/kg; the delivery volume was 10 ml/kg, prepared with 0.5% CMC-Na. The rats were fasted for 12 hrs before administration, free water-drinking. 0.3 ml of venous blood was taken from the posterior venous plexus of rats to heparinized tubes at 0.25, 0.5, 1.0, 2.0, 3.0, 4.0, 5.0, 7.0, 9.0, 24, and 48 hrs after administration, centrifuged at 3500 rpm for 10 mins to separate the plasma, which was then stored at −20° C. for test.

Intravenous injection: Two healthy SD rats, male, weight 200~250 g, were dosed 5 mg/kg; the delivery volume was 10 ml/kg, prepared with DMSO, Tween 80 and deionized water. The rats were fasted for 12 hrs before administration, free water-drinking. 0.3 ml of venous blood was taken from the posterior venous plexus of rats to heparinized tubes at 5 min, 15 min, and 0.5, 1.0, 2.0, 3.0, 4.0, 5.0, 7.0, 9.0, 24, and 48 hrs after administration, centrifuged at 3500 rpm for 10 mins to separate the plasma, which was then stored at −20° C. for test.

The concentration of Compound 14 in plasma was determined by liquid chromatography tandem mass spectrometry. The Experimental apparatus are shown in Table 4.

TABLE 4

Experimental apparatus

| | |
|---|---|
| Liquid chromatography system: | Agilent 1200 Liquid Chromatography System (including G1322A dual infusion pump, G1316B column oven, and G1312B vacuum degassing machine), Agilent company, U.S. |
| Automatic sampler: | G1367D Automatic Sampler., Agilent company, U.S. |
| MS/MS system: | Agilent 6460 triple quadrupole tandem mass spectrometer equipped with electrospray ionization source (ESI source), Agilent company, U.S. |

TABLE 4-continued

Experimental apparatus

| | |
|---|---|
| Data collection: | MassHunter Data AcquistionSoftware, version B.01.04, Agilent company, U.S. |

The pharmacokinetic parameters after the administration of Compound 14 to rats via intragastric and intravenous administration were shown in Table 5 and Table 6.

TABLE 5

The pharmacokinetic parameters after administering 15 mg/kg of Compound 14 to rats via intragastric administration.

| Animal No. | $T_{max}$ (h) | $C_{max}$ (ng/ml) | $AUC_{0-t}$ (ng·h/ml) | $AUC_{0-\infty}$ (ng·h/ml) | MRT (h) | $t_{1/2}$ (h) | F (%) |
|---|---|---|---|---|---|---|---|
| 15 | 0.50 | 766 | 2174 | 2290 | 2.93 | 1.64 | |
| 16 | 1.0 | 878 | 2095 | 2165 | 2.03 | 2.34 | |
| 17 | 0.50 | 1117 | 2374 | 2440 | 2.23 | 1.45 | |
| 18 | 2.00 | 474 | 1620 | 1772 | 3.36 | 2.29 | |
| Average value | 1.00 | 809 | 2066 | 2167 | 2.64 | 1.93 | 44.8 |
| Standard deviation | 0.71 | 267 | 319 | 286 | 0.62 | 0.45 | |
| CV % | 70.7 | 33.0 | 15.5 | 13.2 | 23.4 | 23.3 | |

TABLE 6

The pharmacokinetic parameters after administering 5 mg/kg of Compound 14 to rats via intravenous injection.

| Animal No. | $AUC_{0-t}$ (ng·h/ml) | $AUC_{0-\infty}$ (ng·h/ml) | MRT (h) | $t_{1/2}$ (h) | CLz (L/h/kg) | Vss (L/kg) |
|---|---|---|---|---|---|---|
| 19 | 1595 | 1603 | 0.61 | 1.62 | 3.12 | 1.90 |
| 20 | 1490 | 1510 | 0.79 | 2.46 | 3.31 | 2.62 |
| 21 | 1526 | 1555 | 0.82 | 3.45 | 3.22 | 2.64 |
| Average value | 1537 | 1556 | 0.74 | 2.51 | 3.22 | 2.39 |
| Standard deviation | 54 | 46 | 0.11 | 0.92 | 0.10 | 0.42 |
| CV % | 3.5 | 3.0 | 15.5 | 36.5 | 3.0 | 17.7 |

After the rats were given 15 mg/kg of Compound 14 via intragastric administration, the plasma peak concentration $C_{max}$ of Compound 14 was 809±267 ng/ml; the peak time $T_{max}$ was 1.00±0.71 h; the area under curve $AUC_{0-t}$ was 2066±319 ng·h/ml; the half life $t_{1/2}$ was 1.93±0.45 h. After the administration of 5 mg/kg of Compound 14 via intravenous injection, the area under curve $AUC_{0-t}$ was 1537±54 ng·h/ml; the half life $t_{1/2}$ was 2.51±0.92 h; the plasma clearance CLz was 3.22±0.10 L/h/kg; the distribution volume Vss was 2.39±0.42 L/kg.

Upon dose correction, the absolute bioavailability after administering 15 mg/kg Compound 14 to rats via intragastric administration was 44.8%.

It can be seen from the experimental data that Compound 14 of the present invention exhibited superior metabolic properties with various ideal metabolic parameters. Good oral bioavailability ensures a higher in vivo blood drug concentration upon oral administration of this compound, and the concentration is much higher than its minimum inhibitory concentration (MIC); and meanwhile, a longer half life indicates that its frequency of administration can be reduced to once a day from twice a day currently used for linezolid, thereby increasing compliance of patients.

In accordance with the above experimental methods, the inventor has determined the in vivo pharmacokinetic properties of phosphate (ester) disodium salt 37 of Compound 14 in rats. The results were shown in Table 7 to Table 9.

TABLE 7

The pharmacokinetic parameters of 14 after administering 10 mg/kg of Compound 37 to rats via intragastric administration.

| Animal No. | $T_{max}$ (h) | $C_{max}$ (ng/ml) | $AUC_{0-t}$ (ng·h/ml) | $AUC_{0-\infty}$ (ng·h/ml) | MRT (h) | $t_{1/2}$ (h) | F (%) |
|---|---|---|---|---|---|---|---|
| 1 | 1.0 | 556 | 1777 | 1803 | 3.94 | 4.67 | |
| 2 | 0.25 | 499 | 1469 | 1487 | 3.59 | 4.65 | |
| 3 | 0.25 | 484 | 1746 | 1772 | 4.31 | 4.58 | |
| 4 | 0.25 | 558 | 1582 | 1600 | 3.56 | 4.53 | |
| Average value | 0.44 | 524 | 1643 | 1665 | 3.85 | 4.61 | 52.5 |
| Standard deviation | 0.38 | 38 | 145 | 149 | 0.35 | 0.07 | |
| CV % | 85.7 | 7.3 | 8.8 | 8.9 | 9.1 | 1.4 | |

TABLE 8

The pharmacokinetic parameters of 14 after administering 50 mg/kg of Compound 37 to rats via intragastric administration.

| Animal No. | $T_{max}$ (h) | $C_{max}$ (ng/ml) | $AUC_{0-t}$ (ng·h/ml) | $AUC_{0-\infty}$ (ng·h/ml) | MRT (h) | $t_{1/2}$ (h) |
|---|---|---|---|---|---|---|
| 1 | 0.25 | 4019 | 11512 | 11524 | 4.06 | 2.51 |
| 2 | 0.25 | 2763 | 6534 | 7190 | 3.02 | 1.98 |
| 3 | 0.25 | 3669 | 9119 | 9133 | 3.31 | 2.84 |
| 4 | 0.50 | 3993 | 7468 | 7827 | 2.37 | 1.96 |
| Average value | 0.31 | 3611 | 8658 | 8918 | 3.19 | 2.32 |
| Standard deviation | 0.13 | 587 | 2182 | 1916 | 0.70 | 0.43 |
| CV % | 40.0 | 16.3 | 25.2 | 21.5 | 21.9 | 18.5 |

TABLE 9

The pharmacokinetic parameters of 14 after administering 10 mg/kg of Compound 37 to rats via intravenous injection.

| Animal No. | $AUC_{0-t}$ (ng·h/ml) | $AUC_{0-\infty}$ (ng·h/ml) | MRT (h) | $t_{1/2}$ (h) | CLz (L/h/kg) | Vss (L/kg) |
|---|---|---|---|---|---|---|
| 5 | 3025 | 3064 | 0.82 | 2.21 | 2.48 | 2.02 |
| 6 | 3520 | 3546 | 1.37 | 5.57 | 2.14 | 2.93 |
| 7 | 2846 | 2884 | 1.56 | 6.87 | 2.64 | 4.12 |
| Average value | 3131 | 3165 | 1.25 | 4.88 | 2.42 | 3.03 |
| Standard deviation | 349 | 342 | 0.39 | 2.41 | 0.25 | 1.05 |
| CV % | 11.1 | 10.8 | 31.0 | 49.3 | 10.4 | 34.7 |

After the rats were given 10 mg/kg 37 via intragastric administration, it was absorbed quickly. The peak time Tmax was 0.44±0.38 h: the plasma peak concentration Cmax of the parent compound 14 was 524±38 ng/ml; the area under curve $AUC_{0-t}$ was 1643±145 ng·h/ml; the half life t½ was 4.61±0.07 h; the absolute bioavailability was 52.5%. Upon measurement normalization, the plasma exposure of 14 of the group receiving 37 via intragastric administration is 157% of that of the group receiving 14 via intragastric administration.

From Table 7 and Table 8, it can be seen that after the rats were given 50 mg/kg Compound 37 via intragastric administration, the area under the plasma drug concentration-time curve, $AUC_{0-t}$, of Compound 14 was 8658±2182 ng/ml, which is 5.3 times of the $AUC_{0-t}$ value (1643 ng/ml) after administering 10 mg/kg via intragastric administration, indicating that the in vivo exposure amount is substantially proportional to dose.

After the rats were given 10 mg/kg 37 via intravenous injection, the area under the plasma drug concentration-time curve, $AUC_{0-t}$, of the parent compound 14 was 3131±349 ng·h/ml; the half life t½ was 4.88±2.41 h. Upon measurement normalization, the plasma exposure of compound 14 of the group receiving 37 via intravenous injection is 134% of that of the group receiving 14 via intravenous injection.

Seen from the metabolism results, after Compound 14 of the present invention was made into its phosphate (ester) disodium salt prodrug 37, its in vivo metabolic properties in rats were significantly improved, the speed of oral absorption increased, oral bioavailability increased from 44% to 57%, and at the same time the plasma drug exposure was significantly increased, with the oral plasma exposure being 1.5 times that of the previous, and the plasma exposure of intravenous injection also increased to 1.34 times that of the previous.

4. The In Vivo Antibacterial Activity Assay of the Compounds of the Present Invention Test strains: the strain used to infect animals was methicillin-resistant *Staphylococcus aureus* ATCC 33591 (MRSA).

Experimental animals: female ICR mice, age: 4 to 5 weeks, weight 20 to 22 grams, available from Shanghai Sippr BK Experimental Animal Co., Ltd., qualification certificate No.: 2008001625863.

Experimental method: Mice were randomly divided into groups. There were 4 dosage groups for each subject drug each administration manner: 2.5, 5, 10 and 20 mg/kg, 6 mice for each dosage group. Furthermore, a gastric mucin vehicle group was used as negative control for each administration manner. Mice were intraperitoneally injected with $10^7$-$10^8$ CFU/mL of the bacterial suspension, 0.5 ml/mouse, and at 1 hour after infection the mice were orally administered the corresponding drugs for treatment, dosing volume 0.2 mL/20 g. This research program complied with the provisions and relevant regulations of National Laboratory Animal Management and Welfare.

Result observation and $ED_{50}$ calculation: The survival of the animals in each group was observed at 48 hours, and $ED_{50}$ was calculated by using Graphpad Prism 5.0 software. The results were shown in Table 10.

TABLE 10

The in vivo efficacy of Compound 37 in mice with systemic infection by methicillin-resistant *Staphylococcus aureus* ATCC 33591 (MRSA)

| Compound | $ED_{50}$, mg/kg Oral administration |
|---|---|
| 37 | 5.00 |
| linezolid (control) | 9.87 |

Note:
the amount of infecting bacteria was $2.35 \times 10^7$ CFU/mice

Table 10 shows that, for the mouse model with systemic infection by methicillin-resistant *Staphylococcus aureus* ATCC 33591 (MRSA), the oral median effective dose $ED_{50}$ of the subject Compound 37 was remarkably lower than that of the control drug linezolid, which fully demonstrates that Compound 37 has excellent therapeutic effect on mice with systemic infection by methicillin-resistant *Staphylococcus aureus* ATCC 33591 (MRSA), and its in vivo activity is significantly better than that of the control drug linezolid, and it is more effective.

The compounds of the present invention have novel chemical structures, and in vivo and in vitro antibacterial activities superior to that of linezolid. They also exhibit great antibacterial activity on linezolid-resistant strains, and at the same time they also have ideal pharmacokinetic properties and druggability. Therefore, the compounds of the present invention can be used as medicines for the treatment of infectious diseases, especially infectious diseases caused by drug-resistant bacteria.

The invention claimed is:

1. A benzoxazine oxazolidinone compound of formula (I), an optical isomer thereof or a pharmaceutically acceptable salt thereof,

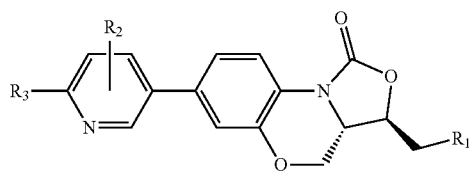

wherein, $R_1$ is hydroxyl,

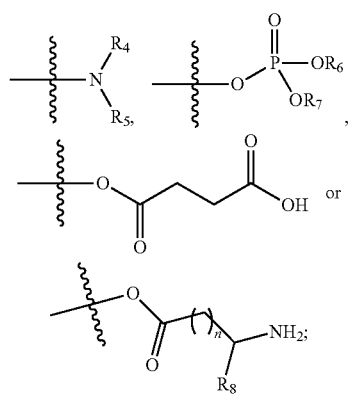

wherein, $R_4$ and $R_5$ are each independently H, hydroxyl, $C_1$-$C_4$ straight-chain or branched alkyl, and $R_4$ and $R_5$ are not hydroxyl at the same time;

$R_6$ and $R_7$ are each independently H, $C_1$-$C_4$ straight-chain or branched alkyl, or benzyl;

$R_8$ is H, $C_1$-$C_4$ straight-chain or branched alkyl, or benzyl;

N is 0 or 1;

$R_2$ is absent or $C_1$-$C_4$ straight-chain or branched alkyl;

$R_3$ is halogen; —CN; $C_1$-$C_6$ straight-chain or branched alkyl substituted by one or more groups selected from the group consisting of hydroxyl, oxo, halogen, amino, $C_3$-$C_6$ cycloalkyl and substituted or unsubstituted 5- or 6-membered aromatic heterocyclic group containing at least one heteroatom selected from N, O or S; 3- to 6-membered cycloalkyl, which is unsubstituted or substituted by amino, $C_1$-$C_4$ straight-chain or branched alkyl or hydroxyl;

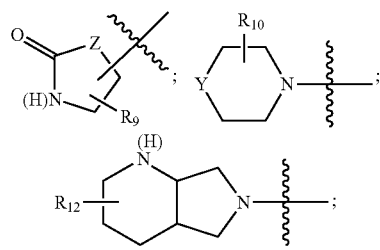

the substituent for said substituted 5- or 6-membered aromatic heterocyclic group containing at least one heteroatom selected from N, O or S is $C_1$-$C_4$ straight-chain or branched alkyl;

Z is C, N or O;

$R_9$ represents one or more substituents, which are the same or different, and which are each independently selected from the group consisting of H; $C_1$-$C_4$ straight-chain or branched alkyl; benzyl; $C_1$-$C_4$ straight-chain-chain or branched alkyl substituted by one or more groups selected from the group consisting of hydroxyl, oxo and amino; and

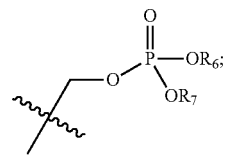

Y is C, N or O;

$R_{10}$ represents one or more substituents, which are each independently selected from the group consisting of H, hydroxyl, oxo and $C_1$-$C_4$ straight-chain or branched alkyl;

$R_{12}$ represents one or more substituents, which are each selected from the group consisting of H, hydroxyl, halogen or $C_1$-$C_4$ straight-chain or branched alkyl.

2. The benzoxazine oxazolidinone compound, optical isomer thereof or pharmaceutically acceptable salt according to claim 1, wherein, $R_1$ is hydroxyl or 3. The benzoxazine oxazolidinone compound, optical isomer thereof or pharmaceutically acceptable salt according to claim 1, wherein, $R_3$ is selected from the group consisting of CN, hydroxylmethyl, acetyl, aminomethyl,

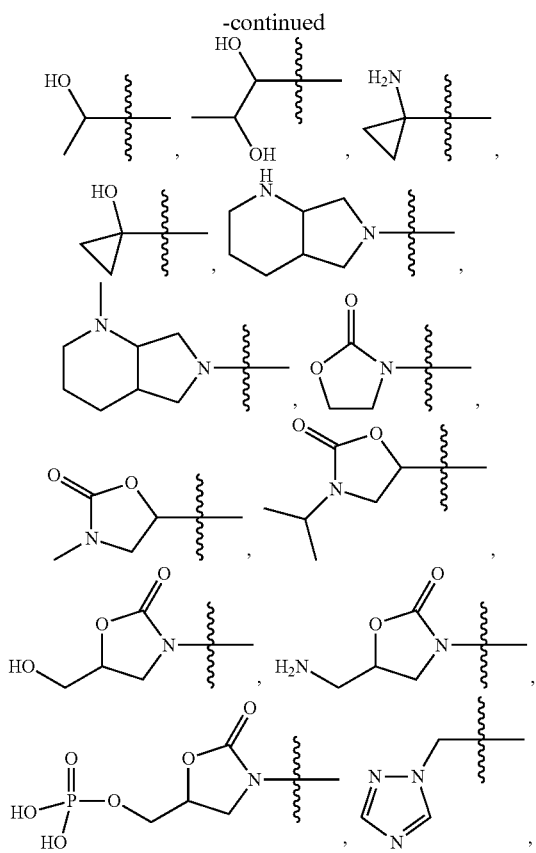
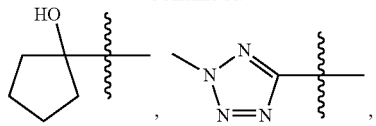
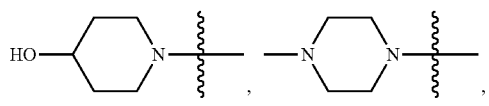
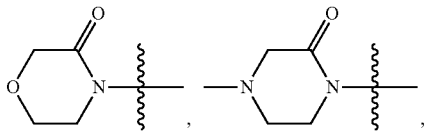
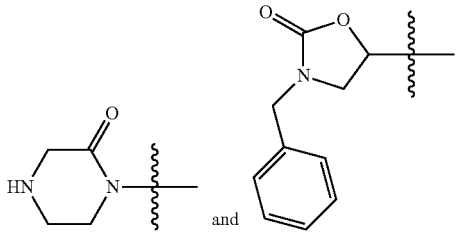
and.
4. The benzoxazine oxazolidinone compound, optical isomer thereof or pharmaceutically acceptable salt according to claim 1, wherein the compound of formula (I) is selected from the group consisting of the following compounds:
| Compound | Structure |
|---|---|
| 1 | 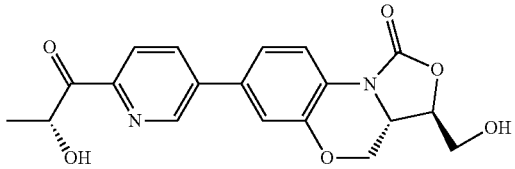 [SMILES: C[C@@H](O)C(=O)c1ccc(-c2ccc3c(c2)OC[C@H]2[C@H](CO)OC(=O)N32)cn1] |
| 2 | 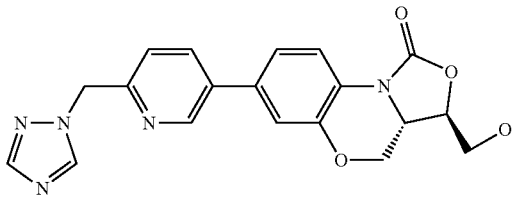 |
| 3 | 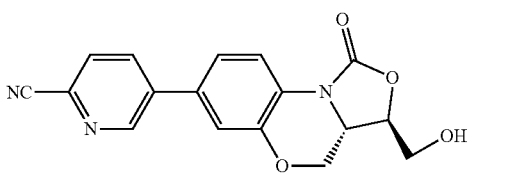 [SMILES: N#Cc1ccc(-c2ccc3c(c2)OC[C@H]2[C@H](CO)OC(=O)N32)cn1] |
| 4 | 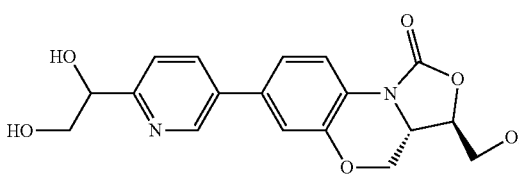 |

-continued
| Compound | Structure |
|---|---|
| 5 | 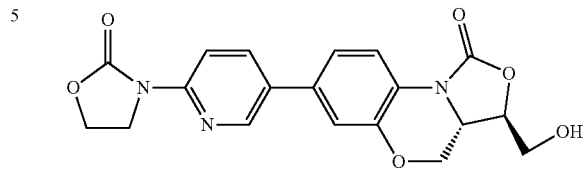 |
| 6 | 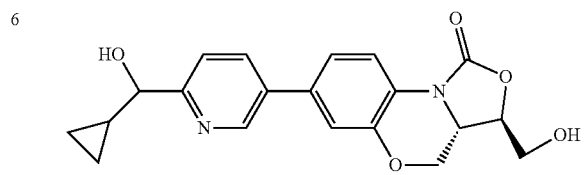 |
| 7 | 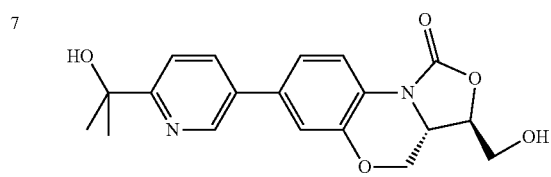 |
| 8 | 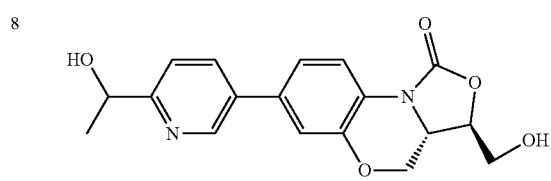 |
| 9 | 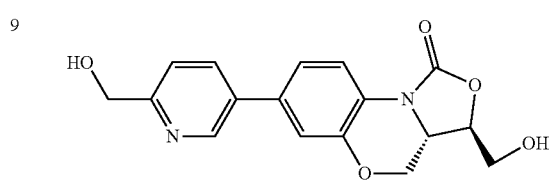 |
| 10 | 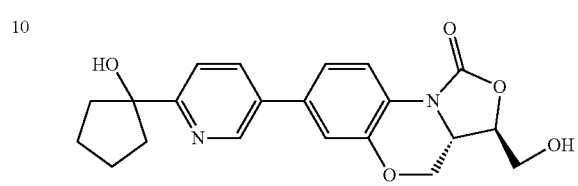 |
| 11 | 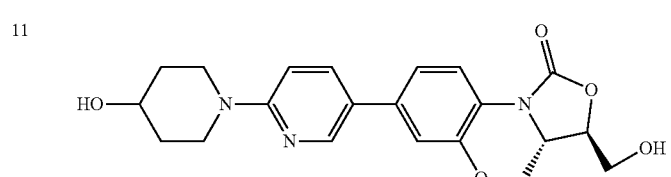 |
| 12 | 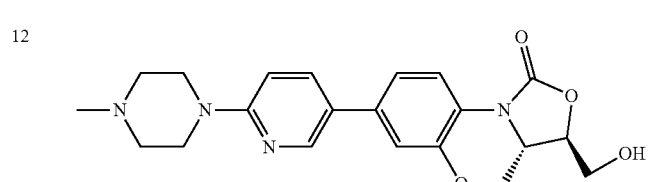 |

-continued
| Compound | Structure |
|---|---|
| 13 | 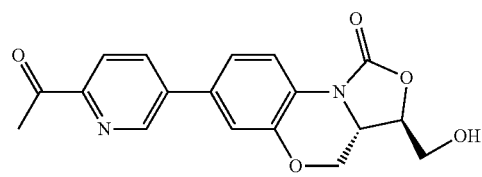 [SMILES: CC(=O)c1ccc(-c2ccc3c(c2)OC[C@H]2[C@H](CO)OC(=O)N32)cn1] |
| 14 | 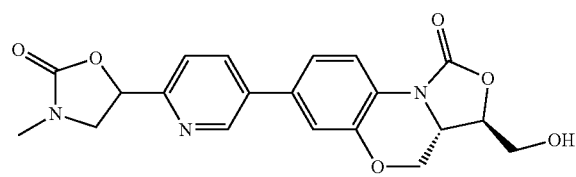 [SMILES: CN1CC(c2ccc(-c3ccc4c(c3)OC[C@H]3[C@H](CO)OC(=O)N43)cn2)OC1=O] |
| 15 | 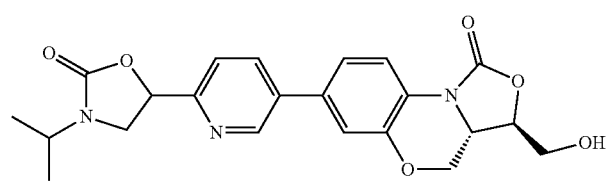 [SMILES: CC(C)N1CC(c2ccc(-c3ccc4c(c3)OC[C@H]3[C@H](CO)OC(=O)N43)cn2)OC1=O] |
| 16 | 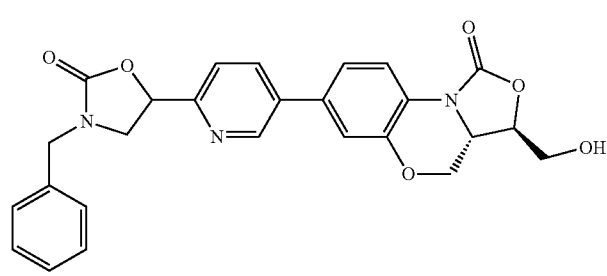 [SMILES: O=C1OC(c2ccc(-c3ccc4c(c3)OC[C@H]3[C@H](CO)OC(=O)N43)cn2)CN1Cc1ccccc1] |
| 17 | 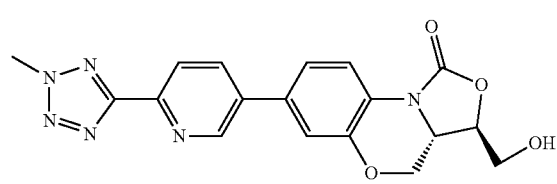 [SMILES: Cn1nnc(-c2ccc(-c3ccc4c(c3)OC[C@H]3[C@H](CO)OC(=O)N43)cn2)n1] |
| 18 | 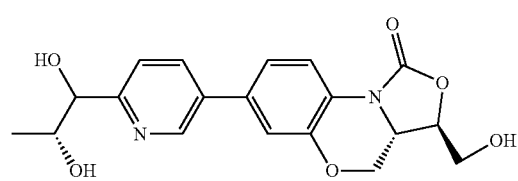 [SMILES: C[C@@H](O)C(O)c1ccc(-c2ccc3c(c2)OC[C@H]2[C@H](CO)OC(=O)N32)cn1] |
| 19 | 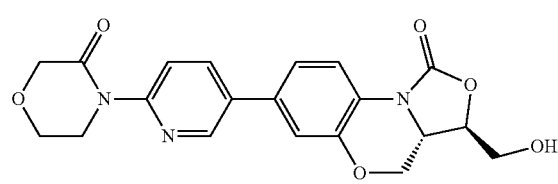 [SMILES: O=C1COCCN1c1ccc(-c2ccc3c(c2)OC[C@H]2[C@H](CO)OC(=O)N32)cn1] |
| 20 | 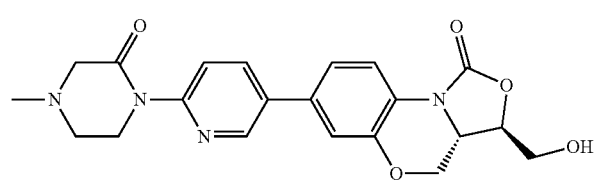 |

| Compound | Structure |
|---|---|
| 21 | 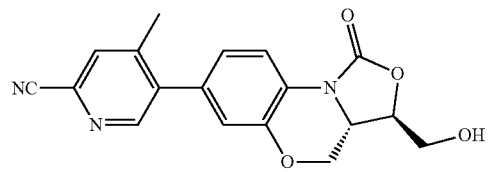 |
| 22 | 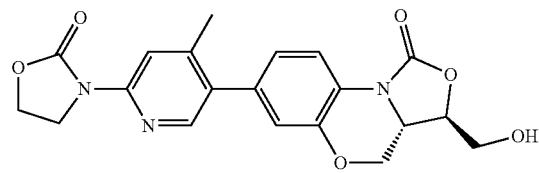 [SMILES: Cc1cc(N2CCOC2=O)ncc1-c1ccc2c(c1)OC[C@H]1[C@H](CO)OC(=O)N21] |
| 23 | 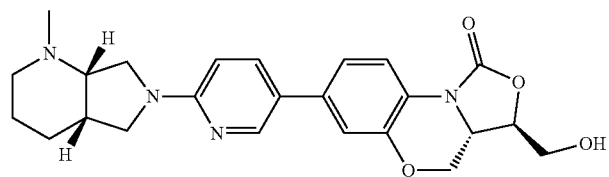 [SMILES: CN1CCC[C@H]2CN(c3ccc(-c4ccc5c(c4)OC[C@H]4[C@H](CO)OC(=O)N54)cn3)C[C@H]21] |
| 24 | 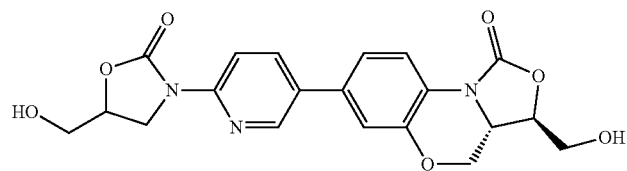 [SMILES: O=C1OC(CO)CN1c1ccc(-c2ccc3c(c2)OC[C@H]2[C@H](CO)OC(=O)N32)cn1] |
| 25 | 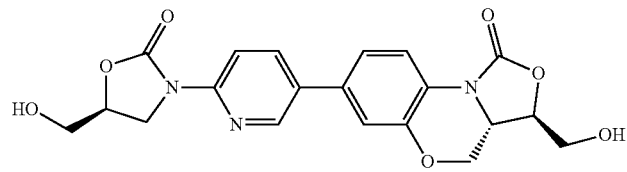 [SMILES: O=C1O[C@H](CO)CN1c1ccc(-c2ccc3c(c2)OC[C@H]2[C@H](CO)OC(=O)N32)cn1] |
| 26 | 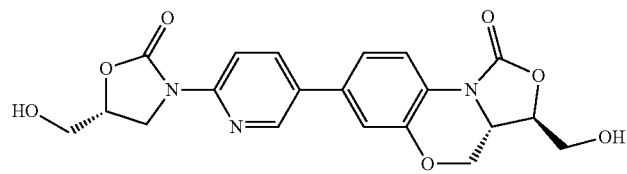 |
| 27 | 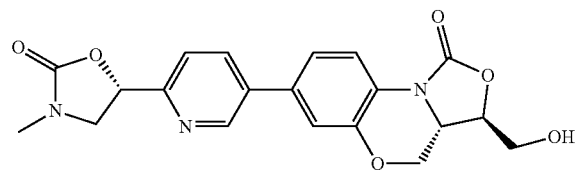 |
| 28 | 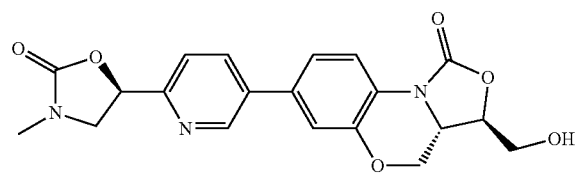 [SMILES: CN1C[C@H](c2ccc(-c3ccc4c(c3)OC[C@H]3[C@H](CO)OC(=O)N43)cn2)OC1=O] |

-continued
| Compound | Structure |
|---|---|
| 29 | 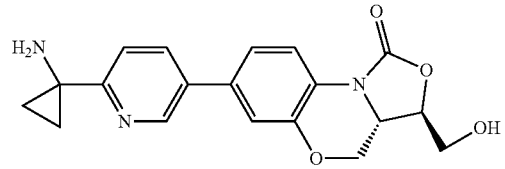 [SMILES: NC1(c2ccc(-c3ccc4c(c3)OC[C@H]3[C@H](CO)OC(=O)N43)cn2)CC1] |
| 30 | 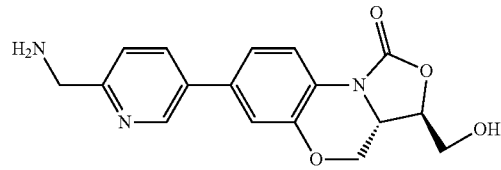 [SMILES: NCc1ccc(-c2ccc3c(c2)OC[C@H]2[C@H](CO)OC(=O)N32)cn1] |
| 31 | 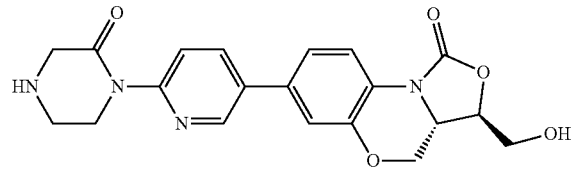 [SMILES: O=C1CNCCN1c1ccc(-c2ccc3c(c2)OC[C@H]2[C@H](CO)OC(=O)N32)cn1] |
| 32 | 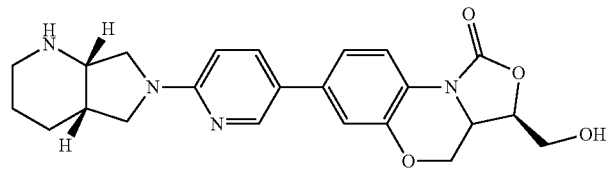 [SMILES: O=C1O[C@@H](CO)C2COc3cc(-c4ccc(N5C[C@@H]6CCCN[C@@H]6C5)nc4)ccc3N12] |
| 33 | 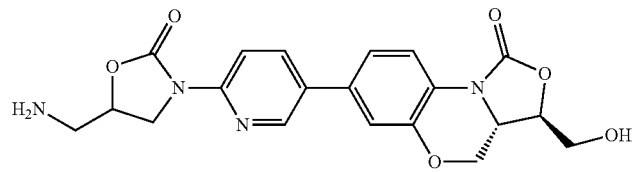 [SMILES: NCC1CN(c2ccc(-c3ccc4c(c3)OC[C@H]3[C@H](CO)OC(=O)N43)cn2)C(=O)O1] |
| 34 | 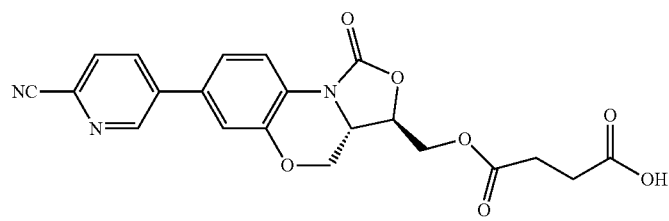 [SMILES: N#Cc1ccc(-c2ccc3c(c2)OC[C@H]2[C@H](COC(=O)CCC(=O)O)OC(=O)N32)cn1] |
| 35 | 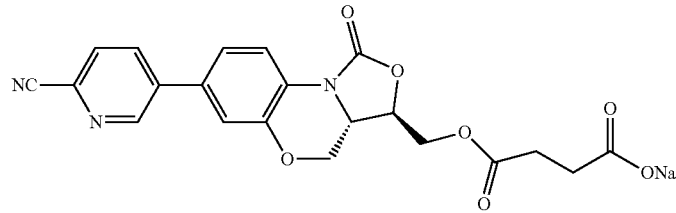 |
| 36 | 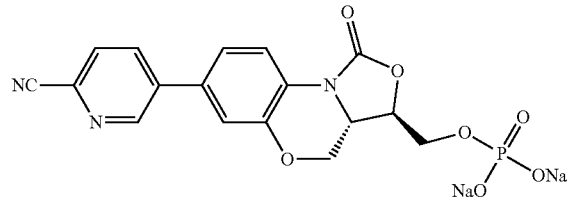 |

| Compound | Structure |
|---|---|
| 37 | 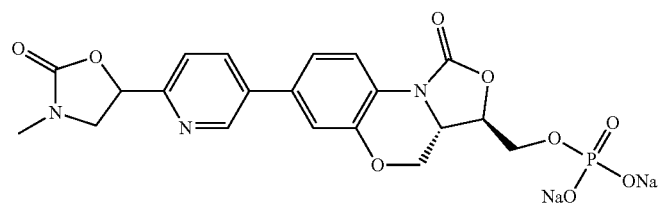 |
| 38 | 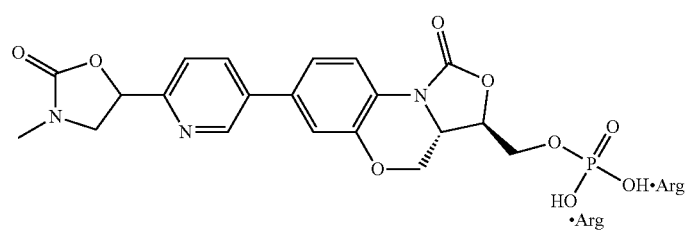 |
| 39 | 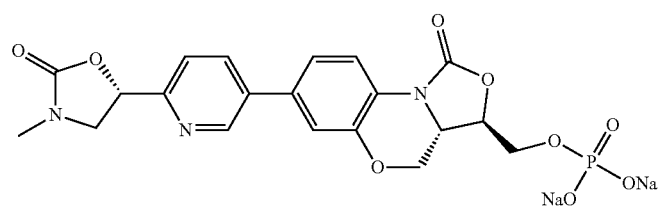 |
| 40 | 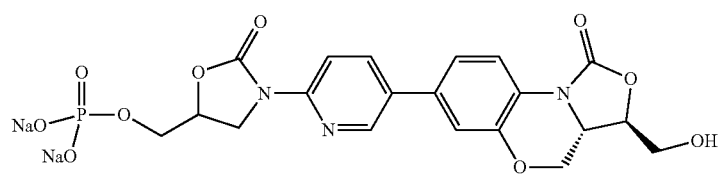 |
| 41 | 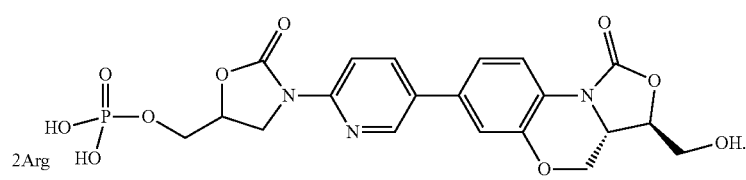 [SMILES: O=C1OC(COP(=O)(O)O)CN1c1ccc(-c2ccc3c(c2)OC[C@H]2[C@H](CO)OC(=O)N32)cn1] |

5. The benzoxazine oxazolidinone compound, optical isomer thereof or pharmaceutically acceptable salt according to claim 1, wherein the pharmaceutically acceptable salts of the benzoxazine oxazolidinone compounds represented by formula (I) include: salts formed with inorganic acids; addition salts formed with organic acids or with acidic amino acids; metal salts formed with alkali; addition salts formed with basic amino acids such as arginine acid or lysine.

6. A preparation method of the benzoxazine oxazolidinone compound, optical isomer thereof or pharmaceutically acceptable salt thereof according claim 1, which comprises the following steps:

Scheme I

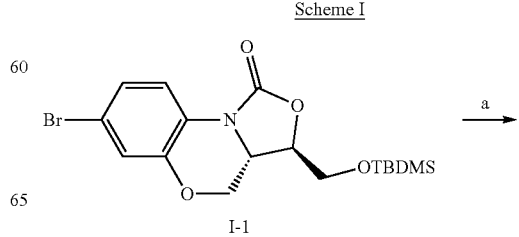

-continued

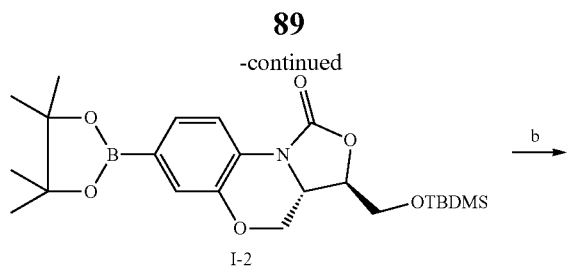
I-2

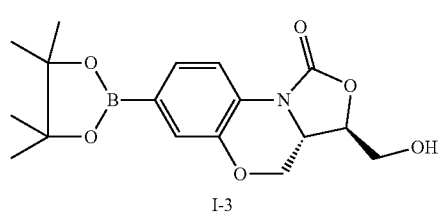
I-3 a) in a polar solvent under alkaline condition, compound I-1 and bis(pinacolato)diboron react with the catalysation by a palladium-containing catalyst in the presence of a phosphine-containing ligand under the protection of inert gas to give compound I-2;
b) compound I-2 reacts in a polar solvent in the presence of a fluorine-containing reagent to remove the protecting group tert-butyldimethylsilyl, thereby producing compound I-3;
or react, with the catalysation by a palladium-containing catalyst, under the protection of inert gas to give the corresponding compound II-2;
or
d) in a polar solvent under alkaline condition, compound I-3 reacts with the halide

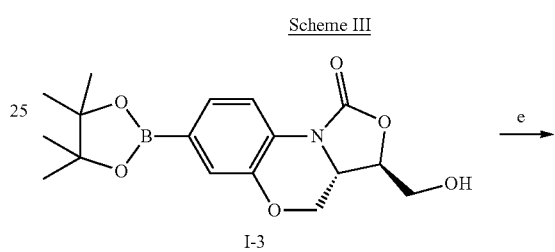

in the presence of a palladium-containing catalyst, under the protection of inert gas to give the corresponding compound II-2;
or Scheme III

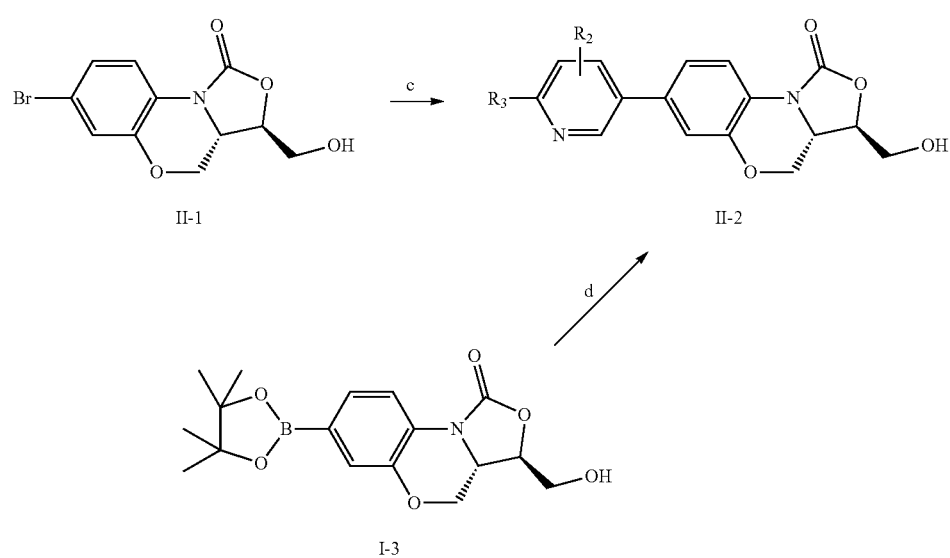

Scheme II

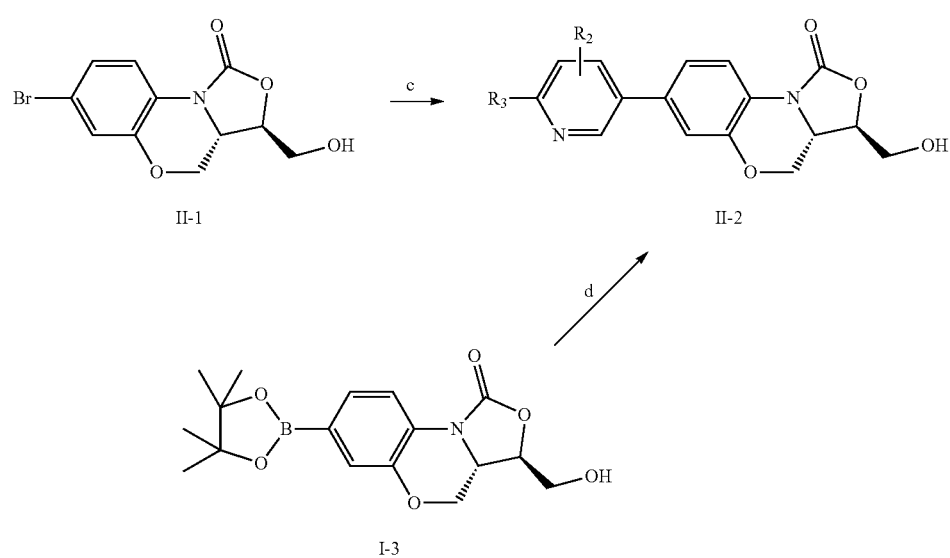

c) in a polar solvent under alkaline condition, compound II-1 and

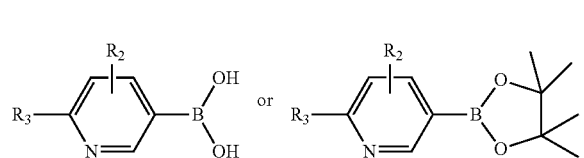

-continued

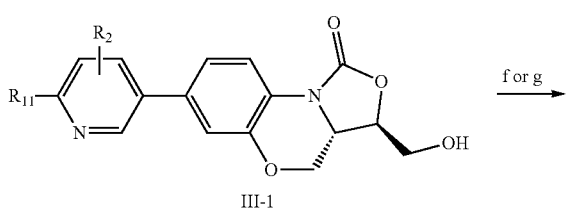
III-1

-continued

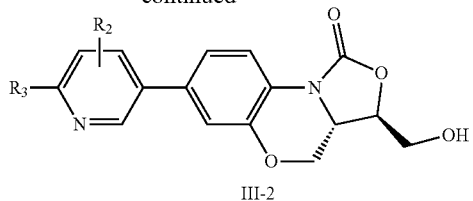
III-2

$R_{11}$ is

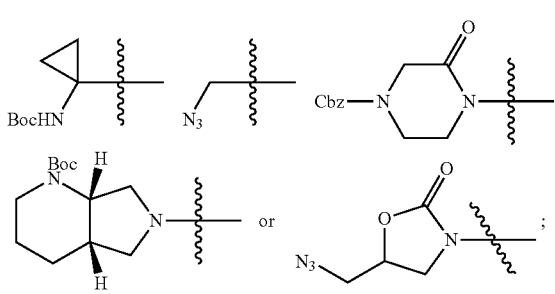

$R_3$ is

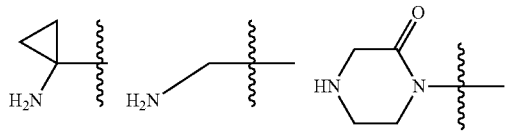

-continued

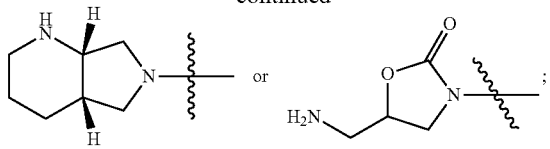

e) in a polar solvent under alkaline condition, compound I-3 reacts with the halide

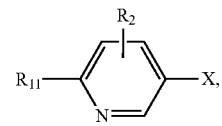

in the presence of a palladium-containing catalyst, under the protection of inert gas to give the corresponding compound III-1;

f) under the circumstance that $R_{11}$ contains —$N_3$, compound III-1 is dissolved in a polar solvent, and subjected to catalytic hydrogenation in the presence of a metal catalyst to obtain compound III-2 with an $R_3$ containing —$NH_2$, or is reduced by a suitable reducing agent in a polar solvent to obtain compound III-2 containing —$NH_2$;

g) under the circumstance that $R_{11}$ contains a Boc protecting group, the protecting group is removed from compound III-1 in a polar solvent under acidic condition to obtain the corresponding compound III-2 without the Boc protecting group;
or

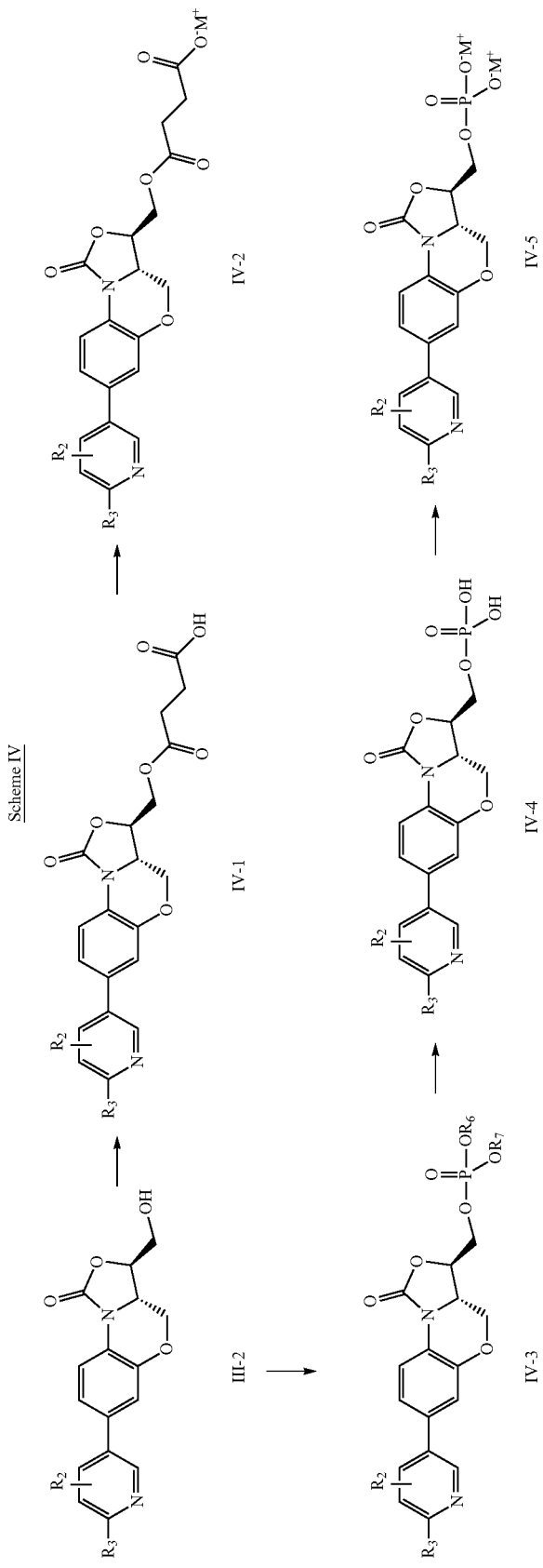
Scheme IV $R_2$, $R_3$, $R_6$ and $R_7$ are defined as in claim 1; M is metal or amino acid;

h) compound III-2 reacts with succinic anhydride in a polar solvent in the presence of an alkali to obtain the corresponding succinate monoester compound IV-1;

i) compound IV-1 reacts with an alkali in a polar solvent to obtain the corresponding succinate monoester salt compound IV-2;

j) compound III-2 reacts with a phosphite ester in the presence of an activating agent in a polar solvent under the protection of inner gas to obtain the corresponding phosphite ester compound; the phosphite ester compound reacts in the presence of an oxidizing agent in a polar solvent under the protection of inner gas to obtain the corresponding phosphate ester compound IV-3;

k) the phosphate ester compound IV-3 is subjected to catalytic hydrogenation in a polar solvent in the presence of a metal catalyst or react under acidic condition to obtain the corresponding phosphate monoester compound IV-4;

o) the phosphate monoester compound IV-4 reacts with an alkali in a polar solvent to obtain the corresponding phosphate salt compound IV-5;

m) for compound II-2 with $R_3$ containing a hydroxyl, the phosphate monoester salt or amino acid ester salt thereof is prepared following the above method, wherein X represents halogen.

7. The preparation method according to claim 6, wherein in step a), said palladium-containing catalyst is $Pd(PPh_3)_4$, $Pd(dppf)Cl_2$, $Pd(dppf)Cl_2 \cdot CH_2Cl_2$ or $Pd(dba)_2$;

said phosphine-containing ligand is biphenyl-2-yldi-tert-butylphosphine;

the alkali used for said alkaline condition is potassium acetate, sodium acetate, potassium tert-butoxide or sodium tert-butoxide;

said polar solvent is dimethyl sulfoxide, N,N-dimethyl formamide, 1,4-dioxane, tetrahydrofuran or toluene;

said inner gas is nitrogen or argon;

in step b), said fluorine-containing reagent is tetra-n-butyl ammonium fluoride; said polar solvent is tetrahydrofuran or ethylene glycol dimethyl ether;

in step c), said palladium-containing catalyst is tetrakis(triphenylphosphine)palladium, 1,1'-bis(diphenylphosphino) ferrocene palladium (II) dichloride, 1,1'-bis(diphenylphosphino) ferrocene-palladium (II) dichloride dichloromethane complex, tris(dibenzylideneacetone)dipalladium (0), bis(dibenzylideneacetone)palladium (0), bis(triphenyl)phosphinepalladium(II) dichloride or palladium acetate;

the alkali used for said alkaline condition is cesium carbonate, potassium acetate, sodium carbonate, potassium phosphate or potassium fluoride;

said polar solvent is 1,4-dioxane, tetrahydrofuran, ethylene glycol dimethyl ether, N,N-dimethyl formamide, ethanol or water or the mixtures thereof; said inner gas is nitrogen or argon;

in step d), said palladium-containing catalyst is $Pd(PPh_3)_4$, $Pd(dppf)Cl_2 \cdot CH_2Cl_2$, $Pd(dppf)Cl_2$, $Pd(PPh_3)_2Cl_2$ or $Pd(OAc)_2$;

the alkali used for said alkaline condition is $Cs_2CO_3$, $K_2CO_3$, $K_3PO_4$ or KF;

said polar solvent is 1,4-dioxane, tetrahydrofuran, water, ethylene glycol dimethyl ether, ethanol, N,N-dimethyl formamide, toluene or the mixtures thereof; said inner gas is nitrogen or argon;

in step e), wherein, X represents halogen; said palladium-containing catalyst is $Pd(PPh_3)_4$, $Pd(dppf)Cl_2 \cdot CH_2Cl_2$, $Pd(dppf)Cl_2$, $Pd(PPh_3)_2Cl_2$ or $Pd(OAc)_2$; the alkali used for said alkaline condition is $Cs_2CO_3$, $K_2CO_3$, $K_3PO_4$ or KF; said polar solvent is 1,4-dioxane, tetrahydrofuran, water, ethylene glycol dimethyl ether, ethanol, N,N-dimethyl formamide or toluene or the mixtures thereof; said inner gas is nitrogen or argon;

in step f), said polar solvent is dichloromethane, methanol, ethanol, tetrahydrofuran, $H_2O$ or the mixtures thereof;

said metal catalyst is palladium/carbon or other metal catalysts containing palladium or nickel;

said reducing agent is sodium borohydride, lithium aluminium hydride, triphenyl phosphine or tributyl phosphine;

in step g), said acid is trifluoroacetic acid or hydrochloric acid;

said polar solvent is dichloromethane, ethyl acetate, methanol, acetone, tetrahydrofuran, acetonitrile or the mixtures thereof;

in step h), said polar solvent is dichloromethane, acetonitrile, tetrahydrofuran, N,N-dimethyl formamide or the mixtures thereof; said alkali is triethylamine, DIPEA, pyridine or DMAP;

in step i), said alkali is sodium methoxide, sodium carbonate, sodium isooctoate, sodium hydroxide, calcium chloride, calcium acetate, magnesium chloride, magnesium hydroxide, magnesium acetate, arginine, or lysine;

the polar solvent is water, acetone, ethyl acetate, acetonitrile, N,N-dimethyl formamide, N,N-dimethyl acetamide, 1,4-dioxane, or tetrahydrofuran;

in step j), said phosphite ester is tert-butyl phosphite, or dibenzyl diisopropylamino phosphite;

the activating agent is 4,5-dicyano imidazole, or 1H-tetrazole;

the polar solvent is dichloromethane, acetonitrile, tetrahydrofuran or the mixtures thereof;

the inert gas is nitrogen or argon;

the oxidizing agent is m-chloro-peroxybenzoic acid, or tert-butyl hydroperoxide;

in step k), said polar solvent is dichloromethane, methanol, ethanol, isopropanol, etrahydrofuran, acetone, 1,4-dioxane, N,N-dimethyl formamide or the mixtures thereof; the metal catalyst is palladium/carbon or other metal catalysts containing palladium or nickel; said acid is trifluoroacetic acid, or hydrochloric acid;

in step o), said alkali is sodium methoxide, sodium carbonate, sodium isooctoate, sodium hydroxide, calcium chloride, calcium acetate, magnesium chloride, magnesium hydroxide, magnesium acetate, arginine, or lysine; the polar solvent is water, acetone, ethyl acetate, acetonitrile, N,N-dimethyl formamide, N,N-dimethyl acetamide, 1,4-dioxane, or tetrahydrofuran.

8. A pharmaceutical composition, which comprises a therapeutically effective amount of one or more of the benzoxazine oxazolidinone compound of formula (I), optical isomer thereof or pharmaceutically acceptable salt thereof according to claim 1 as active ingredient, and a pharmaceutically acceptable auxiliary material.

9. A method of treating a bacterial infection in a subject in need thereof, comprising administering to said subject an effective amount of the benzoxazine oxazolidinone compound of formula (I), optical isomer thereof or pharmaceutically acceptable salt thereof according to claim 1.

10. The method according to claim 9, wherein said infection is caused by enterococci, *Staphylococcus aureus, Staphylococcus epidermidis* or *Streptococcus pneumonia*.

* * * * *